US011583289B2

(12) United States Patent
Connor

(10) Patent No.: US 11,583,289 B2
(45) Date of Patent: Feb. 21, 2023

(54) ANEURYSM-OCCLUDING MESH RIBBON WITH A SERIES OF LOOPS OR SEGMENTS HAVING DISTAL-TO-PROXIMAL VARIATION IN SIZE, SHAPE, AND/OR ORIENTATION

(71) Applicant: Robert A. Connor, St. Paul, MN (US)

(72) Inventor: Robert A. Connor, St. Paul, MN (US)

(73) Assignee: Aneuclose LLC, St. Paul, MN (US)

( * ) Notice: Subject to any disclaimer, the term of this patent is extended or adjusted under 35 U.S.C. 154(b) by 0 days.

(21) Appl. No.: 17/476,845

(22) Filed: Sep. 16, 2021

(65) Prior Publication Data
US 2022/0000490 A1   Jan. 6, 2022

Related U.S. Application Data

(63) Continuation-in-part of application No. 17/472,674, filed on Sep. 12, 2021, now abandoned, and a continuation-in-part of application No. 17/467,680, filed on Sep. 7, 2021, now abandoned, and a continuation-in-part of application No. 17/466,497, filed on Sep. 3, 2021, now Pat. No. 11,357,511, and a continuation-in-part of application No. 17/353,652, filed on Jun. 21, 2021, now abandoned, and a continuation-in-part of application No. 17/220,002, filed on Apr. 1, 2021, now Pat. No. 11,464,518, which is a continuation-in-part of application No. 17/214,827, filed on Mar. 27, 2021, now Pat. No. 11,484,322, application No. 17/476,845, which is a continuation-in-part of application No. 17/214,827,
(Continued)

(51) Int. Cl.
A61B 17/12   (2006.01)
A61B 34/00   (2016.01)
A61B 17/00   (2006.01)

(52) U.S. Cl.
CPC .. *A61B 17/12172* (2013.01); *A61B 17/12113* (2013.01); *A61B 34/73* (2016.02); *A61B 2017/00323* (2013.01)

(58) Field of Classification Search
CPC ........ A61B 17/12118; A61B 17/12113; A61B 17/12172; A61B 17/12163
See application file for complete search history.

(56) References Cited

U.S. PATENT DOCUMENTS 8,597,320 B2   12/2013   Sepetka et al.
8,974,512 B2    3/2015   Aboytes et al.
(Continued)

OTHER PUBLICATIONS

U.S. Appl. No. 61/483,032, filed May 5, 2011, Kent et al.
(Continued)

*Primary Examiner* — Diane D Yabut
*Assistant Examiner* — Christina C Lauer

(57) ABSTRACT

This invention is an intrasacular aneurysm occlusion device with a longitudinal mesh ribbon having a series of loops or segments with distal-to-proximal variation in their sizes, shapes, or orientations. For example, loops or segments can be progressively smaller in size and/or progressively more curved as one views the series in a distal-to-proximal direction. The device may also enable a user to selectively and remotely bend, steer, or elongate the loops or segments in real time as the ribbon is being deployed into an aneurysm sac.

10 Claims, 16 Drawing Sheets

Related U.S. Application Data filed on Mar. 27, 2021, now Pat. No. 11,484,322, said application No. 17/220,002 is a continuation-in-part of application No. 17/211,446, filed on Mar. 24, 2021, now abandoned, application No. 17/476,845, which is a continuation-in-part of application No. 17/211,446, filed on Mar. 24, 2021, now abandoned, said application No. 17/220,002 is a continuation-in-part of application No. 16/693,267, filed on Nov. 23, 2019, now abandoned, application No. 17/476,845, which is a continuation-in-part of application No. 16/693,267, filed on Nov. 23, 2019, now abandoned, and a continuation-in-part of application No. 16/660,929, filed on Oct. 23, 2019, now Pat. No. 11,471,163, said application No. 16/693,267 is a continuation-in-part of application No. 16/660,929, filed on Oct. 23, 2019, now Pat. No. 11,471,163, said application No. 17/220,002 is a continuation-in-part of application No. 16/660,929, filed on Oct. 23, 2019, now Pat. No. 11,471,163, said application No. 16/693,267 is a continuation-in-part of application No. 16/541,241, filed on Aug. 15, 2019, now abandoned, application No. 17/476,845, which is a continuation-in-part of application No. 16/541,241, filed on Aug. 15, 2019, now abandoned, said application No. 16/660,929 is a continuation-in-part of application No. 16/541,241, filed on Aug. 15, 2019, now abandoned, and a continuation-in-part of application No. 15/865,822, filed on Jan. 9, 2018, now Pat. No. 10,716,573, said application No. 16/693,267 is a continuation-in-part of application No. 15/865,822, filed on Jan. 9, 2018, now Pat. No. 10,716,573, said application No. 16/541,241 is a continuation-in-part of application No. 15/865,822, filed on Jan. 9, 2018, now Pat. No. 10,716,573, said application No. 16/660,929 is a continuation-in-part of application No. 15/861,482, filed on Jan. 3, 2018, now abandoned, said application No. 16/693,267 is a continuation-in-part of application No. 15/861,482, filed on Jan. 3, 2018, now abandoned, said application No. 15/865,822 is a continuation-in-part of application No. 15/081,909, filed on Mar. 27, 2016, now abandoned, said application No. 15/861,482 is a continuation-in-part of application No. 15/080,915, filed on Mar. 25, 2016, now Pat. No. 10,028,747, which is a continuation-in-part of application No. 14/526,600, filed on Oct. 29, 2014, now abandoned, said application No. 15/081,909 is a continuation-in-part of application No. 14/526,600, filed on Oct. 29, 2014, now abandoned, said application No. 15/861,482 is a continuation-in-part of application No. 14/526,600, filed on Oct. 29, 2014, now abandoned, said application No. 15/865,822 is a continuation-in-part of application No. 14/526,600, filed on Oct. 29, 2014, now abandoned, which is a continuation-in-part of application No. 12/989,048, filed on Oct. 21, 2010, now Pat. No. 8,974,487.

(60) Provisional application No. 63/119,774, filed on Dec. 1, 2020, provisional application No. 62/794,607, filed on Jan. 19, 2019, provisional application No. 62/794,609, filed on Jan. 19, 2019, provisional application No. 62/720,173, filed on Aug. 21, 2018, provisional application No. 62/589,754, filed on Nov. 22, 2017, provisional application No. 62/472,519, filed on Mar. 16, 2017, provisional application No. 62/444,860, filed on Jan. 11, 2017, provisional application No. 61/897,245, filed on Oct. 30, 2013, provisional application No. 61/126,047, filed on May 1, 2008, provisional application No. 61/126,027, filed on May 1, 2008.

(56) References Cited

U.S. PATENT DOCUMENTS

| | | |
|---|---|---|
| 8,998,947 B2 | 4/2015 | Aboytes et al. |
| 9,039,726 B2 | 5/2015 | Becking |
| 9,078,658 B2 | 7/2015 | Hewitt et al. |
| 9,492,174 B2 | 11/2016 | Hewitt et al. |
| 9,585,669 B2 | 3/2017 | Becking et al. |
| 9,629,635 B2 | 4/2017 | Hewitt et al. |
| 9,955,976 B2 | 5/2018 | Hewitt et al. |
| 9,980,733 B2 | 5/2018 | Badruddin et al. |
| 10,130,372 B2 | 11/2018 | Griffin |
| 10,265,075 B2 | 4/2019 | Porter et al. |
| 10,285,711 B2 | 5/2019 | Griffin |
| 10,314,593 B2 | 6/2019 | Bardsley et al. |
| 10,327,781 B2 | 6/2019 | Divino et al. |
| 10,383,635 B2 | 8/2019 | Wallace et al. |
| 10,398,441 B2 | 9/2019 | Warner et al. |
| 10,426,486 B2 | 10/2019 | Guo et al. |
| 10,433,853 B2 | 10/2019 | Divino et al. |
| 10,595,875 B2 | 3/2020 | Mayer et al. |
| 10,610,231 B2 | 4/2020 | Marchand et al. |
| 10,617,426 B2 | 4/2020 | Aboytes et al. |
| 10,617,427 B2 | 4/2020 | Aboytes et al. |
| 10,653,425 B1 | 5/2020 | Gorochow et al. |
| 10,675,036 B2 | 6/2020 | Rosqueta et al. |
| 10,675,037 B2 | 6/2020 | Aboytes et al. |
| 10,716,574 B2 | 7/2020 | Lorenzo et al. |
| 10,729,447 B2 | 8/2020 | Shimizu et al. |
| 10,736,758 B2 | 8/2020 | Ruvalcaba et al. |
| 10,751,066 B2 | 8/2020 | Lorenzo |
| 10,813,645 B2 | 10/2020 | Hewitt et al. |
| 10,856,880 B1 | 12/2020 | Badruddin et al. |
| 10,869,672 B2 | 12/2020 | Griffin |
| 10,881,413 B2 | 1/2021 | Merritt et al. |
| 10,898,200 B2 | 1/2021 | Aboytes et al. |
| 10,905,430 B2 | 2/2021 | Lorenzo et al. |
| 10,905,431 B2 | 2/2021 | Gorochow |
| 10,925,612 B2 | 2/2021 | Wallace et al. |
| 10,939,914 B2 | 3/2021 | Hewitt et al. |
| 10,939,915 B2 | 3/2021 | Gorochow et al. |
| 10,939,916 B2 | 3/2021 | Aboytes et al. |
| 10,952,739 B2 | 3/2021 | Plaza et al. |
| 10,952,878 B2 | 3/2021 | Kusleika |
| 10,980,545 B2 | 4/2021 | Bowman et al. |
| 11,013,516 B2 | 5/2021 | Franano et al. |
| 11,033,275 B2 | 6/2021 | Franano et al. |
| 11,033,277 B2 | 6/2021 | Wolfe et al. |
| 11,045,203 B2 | 6/2021 | Sepetka et al. |
| 11,051,825 B2 | 7/2021 | Gorochow |
| 11,058,430 B2 | 7/2021 | Gorochow et al. |
| 11,058,431 B2 | 7/2021 | Pereira et al. |
| 11,071,551 B2 | 7/2021 | Garza et al. |
| 11,076,860 B2 | 8/2021 | Lorenzo |
| 11,076,861 B2 | 8/2021 | Gorochow et al. |
| 2002/0169473 A1 | 11/2002 | Sepetka et al. |
| 2003/0120300 A1* | 6/2003 | Porter ............ A61B 17/12022 606/191 |
| 2006/0155323 A1 | 7/2006 | Porter et al. |
| 2008/0281350 A1 | 11/2008 | Sepetka et al. |
| 2009/0287294 A1 | 11/2009 | Rosqueta et al. |
| 2011/0022149 A1 | 1/2011 | Cox et al. |
| 2011/0208227 A1 | 8/2011 | Becking |
| 2012/0165919 A1 | 6/2012 | Cox et al. |
| 2012/0239074 A1* | 9/2012 | Aboytes ........... A61B 17/00234 606/191 |
| 2012/0283768 A1 | 11/2012 | Cox et al. |
| 2013/0245667 A1 | 9/2013 | Marchand et al. |
| 2014/0052233 A1 | 2/2014 | Cox et al. |
| 2014/0135812 A1 | 5/2014 | Divino et al. |

(56) References Cited

U.S. PATENT DOCUMENTS

| | | |
|---|---|---|
| 2014/0358178 A1 | 12/2014 | Hewitt et al. |
| 2015/0209050 A1 | 7/2015 | Aboytes et al. |
| 2015/0216684 A1 | 8/2015 | Enzmann et al. |
| 2015/0272589 A1 | 10/2015 | Lorenzo |
| 2015/0272590 A1 | 10/2015 | Aboytes et al. |
| 2015/0297240 A1 | 10/2015 | Divino et al. |
| 2015/0313605 A1 | 11/2015 | Griffin |
| 2016/0022275 A1 | 1/2016 | Garza |
| 2016/0022445 A1 | 1/2016 | Ruvalcaba et al. |
| 2016/0213380 A1 | 7/2016 | O'Brien et al. |
| 2016/0249934 A1 | 9/2016 | Hewitt et al. |
| 2016/0249935 A1 | 9/2016 | Hewitt et al. |
| 2016/0249937 A1 | 9/2016 | Marchand et al. |
| 2016/0262766 A1 | 9/2016 | Aboytes et al. |
| 2016/0367260 A9 | 12/2016 | Hewitt et al. |
| 2017/0079661 A1 | 3/2017 | Bardsley et al. |
| 2017/0079662 A1 | 3/2017 | Rhee et al. |
| 2017/0086851 A1 | 3/2017 | Wallace et al. |
| 2017/0095254 A1 | 5/2017 | Hewitt et al. |
| 2017/0128077 A1 | 5/2017 | Hewitt et al. |
| 2017/0156733 A1 | 6/2017 | Becking et al. |
| 2017/0156734 A1 | 6/2017 | Griffin |
| 2017/0189035 A1 | 7/2017 | Porter |
| 2017/0258473 A1 | 9/2017 | Plaza et al. |
| 2017/0281194 A1 | 10/2017 | Divino et al. |
| 2017/0354418 A1 | 12/2017 | Teoh et al. |
| 2018/0000489 A1 | 1/2018 | Marchand et al. |
| 2018/0036012 A1 | 2/2018 | Aboytes et al. |
| 2018/0070955 A1 | 3/2018 | Greene et al. |
| 2018/0092690 A1 | 4/2018 | Priya et al. |
| 2018/0132859 A1 | 5/2018 | Aboytes et al. |
| 2018/0132862 A1 | 5/2018 | Aboytes et al. |
| 2018/0206849 A1 | 7/2018 | Hewitt et al. |
| 2018/0242979 A1 | 8/2018 | Lorenzo |
| 2018/0250013 A1 | 9/2018 | Wallace et al. |
| 2018/0271540 A1 | 9/2018 | Merritt et al. |
| 2018/0303486 A1 | 10/2018 | Rosenbluth et al. |
| 2019/0008522 A1 | 1/2019 | Lorenzo |
| 2019/0053810 A1 | 2/2019 | Griffin |
| 2019/0053811 A1 | 2/2019 | Garza et al. |
| 2019/0059909 A1 | 2/2019 | Griffin |
| 2019/0105054 A1 | 4/2019 | Aboytes et al. |
| 2019/0105056 A1 | 4/2019 | Aboytes et al. |
| 2019/0133794 A1 | 5/2019 | Kusleika |
| 2019/0192166 A1 | 6/2019 | Hewitt et al. |
| 2019/0192168 A1 | 6/2019 | Lorenzo et al. |
| 2019/0201000 A1 | 7/2019 | Wallace et al. |
| 2019/0209178 A1 | 7/2019 | Richter et al. |
| 2019/0209181 A1 | 7/2019 | Mayer et al. |
| 2019/0216467 A1 | 7/2019 | Goyal |
| 2019/0223878 A1 | 7/2019 | Lorenzo et al. |
| 2019/0223881 A1 | 7/2019 | Hewitt et al. |
| 2019/0254676 A1 | 8/2019 | Murphy et al. |
| 2019/0262002 A1 | 8/2019 | Benjamin |
| 2019/0269411 A1 | 9/2019 | Bardsley et al. |
| 2019/0269414 A1 | 9/2019 | Griffin |
| 2019/0274691 A1 | 9/2019 | Sepetka et al. |
| 2019/0282242 A1 | 9/2019 | Divino et al. |
| 2019/0290286 A1 | 9/2019 | Divino et al. |
| 2019/0298379 A1 | 10/2019 | Porter et al. |
| 2019/0307460 A1 | 10/2019 | Ferrera et al. |
| 2019/0307546 A1 | 10/2019 | Aguilar et al. |
| 2019/0343532 A1 | 11/2019 | Divino et al. |
| 2019/0343664 A1 | 11/2019 | Ruvalcaba et al. |
| 2019/0350590 A1 | 11/2019 | Aboytes et al. |
| 2019/0362496 A1 | 11/2019 | Dutta et al. |
| 2019/0365385 A1 | 12/2019 | Gorochow et al. |
| 2019/0365472 A1 | 12/2019 | Connor |
| 2019/0374228 A1 | 12/2019 | Wallace et al. |
| 2020/0038032 A1 | 2/2020 | Rhee et al. |
| 2020/0038035 A1 | 2/2020 | Griffin |
| 2020/0113576 A1 | 4/2020 | Gorochow et al. |
| 2020/0138447 A1 | 5/2020 | Rosqueta et al. |
| 2020/0155333 A1 | 5/2020 | Franano et al. |
| 2020/0163677 A1 | 5/2020 | Mayer et al. |
| 2020/0163784 A1 | 5/2020 | Franano et al. |
| 2020/0187952 A1 | 6/2020 | Walsh et al. |
| 2020/0187953 A1 | 6/2020 | Hamel et al. |
| 2020/0187954 A1 | 6/2020 | Hamel et al. |
| 2020/0197017 A1 | 6/2020 | Hamel et al. |
| 2020/0197018 A1 | 6/2020 | Hamel et al. |
| 2020/0197020 A1 | 6/2020 | Hamel et al. |
| 2020/0205841 A1 | 7/2020 | Aboytes et al. |
| 2020/0281603 A1 | 9/2020 | Marchand et al. |
| 2020/0289124 A1 | 9/2020 | Rangwala et al. |
| 2020/0289125 A1 | 9/2020 | Dholakia et al. |
| 2020/0289126 A1 | 9/2020 | Hewitt et al. |
| 2020/0360025 A1 | 11/2020 | Wallace et al. |
| 2020/0367893 A1 | 11/2020 | Xu et al. |
| 2020/0367898 A1 | 11/2020 | Gorochow et al. |
| 2020/0367900 A1 | 11/2020 | Pedroso et al. |
| 2020/0367901 A1 | 11/2020 | Porter et al. |
| 2020/0367906 A1 | 11/2020 | Xu et al. |
| 2020/0375606 A1 | 12/2020 | Lorenzo |
| 2020/0375607 A1 | 12/2020 | Soto Del Valle et al. |
| 2020/0397447 A1 | 12/2020 | Lorenzo et al. |
| 2020/0405347 A1 | 12/2020 | Walzman |
| 2021/0007754 A1 | 1/2021 | Milhous et al. |
| 2021/0007755 A1 | 1/2021 | Lorenzo et al. |
| 2021/0022765 A1 | 1/2021 | Walzman |
| 2021/0045750 A1 | 2/2021 | Wolf et al. |
| 2021/0052278 A1 | 2/2021 | Mauger |
| 2021/0052279 A1 | 2/2021 | Porter et al. |
| 2021/0068842 A1 | 3/2021 | Griffin |
| 2021/0069387 A1 | 3/2021 | Chen et al. |
| 2021/0085333 A1 | 3/2021 | Gorochow et al. |
| 2021/0106337 A1 | 4/2021 | Hewitt et al. |
| 2021/0106338 A1 | 4/2021 | Gorochow |
| 2021/0128160 A1 | 5/2021 | Li et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0137526 A1 | 5/2021 | Lee et al. |
| 2021/0137529 A1 | 5/2021 | Chen |
| 2021/0137715 A1 | 5/2021 | Ringwala et al. |
| 2021/0145449 A1 | 5/2021 | Gorochow |
| 2021/0153871 A1 | 5/2021 | Griffin |
| 2021/0153872 A1 | 5/2021 | Nguyen et al. |
| 2021/0169495 A1 | 6/2021 | Gorochow et al. |
| 2021/0169496 A1 | 6/2021 | Badruddin et al. |
| 2021/0169498 A1 | 6/2021 | Gorochow |
| 2021/0169499 A1 | 6/2021 | Merritt et al. |
| 2021/0177429 A1 | 6/2021 | Lorenzo |
| 2021/0186518 A1 | 6/2021 | Gorochow et al. |
| 2021/0196284 A1 | 7/2021 | Gorochow et al. |
| 2021/0204955 A1 | 7/2021 | Wallace et al. |
| 2021/0219982 A1 | 7/2021 | Badruddin et al. |
| 2021/0228214 A1 | 7/2021 | Bowman et al. |
| 2021/0244420 A1 | 8/2021 | Aboytes et al. |
| 2021/0251635 A1 | 8/2021 | Soto Del Valle et al. |
| 2021/0259699 A1 | 8/2021 | Rosenbluth et al. |
| 2021/0275184 A1 | 9/2021 | Hewitt et al. |
| 2021/0275187 A1 | 9/2021 | Franano et al. |
| 2021/0275188 A1 | 9/2021 | Plaza et al. |
| 2021/0275779 A1 | 9/2021 | Northrop |
| 2021/0282784 A1 | 9/2021 | Sepetka et al. |
| 2021/0282785 A1 | 9/2021 | Dholakia et al. |
| 2021/0282786 A1 | 9/2021 | Zaidat et al. |
| 2021/0282789 A1 | 9/2021 | Vu et al. |
| 2021/0282944 A1 | 9/2021 | Chen et al. |

OTHER PUBLICATIONS

U.S. Appl. No. 61/866,993, filed Aug. 16, 2013, Hewitt et al.
U.S. Appl. No. 61/979,416, filed Apr. 14, 2014, Hewitt et al.
U.S. Appl. No. 62/093,313, filed Dec. 17, 2014, Hewitt et al.
U.S. Appl. No. 62/307,123, filed Mar. 11, 2016, Plaza et al.
U.S. Appl. No. 62/819,296, filed Mar. 15, 2019, Rangwala et al.

(56) References Cited

OTHER PUBLICATIONS

U.S. Appl. No. 62/819,317, filed Mar. 15, 2019, Dholakia et al.
U.S. Appl. No. 62/873,256, filed Jul. 12, 2019, Milhous et al.

* cited by examiner

ANEURYSM-OCCLUDING MESH RIBBON WITH A SERIES OF LOOPS OR SEGMENTS HAVING DISTAL-TO-PROXIMAL VARIATION IN SIZE, SHAPE, AND/OR ORIENTATION

CROSS-REFERENCE TO RELATED APPLICATIONS

This application is a continuation-in-part of U.S. patent application Ser. No. 17/472,674 filed on 2021 Sep. 12, is a continuation-in-part of U.S. patent application Ser. No. 17/467,680 filed on 2021 Sep. 7, is a continuation-in-part of U.S. patent application Ser. No. 17/466,497 filed on 2021 Sep. 3, is a continuation-in-part of U.S. patent application Ser. No. 17/353,652 filed on 2021 Jun. 21, is a continuation-in-part of U.S. patent application Ser. No. 17/220,002 filed on 2021 Apr. 1, is a continuation-in-part of U.S. patent application Ser. No. 17/214,827 filed on 2021 Mar. 27, is a continuation-in-part of U.S. patent application Ser. No. 17/211,446 filed on 2021 Mar. 24, claims the priority benefit of U.S. provisional patent application 63/119,774 filed on 2020 Dec. 1, is a continuation-in-part of U.S. patent application Ser. No. 16/693,267 filed on 2019 Nov. 23, is a continuation-in-part of U.S. patent application Ser. No. 16/660,929 filed on 2019 Oct. 23, and is a continuation-in-part of U.S. patent application Ser. No. 16/541,241 filed on 2019 Aug. 15.

U.S. patent application Ser. No. 17/220,002 was a continuation-in-part of U.S. patent application Ser. No. 17/214,827 filed on 2021 Mar. 27. U.S. patent application Ser. No. 17/220,002 was a continuation-in-part of U.S. patent application Ser. No. 17/211,446 filed on 2021 Mar. 24. U.S. patent application Ser. No. 17/220,002 claimed the priority benefit of U.S. provisional patent application 63/119,774 filed on 2020 Dec. 1. U.S. patent application Ser. No. 17/220,002 was a continuation-in-part of U.S. patent application Ser. No. 16/693,267 filed on 2019 Nov. 23. U.S. patent application Ser. No. 17/220,002 was a continuation-in-part of U.S. patent application Ser. No. 16/660,929 filed on 2019 Oct. 23.

U.S. patent application Ser. No. 16/693,267 was a continuation-in-part of U.S. patent application Ser. No. 16/660,929 filed on 2019 Oct. 23. U.S. patent application Ser. No. 16/693,267 claimed the priority benefit of U.S. provisional patent application 62/794,609 filed on 2019 Jan. 19. U.S. patent application Ser. No. 16/693,267 claimed the priority benefit of U.S. provisional patent application 62/794,607 filed on 2019 Jan. 19. U.S. patent application Ser. No. 16/693,267 was a continuation-in-part of U.S. patent application Ser. No. 16/541,241 filed on 2019 Aug. 15. U.S. patent application Ser. No. 16/693,267 was a continuation-in-part of U.S. patent application Ser. No. 15/865,822 filed on 2018 Jan. 9 which issued as U.S. patent Ser. No. 10/716,573 on 2020 Jul. 21 U.S. patent application Ser. No. 16/693,267 was a continuation-in-part of U.S. patent application Ser. No. 15/861,482 filed on 2018 Jan. 3.

U.S. patent application Ser. No. 16/660,929 claimed the priority benefit of U.S. provisional patent application 62/794,609 filed on 2019 Jan. 19. U.S. patent application Ser. No. 16/660,929 claimed the priority benefit of U.S. provisional patent application 62/794,607 filed on 2019 Jan. 19. U.S. patent application Ser. No. 16/660,929 was a continuation-in-part of U.S. patent application Ser. No. 16/541,241 filed on 2019 Aug. 15. U.S. patent application Ser. No. 16/660,929 was a continuation-in-part of U.S. patent application Ser. No. 15/865,822 filed on 2018 Jan. 9 which issued as U.S. patent Ser. No. 10/716,573 on 2020 Jul. 21 U.S. patent application Ser. No. 16/660,929 was a continuation-in-part of U.S. patent application Ser. No. 15/861,482 filed on 2018 Jan. 3.

U.S. patent application Ser. No. 16/541,241 claimed the priority benefit of U.S. provisional patent application 62/794,609 filed on 2019 Jan. 19. U.S. patent application Ser. No. 16/541,241 claimed the priority benefit of U.S. provisional patent application 62/794,607 filed on 2019 Jan. 19. U.S. patent application Ser. No. 16/541,241 claimed the priority benefit of U.S. provisional patent application 62/720,173 filed on 2018 Aug. 21. U.S. patent application Ser. No. 16/541,241 was a continuation-in-part of U.S. patent application Ser. No. 15/865,822 filed on 2018 Jan. 9 which issued as U.S. patent Ser. No. 10/716,573 on 2020 Jul. 21

U.S. patent application Ser. No. 15/865,822 claimed the priority benefit of U.S. provisional patent application 62/589,754 filed on 2017 Nov. 22. U.S. patent application Ser. No. 15/865,822 claimed the priority benefit of U.S. provisional patent application 62/472,519 filed on 2017 Mar. 16. U.S. patent application Ser. No. 15/865,822 was a continuation-in-part of U.S. patent application Ser. No. 15/081,909 filed on 2016 Mar. 27. U.S. patent application Ser. No. 15/865,822 was a continuation-in-part of U.S. patent application Ser. No. 14/526,600 filed on 2014 Oct. 29.

U.S. patent application Ser. No. 15/861,482 claimed the priority benefit of U.S. provisional patent application 62/589,754 filed on 2017 Nov. 22. U.S. patent application Ser. No. 15/861,482 claimed the priority benefit of U.S. provisional patent application 62/472,519 filed on 2017 Mar. 16. U.S. patent application Ser. No. 15/861,482 claimed the priority benefit of U.S. provisional patent application 62/444,860 filed on 2017 Jan. 11. U.S. patent application Ser. No. 15/861,482 was a continuation-in-part of U.S. patent application Ser. No. 15/080,915 filed on 2016 Mar. 25 which issued as U.S. patent Ser. No. 10/028,747 on 2018 Jul. 24 U.S. patent application Ser. No. 15/861,482 was a continuation-in-part of U.S. patent application Ser. No. 14/526,600 filed on 2014 Oct. 29.

U.S. patent application Ser. No. 15/081,909 was a continuation-in-part of U.S. patent application Ser. No. 14/526,600 filed on 2014 Oct. 29. U.S. patent application Ser. No. 15/080,915 was a continuation-in-part of U.S. patent application Ser. No. 14/526,600 filed on 2014 Oct. 29. U.S. patent application Ser. No. 14/526,600 claimed the priority benefit of U.S. provisional patent application 61/897,245 filed on 2013 Oct. 30. U.S. patent application Ser. No. 14/526,600 was a continuation-in-part of U.S. patent application Ser. No. 12/989,048 filed on 2010 Oct. 21 which issued as U.S. Pat. No. 8,974,487 on 2015 Mar. 10 U.S. patent application Ser. No. 12/989,048 claimed the priority benefit of U.S. provisional patent application 61/126,047 filed on 2008 May 1. U.S. patent application Ser. No. 12/989,048 claimed the priority benefit of U.S. provisional patent application 61/126,027 filed on 2008 May 1.

The entire contents of these related applications are incorporated herein by reference. Of these, the most directly relevant are U.S. patent application Ser. No. 15/861,482 filed on 2018 Jan. 3, U.S. patent application Ser. No. 15/081,909 filed on 2016 Mar. 27, and U.S. patent application Ser. No. 15/080,915 filed on 2016 Mar. 25 which issued as U.S. patent Ser. No. 10/028,747 on 2018 Jul. 24.

FEDERALLY SPONSORED RESEARCH

Not Applicable

SEQUENCE LISTING OR PROGRAM

Not Applicable

BACKGROUND

Field of Invention

This invention relates to devices and methods for occluding a cerebral aneurysm.

INTRODUCTION

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain. Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm die within one month of the rupture. Sadly, even among those who survive, approximately one-half suffer significant and permanent deterioration of brain function. Better alternatives for cerebral aneurysm treatment are needed.

REVIEW OF THE RELEVANT ART

U.S. patent applications 20120239074 (Aboytes et al., Sep. 20, 2012, "Devices and Methods for the Treatment of Vascular Defects"), 20150209050 (Aboytes et al., Jul. 30, 2015, "Devices and Methods for the Treatment of Vascular Defects"), and 20160262766 (Aboytes et al., Sep. 15, 2016, "Devices and Methods for the Treatment of Vascular Defects") disclose an intrasacular aneurysm occlusion device comprising an expandable implant with a first configuration in which the first portion and the second portion are substantially linearly aligned and a second configuration in which the second portion at least partially overlaps the first portion. U.S. Pat. No. 8,998,947 (Aboytes et al., Apr. 7, 2015, "Devices and Methods for the Treatment of Vascular Defects") discloses an expandable implant with a plurality of flattened, petal-shaped portions.

U.S. patent application 20210169496 (Badruddin et al., Jun. 10, 2021, "System for and Method of Treating Aneurysms") discloses an apparatus with a wire to be advanced within a tube and an occlusion element disposed on the wire, a cover, and an inner anchoring member. U.S. patent applications 20170079661 (Bardsley et al., Mar. 23, 2017, "Occlusive Devices") and 20190269411 (Bardsley et al., Sep. 5, 2019, "Occlusive Devices") and U.S. patent Ser. No. 10/314,593 (Bardsley et al., Jun. 11, 2019, "Occlusive Devices") disclose an implant with a single-layer or dual-layer braided body having a variable porosity. U.S. patent application 20170156733 (Becking et al., Jun. 8, 2017, "Multiple Layer Filamentary Devices for Treatment of Vascular Defects") and U.S. Pat. No. 9,585,669 (Becking et al., Mar. 17, 2017, "Multiple Layer Filamentary Devices for Treatment of Vascular Defects") disclose a self-expanding resilient permeable shell with a proximal end, a distal end, a longitudinal axis, and a plurality of elongate resilient filaments.

U.S. patent Ser. No. 10/980,545 (Bowman et al., Apr. 20, 2021, "Devices for Vascular Occlusion") discloses a braided wire device with a linear compressed shape within a catheter and an expanded state that expands away from an axis of a distal end a delivery pusher in a longitudinally angled and an axially offset manner. U.S. patent application 20210228214 (Bowman et al., Jul. 29, 2021, "Devices for Vascular Occlusion") discloses a mesh neck bridge with an opening. U.S. patent application 20210069387 (Chen et al., Mar. 11, 2021, "Intravascular Devices") discloses an implantable medical device with an elongate member having a cross-sectional dimension that is less than 0.00085 inch. U.S. patent application 20210137529 (Chen, May 13, 2021, "Embolic Devices for Occluding Body Lumens") discloses an elongated member which forms a three-dimensional structure in response to body temperature.

U.S. patent application 20110022149 (Cox et al., Jan. 27, 2011, "Methods and Devices for Treatment of Vascular Defects") discloses an expandable body support structure with first ends secured to a first ring and second ends secured to a second ring. U.S. patent application 20120283768 (Cox et al., Nov. 8, 2012, "Method and Apparatus for the Treatment of Large and Giant Vascular Defects") discloses deployment of multiple permeable shell devices. U.S. patent application 20120165919 (Cox et al., Jun. 28, 2012, "Methods and Devices for Treatment of Vascular Defects") discloses an expandable wire body support structure with a substantially spherical or globular configuration and a portion with low or no porosity. U.S. patent application 20140052233 (Cox et al., Feb. 20, 2014, "Methods and Devices for Treatment of Vascular Defects") discloses a method for treating a cerebral aneurysm by expanding a substantially spherical or globular shell. U.S. provisional patent application 62/819,317 (Dholakia et al., Mar. 15, 2019, "Occlusion") discloses intrasaccular occlusive devices that utilize an apple-core braid winding shape. U.S. patent application 20200289125 (Dholakia et al., Sep. 17, 2020, "Filamentary Devices Having a Flexible Joint for Treatment of Vascular Defects") discloses an implant with first and second permeable shells.

U.S. patent applications 20140135812 (Divino et al., May 15, 2014, "Occlusive Devices"), 20190282242 (Divino et al., Sep. 19, 2019, "Occlusive Devices"), 20190290286 (Divino et al., Sep. 26, 2019, "Occlusive Devices") and 20190343532 (Divino et al., Nov. 14, 2019, "Occlusive Devices") and U.S. patent Ser. No. 10/327,781 (Divino et al., Jun. 25, 2019, "Occlusive Devices") disclose a device with at least one expandable structure adapted to transition from a compressed configuration to an expanded configuration when released into the aneurysm. U.S. patent applications 20150297240 (Divino et al., Oct. 22, 2015, "Embolic Medical Devices") and 20170281194 (Divino et al., Oct. 5, 2017, "Embolic Medical Devices") disclose an intrasacular aneurysm occlusion device with a collapsed configuration in which its first and second side edges are curled toward each other around a longitudinal axis and an expanded configuration forming a series of loops wherein the first and second side edges uncurl.

U.S. patent application 20200155333 (Franano et al., May 21, 2020, "Ballstent Device and Methods of Use") discloses a rounded, thin-walled, expandable metal structure ("ballstent"). U.S. patent Ser. No. 11/013,516 (Franano et al., May 25, 2021, "Expandable Body Device and Method of Use") discloses a single-lobed, thin-walled, expandable body ("ballstent" or "blockstent") and a flexible, elongated delivery device ("delivery catheter"). U.S. patent Ser. No. 11/033,275 (Franano et al., Jun. 15, 2021, "Expandable Body Device and Method of Use") discloses hollow gold structures that can be folded, wrapped, compressed, advanced to a location in the body of patient, and expanded by injection of a fluid.

U.S. patent application 20210085333 (Gorochow et al., Mar. 25, 2021, "Inverting Braided Aneurysm Treatment System and Method") discloses a tubular braid with an open end, a pinched end, and a predetermined shape. U.S. patent application 20210145449 (Gorochow, May 20, 2021, "Implant Delivery System with Braid Cup Formation") discloses an implant system with an engagement wire, a pull wire, and a braided implant having a distal ring thereon. U.S. patent application 20210169498 (Gorochow, Jun. 10, 2021, "Delivery of Embolic Braid") discloses a method for a braided implant with a band attached to a delivery tube. U.S. patent Ser. No. 11/051,825 (Gorochow, Jul. 6, 2021, "Delivery System for Embolic Braid") discloses a braided implant attached to a releasing component that can be detachably engaged with a delivery tube and a pull wire. U.S. patent application 20210169495 (Gorochow et al., Jun. 10, 2021, "Intrasaccular Inverting Braid with Highly Flexible Fill Material") discloses a tubular braided implant including a braid that can be delivered as a single layer braid, invert into itself during deployment to form at least two nested sacks and an additional braid material that can fill the innermost sack.

U.S. patent application 20210186518 (Gorochow et al., Jun. 24, 2021, "Implant Having an Intrasaccular Section and Intravascular Section") discloses a tubular braid with an intrasaccular section, an intravascular section, a pinched section, and a predetermined shape. U.S. patent application 20210196284 (Gorochow et al., Jul. 1, 2021, "Folded Aneurysm Treatment Device and Delivery Method") and U.S. patent Ser. No. 11/076,861 (Gorochow et al., Aug. 3, 2021, "Folded Aneurysm Treatment Device and Delivery Method") disclose a device with a braided implant within an aneurysm sack such that an outer non-inverted layer contacts a wall of the aneurysm and an inverted layer apposes the outer non-inverted layer to form a double layer of braid across a neck of the aneurysm. U.S. patent Ser. No. 11/058,430 (Gorochow et al., Jul. 13, 2021, "Aneurysm Device and Delivery System") discloses a braided device with a proximal expandable portion for sealing an aneurysm neck and a distal expandable portion.

U.S. patent application 20190216467 (Goyal, Jul. 18, 2019, "Apparatus and Methods for Intravascular Treatment of Aneurysms") discloses a device with a first portion having an expandable and compressible mesh for expansion against the wall of an aneurysm and a second disk portion covering an outside of the neck opening. U.S. patent application 20180070955 (Greene et al., Mar. 15, 2018, "Embolic Containment") discloses a method of treating a neurovascular arteriovenous malformation comprising a catheter with a mesh catch structure on the distal portion of the catheter, wherein the catheter is configured to deliver liquid embolic and dimethyl sulfoxide. U.S. patent Ser. No. 10/426,486 (Guo et al., Oct. 1, 2019, "Vaso-Occlusive Device Delivery System") discloses a vaso-occlusive device delivery assembly with a pusher assembly.

U.S. patent applications 20150313605 (Griffin, Nov. 5, 2015, "Occlusion Device"), 20190053810 (Griffin, Feb. 21, 2019, "Occlusion Device"), 20190059909 (Griffin, Feb. 28, 2019, "Occlusion Device"), 20200038035 (Griffin, Feb. 6, 2020, "Occlusion Device"), and 20210068842 (Griffin, Mar. 11, 2021, "Occlusion Device") and also U.S. patent Ser. No. 10/130,372 (Griffin, Nov. 20, 2018, "Occlusion Device") disclose an occlusion device with a substantially solid marker with a distal end and a low profile resilient mesh body which is attached to the distal end. U.S. patent applications 20170156734 (Griffin, Jun. 8, 2017, "Occlusion Device") and 20190269414 (Griffin, Sep. 5, 2019, "Occlusion Device") and U.S. patent Ser. No. 10/285,711 (Griffin, May 14, 2019, "Occlusion Device") disclose an occlusion device comprising a continuous compressible mesh structure comprising axial mesh carriages configured end to end, wherein each end of each carriage is a pinch point in the continuous mesh structure. U.S. patent Ser. No. 10/869,672 (Griffin, Dec. 22, 2020, "Occlusion Device") discloses an occlusion device with a dual layer of mesh and an inverted mushroom shape. U.S. patent application 20210153871 (Griffin, May 27, 2021, "Occlusion Device") discloses a continuous mesh structure comprising a medial pinch point.

U.S. patent application 20140358178 (Hewitt et al., Dec. 4, 2014, "Filamentary Devices for Treatment of Vascular Defects") discloses a resilient self-expanding permeable shell with at least 40% composite filaments relative to a total number of filaments, wherein composite filaments comprise a high strength material and a highly radiopaque material. U.S. patent application 20160249934 (Hewitt et al., Sep. 1, 2016, "Filamentary Devices for Treatment of Vascular Defects") discloses a woven braided mesh having variable mesh density. U.S. patent application 20160249935 (Hewitt et al., Sep. 1, 2016, "Devices for Therapeutic Vascular Procedures") discloses an expandable cylindrical structure made of wires and a self-expanding permeable shell at the distal end of the cylindrical structure. U.S. patent application 20160367260 (Hewitt et al., Dec. 22, 2016, "Devices for Therapeutic Vascular Procedures") and U.S. Pat. No. 9,629,635 (Hewitt et al., Apr. 25, 2017, "Devices for Therapeutic Vascular Procedures") disclose an expandable structure with distal and proximal permeable shells having different pore sizes.

U.S. patent application 20170095254 (Hewitt et al., May 6, 2017, "Filamentary Devices for Treatment of Vascular Defects") discloses an aneurysm occlusion device comprising a self-expanding permeable shell having a radially constrained elongated state configured for delivery within a catheter lumen, an expanded state with a globular and longitudinally shortened configuration relative to the radially constrained state, and a plurality of elongate filaments that are woven together, which define a cavity of the permeable shell. U.S. patent application 20170128077 (Hewitt et al., May 11, 2017, "Devices for Therapeutic Vascular Procedures") discloses a self-expanding resilient permeable shell with a metallic coil secured at a distal end. U.S. patent application 20190223881 (Hewitt et al., Jul. 25, 2019, "Devices for Therapeutic Vascular Procedures") discloses a self-expanding resilient permeable shell whose filaments have a distal region that extends beyond the distal end of the permeable shell and forms an extension having a generally-circular shape.

U.S. patent application 20210106337 (Hewitt et al., Apr. 15, 2021, "Filamentary Devices for Treatment of Vascular Defects") discloses a resilient self-expanding permeable implant with an expanded state with a longitudinally shortened configuration. U.S. patent applications 20160249935 (Hewitt et al., Sep. 1, 2016, "Devices for Therapeutic Vascular Procedures") and 20160367260 (Hewitt et al., Dec. 22, 2016, "Devices for Therapeutic Vascular Procedures") disclose an intrasacular aneurysm occlusion device comprising a distal self-expanding resilient permeable shell, a proximal self-expanding resilient permeable shell, and an elongate support member between the distal and proximal permeable shells. U.S. patent applications 20180206849 (Hewitt et al., Jul. 26, 2018, "Filamentary Devices for the Treatment of Vascular Defects") and 20200289126 (Hewitt et al., Sep. 17, 2020, "Filamentary Devices for Treatment of Vascular Defects") and U.S. Pat. No. 9,955,976 (Hewitt et al., May 1, 2018, "Filamentary Devices for Treatment of Vascular Defects") and 10939914 (Hewitt et al., Mar. 9, 2021, "Filamentary Devices for the Treatment of Vascular Defects") disclose mesh balls with different layers and areas with different porosities.

U.S. provisional patent application 61/866,993 (Hewitt et al., Aug. 16, 2013, "Filamentary Devices for Treatment of Vascular Defects") discloses a self-expanding resilient permeable structure wherein at least some elongate filaments include highly radiopaque material. U.S. provisional patent application 61/979,416 (Hewitt et al, Apr. 14, 2014, "Devices for Therapeutic Vascular Procedures") discloses a self-expanding resilient permeable shell with a plurality of elongate resilient filaments having a variable braided structure. U.S. provisional patent application 62/093,313 (Hewitt et al., Dec. 17, 2014, "Devices for Therapeutic Vascular Procedures") discloses a self-expanding resilient permeable shell with elongate resilient filaments having a variable braided structure, wherein a distal portion has a first braid density, a proximal portion has a second braid density, and the second braid density is greater than the first braid density.

U.S. provisional patent application 61/483,032 (Kent et al., May 5, 2011, "Method and Apparatus for the Treatment of Large and Giant Vascular Defects") discloses various self-expanding shells, including some with double shells and layers. U.S. patent application 20210137526 (Lee et al., May 13, 2021, "Embolic Devices for Occluding Body Lumens") discloses an embolic device, wherein a cavity of a first three-dimensional structure is configured to accommodate a second three-dimensional structure. U.S. patent application 20210128169 (Li et al., May 6, 2021, "Devices, Systems, and Methods for Treatment of Intracranial Aneurysms") discloses systems and methods for treating an aneurysm including intravascularly delivering an occlusive member to an aneurysm cavity and deforming a shape of the occlusive member via introduction of an embolic element to a space between the occlusive member and an inner surface of the aneurysm wall.

U.S. patent application 20210007755 (Lorenzo et al., Jan. 14, 2021, "Intrasaccular Aneurysm Treatment Device With Varying Coatings") discloses an implant with a braided mesh movable from a delivery configuration having a single-layer tubular shape to an implanted configuration sized to be implanted in an aneurysm sac. U.S. patent Ser. No. 10/905,430 (Lorenzo et al., Feb. 2, 2021, "Aneurysm Device and Delivery System") discloses a braided device with inner and outer meshes. U.S. patent Ser. No. 10/716,574 (Lorenzo et al., Jul. 21, 2020, "Aneurysm Device and Delivery Method") discloses a self-expanding braided device with an inverted outer occlusive sack. U.S. patent applications 20150272589 (Lorenzo, Oct. 1, 2015, "Aneurysm Occlusion Device") and 20190008522 (Lorenzo, Jan. 10, 2019, "Aneurysm Occlusion Device") disclose a device with a control ring having a substantially annular body disposed on the proximal end region to prevent radial expansion of the proximal end region and to provide an engagement feature during manipulation of the occlusion device.

U.S. patent application 20200375606 (Lorenzo, Dec. 3, 2020, "Aneurysm Method and System") discloses a self-expanding braided implant with a distal implant end and a proximal implant end, the braided implant being invertible about the distal implant end. U.S. patent application 20210177429 (Lorenzo, Jun. 17, 2021, "Aneurysm Method and System") discloses a vaso-occlusive device with at least two nested sacks. U.S. patent Ser. No. 11/076,860 (Lorenzo, Aug. 3, 2021, "Aneurysm Occlusion Device") discloses a tubular structure having a proximal end region and a distal end region, having an expanded condition and a collapsed condition.

U.S. patent application 20180000489 (Marchand et al., Jan. 4, 2018, "Filamentary Devices for Treatment of Vascular Defects") and U.S. patent Ser. No. 10/610,231 (Marchand et al., Apr. 7, 2020, "Filamentary Devices for Treatment of Vascular Defects") disclose a self-expanding resilient permeable shell wherein a ratio of the total cross-sectional area of small filaments to the total cross-sectional area of large filaments is between 0.56 and 1.89. U.S. patent application 20160249937 (Marchand et al., Sep. 1, 2016, "Multiple Layer Filamentary Devices for Treatment of Vascular Defects") discloses an occlusion device with a number of undulations. U.S. patent application 20200281603 (Marchand et al., Sep. 10, 2020, "Filamentary Devices for Treatment of Vascular Defects") discloses a permeable shell with a swellable polymer. U.S. patent application 20130245667 (Marchand et al., Sep. 19, 2013, "Filamentary Devices and Treatment of Vascular Defects") discloses a self-expanding resilient permeable shell with filaments which are bundled and secured to each other at a proximal end.

U.S. patent applications 20180271540 (Merritt et al., Sep. 27, 2018, "Systems and Methods for Embolization of Body Structures") and 20210169499 (Merritt et al., Jun. 10, 2021, "Systems and Methods for Embolization of Body Structures") disclose a self-expanding permeable shell with a plurality of circumferentially-arrayed lobes. U.S. patent application 20210007754 (Milhous et al., Jan. 14, 2021, "Filamentary Devices for Treatment of Vascular Defects") discloses inner and outer mesh balls. U.S. provisional patent application 62/873,256 (Milhous et al., Jul. 12, 2019, "Devices for Treatment of Vascular Defects") discloses a mesh of braided wires gathered into retention structures at proximal and distal ends. U.S. patent application 20190254676 (Murphy et al., Aug. 22, 2019, "Vaso-Occlusive Device and Delivery Assembly") discloses a vaso-occlusive treatment system with a delivery assembly.

U.S. patent application 20210129275 (Nguyen et al., May 6, 2021, "Devices, Systems, and Methods for Treating Aneurysms") discloses a method of everting a mesh such that the mesh encloses an open volume with a shape based, at least in part, on the shape of a forming assembly. U.S. patent application 20210128168 (Nguyen et al., May 6, 2021, "Systems and Methods for Treating Aneurysms") discloses a treatment system with an electrolytically corrodible conduit having a proximal portion, a distal portion, and a detachment zone between the proximal portion and the distal portion. U.S. patent applications 20210128167 (Patel et al., May 6, 2021, "Systems and Methods for Treating Aneurysms") and 20210128160 (Li et al., May 6, 2021, "Systems and Methods for Treating Aneurysms") disclose the use of an occlusive member (e.g., an expandable braid) in conjunction with an embolic element (e.g., coils, embolic material).

U.S. patent Ser. No. 11/058,431 (Pereira et al., Jul. 13, 2021, "Systems and Methods for Treating Aneurysms") discloses an occlusion element having a distal end, a proximal end, and a longitudinal axis extending between the distal end and the proximal end, the occlusion element configured to be delivered in a collapsed configuration and further configured to expand to an expanded configuration, and the occlusion element comprising an inverted mesh tube having an outer layer and an inner layer. U.S. provisional patent application 62/307,123 (Plaza et al, Mar. 11, 2016, "Systems and Methods for Delivery of Stents and Stent-like Devices") appears to disclose an expanding aneurysm occlusion device which is implantable within the parent vessel of an aneurysm. U.S. patent application 20170258473 (Plaza et al., Sep. 14, 2017, "Systems and Methods for Delivery of Stents and Stent-Like Devices") and U.S. patent Ser. No. 10/952,739 (Plaza et al., Mar. 23, 2021, "Systems and Methods for Delivery of Stents and Stent-Like Devices") disclose an expandable elongate tubular member.

U.S. patent applications 20060155323 (Porter et al., Jul. 13, 2006, "Intra-Aneurysm Devices") and 20190298379 (Porter et al., Oct. 3, 2019, "Intra-Aneurysm Devices") and U.S. patent Ser. No. 10/265,075 (Porter et al., Apr. 23, 2019, "Intra-Aneurysm Devices") disclose a self-expanding resilient body having a linear configuration for deployment through a delivery catheter and an expanded substantially-spherical deployed configuration. U.S. patent application 20210052279 (Porter et al., Feb. 25, 2021, "Intra-Aneurysm Devices") discloses a device with an upper member that sits against the dome of an aneurysm, a lower member that sits in the neck of the aneurysm, and a means of adjusting the overall dimensions of the device.

U.S. patent application 20170189035 (Porter, Jul. 6, 2017, "Embolic Devices and Methods of Manufacturing Same") discloses an intrasacular aneurysm occlusion device comprising a flat embolic braid having a first side comprising a first side surface and a second side comprising a second side surface facing in an opposite direction than the first side surface, the braid having an elongated constrained configuration for being deployed through a delivery catheter, and a three-dimensional unconstrained configuration, wherein in the three-dimensional unconstrained configuration, the braid assumes a plurality of successive loops in which the braid is at least partially twisted between successive loops of the plurality, so that the first side surface faces externally of each loop, and the second side surface faces an interior of each loop, respectively, regardless of a change in direction and/or orientation of the braid. U.S. patent application 20200367901 (Porter et al., Nov. 26, 2020, "Embolic Devices and Methods of Manufacturing Same") discloses an embolic braid which is twisted between successive loops.

U.S. patent application 20180092690 (Priya et al., Apr. 5, 2018, "Customized Endovascular Devices and Methods Pertaining Thereto") discloses patient-specific 3D complex coils and methods of making such coils, including custom fixtures for the manufacture of such coils. U.S. patent application 20210128165 (Pulugurtha et al., May 6, 2021, "Systems and Methods for Treating Aneurysms") discloses an occlusive member configured to be positioned within an aneurysm sac, and a distal conduit coupled to the occlusive member and having a first lumen extending therethrough. U.S. provisional patent application 62/819,296 (Rangwala et al, Mar. 15, 2019, "Occlusion") discloses an intrasaccular occlusive device with a more flexible distal section and a more stiff proximal section. U.S. patent application 20200289124 (Rangwala et al., Sep. 17, 2020, "Filamentary Devices for Treatment of Vascular Defects") discloses a permeable implant with a stiffer proximal portion near the neck of an aneurysm.

U.S. patent application 20170079662 (Rhee et al., Mar. 23, 2017, "Occlusive Devices") discloses an aneurysm occlusion device comprising frame and mesh components, wherein the frame and mesh components have different porosity levels. U.S. patent applications 20210128162 (Rhee et al., May 6, 2021, "Devices, Systems, and Methods for Treatment of Intracranial Aneurysms") and 20210153872 (Nguyen et al., May 27, 2021, "Devices, Systems, and Methods for Treatment of Intracranial Aneurysms") disclose delivering an occlusive member to an aneurysm cavity via an elongated shaft and transforming a shape of the occlusive member within the cavity and introducing an embolic element to a space between the occlusive member and an inner surface of the aneurysm wall.

U.S. patent application 20180303486 (Rosenbluth et al., Oct. 25, 2018, "Embolic Occlusion Device and Method") discloses an occlusion device including a tubular braided member with a repeating pattern of larger diameter portions and smaller diameter portions along a longitudinal axis. U.S. patent application 20160022445 (Ruvalcaba et al., Jan. 28, 2016, "Occlusive Device") and 20190343664 (Ruvalcaba et al., Nov. 14, 2019, "Occlusive Device") disclose an aneurysm embolization device can with a body having a single, continuous piece of material that is shape set into a plurality of distinct structural components and an atraumatic tip portion, U.S. Pat. No. 8,597,320 (Sepetka et al., Dec. 3, 2013, "Devices and Methods for Treating Vascular Malformations") discloses a device with a closed mesh structure with a proximal collar and a distal collar, with flexible filaments extending therebetween. U.S. patent application 20190274691 (Sepetka et al., Sep. 12, 2019, "Occlusive Device") and U.S. patent Ser. No. 11/045,203 (Sepetka et al., Jun. 29, 2021, "Occlusive Device") disclose multiple sequentially deployed occlusive devices that are connected together to create an extended length.

U.S. patent Ser. No. 10/729,447 (Shimizu et al., Aug. 4, 2020, "Devices for Vascular Occlusion") discloses a wide variety of occlusive devices, delivery systems, and manufacturing methods for such devices. U.S. patent applications 20200375607 (Soto Del Valle et al., Dec. 3, 2020, "Aneurysm Device and Delivery System") and 20200397447 (Lorenzo et al., Dec. 24, 2020, "Aneurysm Device and Delivery System") disclose a mesh ball in a mesh bowl. U.S. patent application 20170354418 (Teoh et al., Dec. 14, 2017, "Vaso-Occlusive Device Delivery System") discloses a vaso-occlusive device delivery assembly with a pusher assembly, a conductive sacrificial link, and a vaso-occlusive device secured to the pusher assembly by the sacrificial link.

U.S. patent application 20170086851 (Wallace et al., Mar. 30, 2017, "Vaso-Occlusive Devices and Methods of Use") discloses expandable vaso-occlusive implants that include one or more soft and expandable braided members coupled to a pushable member such as a coil that may be inserted and retrieved from within an aneurism using a delivery catheter. U.S. patent applications 20180250013 (Wallace et al., Sep. 6, 2018, "Vaso-Occlusive Devices Including a Friction Element") and 20200360025 (Wallace et al., Nov. 19, 2020, "Vaso-Occlusive Devices Including a Friction Element") disclose vaso-occlusive implants with one or more soft and expandable braided members coupled to a pushable member such as a coil. U.S. patent applications 20190201000 (Wallace et al., Jul. 4, 2019, "Vaso-Occlusive Devices") and 20210204955 (Wallace et al., Jul. 8, 2021, "Vaso-Occlusive Devices"), and also U.S. patent Ser. No. 10/925,612 (Wallace et al., Feb. 23, 2021, "Vaso-Occlusive Devices") disclose a vaso-occlusion system for occluding an aneurysm including a delivery catheter with a delivery lumen extending therethrough, a pusher member at least partially extending through the delivery lumen, and a vaso-occlusive device loaded within the delivery lumen. U.S. patent Ser. No. 10/383,635 (Wallace et al., Aug. 20, 2019, "Vaso-Occlusive Devices and Methods of Use") and U.S. patent application 20190374228 (Wallace et al., Dec. 12, 2019, "Vaso-Occlusive Devices and Methods of Use") disclose vaso-occlusive implants that include one or more soft and expandable braided member coupled to a pushable member such as a coil.

U.S. patent application 20200187952 (Walsh et al., Jun. 18, 2020, "Intrasaccular Flow Diverter for Treating Cerebral Aneurysms") discloses implants with a stabilizing frame for anchoring and an occluding element for diverting blood flow from an aneurysm neck. U.S. patent application 20200405347 (Walzman, Dec. 31, 2020, "Mesh Cap for Ameliorating Outpouchings") discloses a self-expandable occluding device can both cover the neck of an outpouching and serve as a permanent embolic plug thereby immediately stabilizing the outpouching. U.S. patent Ser. No. 10/398,441 (Warner et al., Sep. 3, 2019, "Vascular Occlusion") discloses a vascular disorder treatment system comprising a delivery tube, a containment device, a pusher distally movable through a lumen, and a stopper ring. U.S. patent application 20210045750 (Wolf et al., Feb. 18, 2021, "Systems and Methods for Treating Aneurysms") and U.S. patent Ser. No. 10/856,880 (Badruddin et al., Dec. 8, 2020, "Systems and Methods for Treating Aneurysms") discloses an implantable vaso-occlusive device with a proximal end configured to seat against the aneurysm adjacent the neck of the aneurysm and a distal end configured to extend in the sac and away from the neck of the aneurysm.

SUMMARY OF THE INVENTION

This invention is an intrasacular aneurysm occlusion device with a longitudinal mesh ribbon having a distal-to-proximal series of loops or segments which is inserted into an aneurysm sac, wherein the longitudinal mesh ribbon accumulates and overlaps onto itself to form an arcuate three-dimensional occlusive mass in the aneurysm sac, and wherein there is distal-to-proximal variation in the sizes, shapes, orientations, and/or other characteristics of the loops or segments in the distal-to-proximal series of loops or segments. For example, loops or segments in the distal-to-proximal series of loops or segments can be progressively smaller in size and/or progressively more curved (e.g. more concave or convex) as one views the series in a distal-to-proximal direction.

As this series of loops or segments accumulates and overlaps in the aneurysm sac, the variation in sizes, shapes, orientations, or other characteristics of the loops or segments can enable the three dimensional mass which is formed in the aneurysm sac to occlude the sac more densely, cover the aneurysm neck more completely, and conform to the wall contours of the sac more closely. It can be desirable to have proximal-to-distal variation in loops or segments with respect to their size, shape, inter-loop connection angle, degree of curvature, stiffness, flexibility, porosity, and/or elasticity.

In an example, a longitudinal mesh ribbon can be pre-formed with distal-to-proximal variation in the sizes, shapes, orientations, or other characteristics of the loops or segments before the ribbon is deployed into an aneurysm sac. Alternatively, a device may enable a user to selectively and remotely change the relative sizes, shapes, orientations, or other characteristics of proximal and distal loops or segments in a ribbon as the ribbon is being deployed into an aneurysm sac. In this manner, a user can bend, curve, steer, and/or extend loops or segments in real time as they are inserted into the aneurysm to create a more-effective arcuate three-dimensional occlusive mass in the aneurysm sac.

BRIEF INTRODUCTION TO THE FIGURES

DETAILED DESCRIPTION OF THE FIGURES

Figure 1:
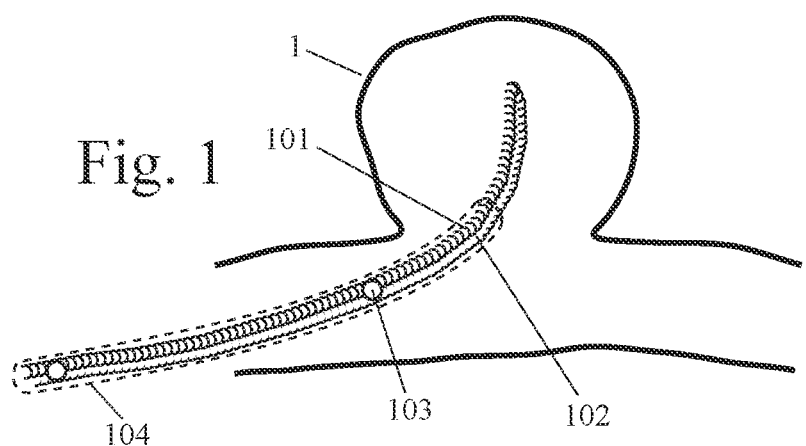
FIGS. 1 through 3 show an intrasacular aneurysm occlusion device with a series of connected wire loops.

In an example, an intrasacular aneurysm occlusion device can comprise: a longitudinal mesh ribbon with a distal-to-proximal series of loops or segments which is inserted into an aneurysm sac; wherein the ribbon accumulates and overlaps onto itself to form an arcuate three-dimensional occlusive mass in the aneurysm sac; and wherein a plurality of loops or segments in the distal-to-proximal series of loops or segments are progressively smaller in size as one views the series in a distal-to-proximal direction.

In an example, the plurality of loops or segments can include at least three loops or segments which are progressively smaller in size as one views them in a distal-to-proximal direction. In an example, the plurality of loops or segments can include at least five loops or segments which are progressively smaller in size as one views them in a distal-to-proximal direction. In an example, the plurality of loops or segments can be progressively smaller in length as one views them in a distal-to-proximal direction. In an example, the plurality of loops or segments can be progressively smaller in width as one views them in a distal-to-proximal direction. In an example, the longitudinal mesh ribbon can be a flattened tubular mesh.

In an example, an intrasacular aneurysm occlusion device can comprise: a longitudinal mesh ribbon with a distal-to-proximal series of loops or segments which is inserted into an aneurysm sac; wherein the ribbon accumulates and overlaps onto itself to form an arcuate three-dimensional occlusive mass in the aneurysm sac; and wherein a plurality of loops or segments in the distal-to-proximal series of loops or segments are connected by progressively smaller inter-loop connection angles and/or are progressively more curved as one views them in a distal-to-proximal direction.

In an example, the plurality of loops or segments can include at least three loops or segments which are connected by progressively smaller inter-loop connection angles and/or are progressively more curved as one views them in a distal-to-proximal direction. In an example, the plurality of loops or segments can include at least five loops or segments which are connected by progressively smaller inter-loop connection angles and/or are progressively more curved as one views them in a distal-to-proximal direction. In an example, the plurality of loops or segments can be connected by progressively smaller inter-loop connection angles as one views them in a distal-to-proximal direction. In an example, the plurality of loops or segments can be progressively more curved as one views them in a distal-to-proximal direction, wherein more curved means more concave or more convex. In an example, the longitudinal mesh ribbon can be a flattened tubular mesh.

In an example, an intrasacular aneurysm occlusion device can comprise: a longitudinal mesh ribbon with a distal-to-proximal series of loops or segments which is inserted into an aneurysm sac; wherein the ribbon accumulates and overlaps onto itself to form an arcuate three-dimensional occlusive mass in the aneurysm sac; wherein a first loop or segment in the series of loops or segments has a first length, width, inter-loop connection angle, and/or level of curvature; wherein a second loop or segment in the series of loops or segments has a second length, width, inter-loop connection angle, and/or level of curvature; and wherein a user of the device can selectively and remotely change the first size, shape, inter-loop connection angle, and/or level of curvature relative to the second length, width, inter-loop connection angle, and/or level of curvature during deployment of the ribbon into the aneurysm sac.

In an example, the device can further comprise an electromagnetic energy emitter which the user of the device uses to selectively and remotely change the first size, shape, inter-loop connection angle, and/or level of curvature relative to the second length, width, inter-loop connection angle, and/or level of curvature by applying electromagnetic energy to the ribbon. In an example, the user can bend, curve, and/or steer loops or segments in the ribbon by applying electromagnetic energy to the ribbon. In an example, the user can bend, curve, and/or steer one or more loops or segments in a first direction by applying electromagnetic energy to a first portion of the ribbon and can bend, curve, and/or steer the one or more loops or segments in a second direction by applying electromagnetic energy to a second portion of the ribbon.

In an example, the device further can comprise a wire or cord which the user of the device moves to selectively change the first size, shape, inter-loop connection angle, and/or level of curvature relative to the second length, width, inter-loop connection angle, and/or level of curvature. In an example, the user can bend, curve, and/or steer loops or segments of the ribbon by moving a wire or cord which is attached to the ribbon. In an example, the user can bend, curve, and/or steer one or more loops or segments in a first direction by moving a cord or wire attached to the ribbon in a first manner and can bend, curve, and/or steer the one or more loops or segments in a second direction by moving a cord or wire in a second manner, wherein the first and/or second manner are selected from the group consisting of: pulling a cord, pulling a wire, pushing a wire, and rotating a wire. In an example, the user can bend, curve, and/or steer one or more loops or segments in a first direction by moving a first cord or wire attached to the ribbon and can bend, curve, and/or steer the one or more loops or segments in a second direction by moving a second cord or wire attached to the ribbon.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes one or more of the loops or segments to bend or curve, thereby enabling the device user to steer loops or segments during deployment of the device. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes a second (more proximal) loop or segment to become more curved (e.g. more concave or convex) than a first (more distal) loop or segment.

In another embodiment, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to become more curved (e.g. more concave or convex). In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to become longer.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes a second (more proximal) loop or segment to become larger than a first (more distal) loop or segment. Alternatively, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; a first pull wire (or cord) which is connected to a first portion of the ribbon; and a second pull wire (or cord) which is connected to a second portion of the ribbon; wherein movement (e.g. pulling, pushing, or rotation) of the first pull wire bends or curves one or more loops or segments in a first direction; and wherein movement (e.g. pulling, pushing, or rotation) of the second pull wire bends or curves the one or more loops or segments in a second direction.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes one or more of the loops or segments to become shorter. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy changes the connection angles between one or more pairs of loops or segments.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes a second (more proximal) loop or segment to become shorter than a first (more distal) loop or segment. Alternatively, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; a first pull wire (or cord) which is connected to a first portion of the ribbon; and a second pull wire (or cord) which is connected to a second portion of the ribbon; wherein movement (e.g. pulling, pushing, or rotation) of the first pull wire bends or curves one or more loops or segments in a first direction; and wherein movement (e.g. pulling, pushing, or rotation) of the second pull wire bends or curves the one or more loops or segments in a second direction, thereby enabling the device user to steer loops or segments during deployment of the device.

In another embodiment, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes a second (more proximal) loop or segment to become longer than a first (more distal) loop or segment. In another example, an intrasacular aneurysm occlusion device can comprise: a longitudinal mesh ribbon with a distal-to-proximal series of loops or segments which is inserted into an aneurysm sac; wherein the ribbon accumulates and overlaps onto itself to form an arcuate three-dimensional occlusive mass in the aneurysm sac; and wherein a plurality of loops or segments in the distal-to-proximal series of loops or segments are progressively smaller in size as one views the series in a distal-to-proximal direction.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes a second (more proximal) loop or segment to become more flexible (and/or less stiff) than a first (more distal) loop or segment. In another example, an intrasacular aneurysm occlusion device can comprise: a longitudinal mesh ribbon with a distal-to-proximal series of loops or segments which is inserted into an aneurysm sac; wherein the ribbon accumulates and overlaps onto itself to form an arcuate three-dimensional occlusive mass in the aneurysm sac; and wherein a plurality of loops or segments in the distal-to-proximal series of loops or segments are connected by progressively smaller inter-loop connection angles and/or are progressively more curved as one views them in a distal-to-proximal direction.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes one or more of the loops or segments to become less dense and/or more porous. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes a second (more proximal) loop or segment to become shorter than a first (more distal) loop or segment.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes a second (more proximal) loop or segment to become more curved (e.g. more concave or convex) than a first (more distal) loop or segment.

In an example, an intrasacular aneurysm occlusion device can comprise: a longitudinal mesh ribbon with a distal-to-proximal series of loops or segments which is inserted into an aneurysm sac; wherein the ribbon accumulates and overlaps onto itself to form an arcuate three-dimensional occlusive mass in the aneurysm sac; wherein a first loop or segment in the series of loops or segments has a first length, width, inter-loop connection angle, and/or level of curvature; wherein a second loop or segment in the series of loops or segments has a second length, width, inter-loop connection angle, and/or level of curvature; and wherein a user of the device can selectively and remotely change the first size, shape, inter-loop connection angle, and/or level of curvature relative to the second length, width, inter-loop connection angle, and/or level of curvature during deployment of the ribbon into the aneurysm sac.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes a second (more proximal) loop or segment to become less dense and/or more porous than a first (more distal) loop or segment. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to become smaller.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to bend or curve relative to the longitudinal axis of the mesh ribbon. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to become less dense and/or more porous.

In another embodiment, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes one or more of the loops or segments to bend or curve relative to the longitudinal axis of the ribbon. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes a second (more proximal) loop or segment to become longer than a first (more distal) loop or segment.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes one or more of the loops or segments to bend or curve. Alternatively, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes a second (more proximal) loop or segment to become more flexible (and/or less stiff) than a first (more distal) loop or segment.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes one or more of the loops or segments to become smaller. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to bend or curve.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord)

which is connected to the ribbon, wherein movement (e.g. pulling, pushing, or rotation) of the wire during deployment of the device causes one or more of the loops or segments to become longer. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon, wherein delivery of electromagnetic energy to a first portion of the ribbon causes one or more loops or segments to bend or curve in a first direction, and wherein delivery of electromagnetic energy to a second portion of the ribbon causes the one or more loops or segments to bend or curve in a second direction, thereby enabling the device user to steer loops or segments during deployment of the device.

In another embodiment, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes a second (more proximal) loop or segment to become smaller than a first (more distal) loop or segment. Alternatively, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes a second (more proximal) loop or segment to become less dense and/or more porous than a first (more distal) loop or segment.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes one or more of the loops or segments to become more flexible (and/or less stiff). In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon, wherein delivery of a first pattern of electromagnetic energy to the ribbon causes one or more loops or segments to bend or curve in a first direction, and wherein delivery of a second pattern of electromagnetic energy to the ribbon causes the one or more loops or segments to bend or curve in a second direction, thereby enabling the device user to steer loops or segments during deployment of the device.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device changes the connection angles between one or more pairs of loops or segments. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes a second (more proximal) loop or segment to become larger than a first (more distal) loop or segment.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to become more flexible (and/or less stiff). In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g. pulling, pushing, or rotation) of the wire during deployment of the device causes one or more of the loops or segments to become larger.

In another embodiment, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to bend or curve, thereby enabling the device user to steer loops or segments during deployment of the device. Alternatively, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to become shorter.

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and a pull wire (or cord) which is connected to the ribbon, wherein movement (e.g.

pulling, pushing, or rotation) of the wire during deployment of the device causes one or more of the loops or segments to become more curved (e.g. more concave or convex).

In an example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes a second (more proximal) loop or segment to become smaller than a first (more distal) loop or segment. In another example, an intrasacular aneurysm occlusion device can comprise: a longitudinal mesh ribbon with a distal-to-proximal series of loops or segments which is inserted into an aneurysm sac, wherein the ribbon accumulates and overlaps onto itself to form an arcuate three-dimensional occlusive mass in the aneurysm sac; and an electromagnetic energy emitter which delivers electromagnetic energy to the ribbon while the ribbon is being deployed into the aneurysm sac, wherein the delivery of electromagnetic energy causes one or more of the loops or segments to become larger.

Figure 2:
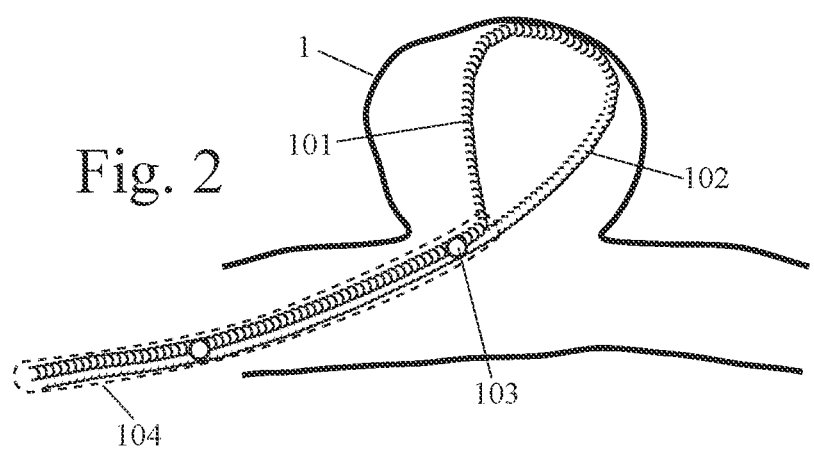
Figure 3:
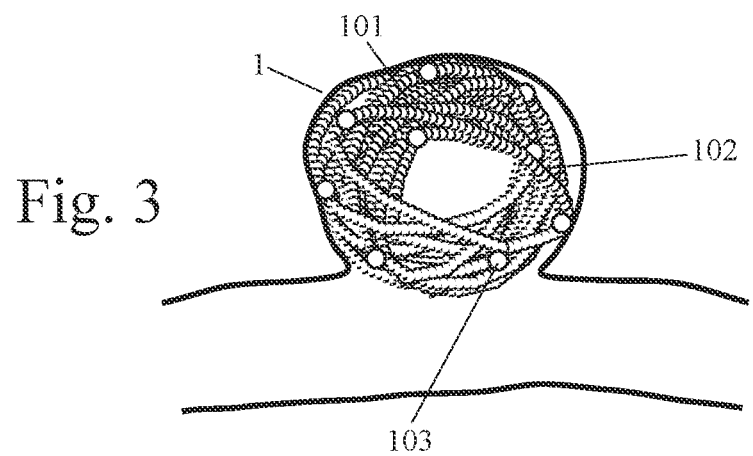

FIGS. 1 through 3 show an example of a device to occlude an aneurysm comprising: (a) a first longitudinal section of a flexible longitudinal embolic member that is configured to be inserted into an aneurysm; (b) a second longitudinal section of a flexible longitudinal embolic member that is configured to be inserted into the aneurysm; (c) a plurality of connections between the first and second longitudinal sections, wherein these connections connect the first and second longitudinal sections at a plurality of selected locations along their longitudinal axes; and (d) a longitudinal lumen that is configured to be inserted into a blood vessel, wherein the first and second longitudinal sections travel through the lumen in order to be inserted into the aneurysm; wherein at least portions of the first and second longitudinal sections are configured in parallel within the lumen; wherein portions of the first and second longitudinal sections which are not connected by connections move apart from each other after exiting the lumen and the connections move closer to each other after exiting the lumen in order to form a plurality of loops within the aneurysm; wherein part of the perimeter of a loop is comprised of a portion of the first longitudinal section and part of the perimeter of a loop is comprised of a portion of the second longitudinal section; wherein a loop has a contiguous 360-degree perimeter with ends which are connected to each other; and wherein loops are interconnected at the connections.

FIGS. 1 through 3 also show an example of a device to occlude an aneurysm comprising: (a) a longitudinal lumen that is configured to be inserted into a blood vessel, wherein this blood vessel is the parent vessel from which an aneurysm has formed; (b) a first flexible longitudinal embolic member that is configured to travel through the longitudinal lumen and be inserted into the aneurysm sac; (c) a second flexible longitudinal embolic member that is configured to travel through the longitudinal lumen and be inserted into the aneurysm sac; wherein the longitudinal axes of the first and second flexible longitudinal embolic members are substantially parallel as these flexible longitudinal embolic members travel through the longitudinal lumen; and (d) a plurality of connections which connect the first and second flexible longitudinal embolic members at a plurality of locations along the lengths of the flexible longitudinal embolic members; wherein the segments of the first and second flexible longitudinal embolic members that are not connected by the connections move away from each other after they exit the longitudinal lumen, thereby forming loops within the aneurysm sac; wherein these loops are connected by the connections; and wherein accumulation of these loops within the aneurysm sac substantially occludes the aneurysm.

In an example, a longitudinal lumen can be a removable catheter. In an example, flexible longitudinal embolic members can be coils. In an example, connections can connect flexible longitudinal embolic members at uniformly-spaced locations along their lengths so as to form equal-size loops within the aneurysm sac and wherein these equal-size loops substantially span the circumference of the aneurysm sac. In an example, connections can connect flexible longitudinal embolic members at uniformly-spaced locations along their lengths so as to form equal-size loops within the aneurysm sac and these equal-size loops substantially span the circumference of the aneurysm sac without protruding into the parent vessel. In an example, connections can connect flexible longitudinal embolic members at non-uniformly-spaced locations along their lengths so as to form loops of different sizes within the aneurysm sac and these different size loops substantially occlude the interior as well as the circumference of the aneurysm sac.

We now discuss the specific components of FIGS. 1 through 3 in detail. FIGS. 1 through 3 show three sequential views of the same example of a device and method to occlude an aneurysm. To provide anatomical context, FIG. 1 shows a longitudinal cross-sectional view of an aneurysm sac 1 which has formed on a longitudinal blood vessel. FIG. 1 also shows an occlusive device comprising: a longitudinal lumen 104 that has been inserted into the longitudinal blood vessel; a first flexible longitudinal embolic member 101 that travels through lumen 104 into aneurysm sac 1; a second flexible longitudinal embolic member 102 that travels through lumen 104 into aneurysm sac 1; and a plurality of connections (including 103) which connect first and second embolic members 101 and 102 at a plurality of locations along their longitudinal lengths. In this example, flexible longitudinal embolic members 101 and 102 are two different segments (or sides) of the same continuous flexible longitudinal embolic member. In this example, this continuous member has two parallel segments or sides (comprising flexible longitudinal embolic members 101 and 102) within longitudinal lumen 104. In another example, embolic member 101 and embolic 102 can be different embolic members that are connected in some other manner at their distal ends.

In this example, flexible longitudinal embolic members 101 and 102 are substantially parallel as they travel through longitudinal lumen 104. However, as shown in FIG. 2, portions of embolic members 101 and 102 which are not connected to each other separate from each other after they exit longitudinal lumen 104 within aneurysm sac 1. In an example, this separation can be partly caused by pressure from contact with the wall of aneurysm sac 1. In an example, this separation can be partly caused by embolic members 101 and 102 having a shape memory with a shape that is restored after these embolic members exit longitudinal lumen 104. In the example that is shown in FIGS. 1 and 2, segments of embolic members 101 and 102 which are not connected by connections (such as 103) move away from each other after they exit longitudinal lumen 104.

FIG. 3 shows the accumulation of a plurality of interconnected, contiguous loops within aneurysm sac 1 as flexible longitudinal embolic members 101 and 102 continue to be pushed into aneurysm sac 1. These loops are pair-wise connected to each other by the plurality of connections (including connection 103). As shown in FIG. 3, accumulation of this plurality of loops within aneurysm sac 1 forms an embolic mass which substantially occludes the aneurysm. In this example, the interconnected and contiguous nature of these loops helps to prevent loops from prolapsing out of aneurysm sac 1 into the parent blood vessel. This can result in less prolapse of coils into the parent vessel than is the case with coils in the prior art which disperse and accumulate in a free-form spiraling manner within the aneurysm sac. Also, FIG. 3 shows longitudinal lumen 104 as having been removed.

In the example shown in FIGS. 1 through 3, the connections (such as 103) between embolic members 101 and 102 are relatively evenly-spaced along the longitudinal lengths of embolic members 101 and 102. In an example, the spacing of these connections can be selected for a specific aneurysm with a specific size and shape in order to most efficiently occlude that specific aneurysm. In an example, the spacing of connections can differ between devices which are configured to occlude narrow-neck aneurysms and devices which are configured to occlude wide-neck aneurysms. In an example, the spacing of these connections can be pre-selected to vary along the length of embolic members 101 and 102 in order to most efficiently occlude an aneurysm at different times or stages during the occlusion procedure. For example, connections can be separated by longer distances at the most distal portions of embolic members 101 and 102 and become progressively shorter at more proximal portions of embolic members 101 and 102. In an example, the most distal connections can be spaced to form loops which span the entire circumference of the aneurysm sac but successive loops can become smaller and smaller to better fill the central space of the aneurysm sac. Relevant design variations discussed elsewhere in this disclosure or in priority-linked disclosures can also be applied to the example shown here.

Figure 4:
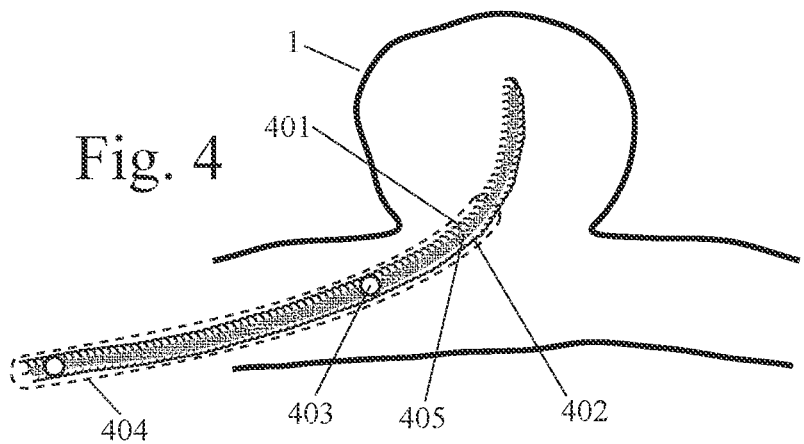
FIGS. 4 through 6 show an intrasacular aneurysm occlusion device with a series of connected mesh-filled wire loops.
Figure 5:
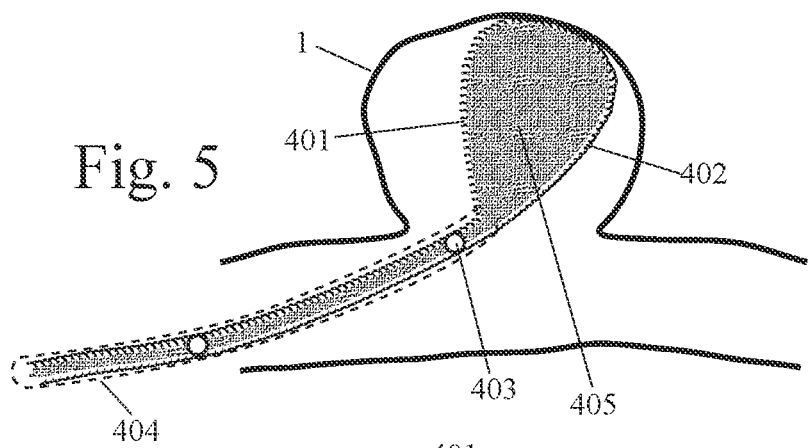
Figure 6:
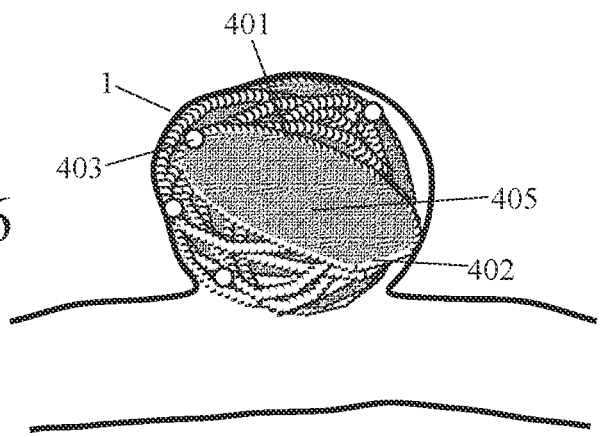

FIGS. 4 through 6 show another example of a device and method to occlude an aneurysm which is like the example shown in FIGS. 1 through 3, except that there is also a stretchable mesh within the loops. FIGS. 4 through 6 show three sequential views of a device and method to occlude an aneurysm which can be described as embolic coils which form interconnected contiguous loops within an aneurysm sac, wherein the interiors of these loops are spanned by a stretchable mesh.

More specifically, FIGS. 4 through 6 show an example of a device to occlude an aneurysm comprising: (a) a first longitudinal section of a flexible longitudinal embolic member that is configured to be inserted into an aneurysm; (b) a second longitudinal section of a flexible longitudinal embolic member that is configured to be inserted into the aneurysm; (c) a stretchable mesh which spans between the first and second longitudinal sections; (d) a plurality of connections between the first and second longitudinal sections, wherein these connections connect the first and second longitudinal sections at a plurality of selected locations along their longitudinal axes; and (e) a longitudinal lumen that is configured to be inserted into a blood vessel; wherein the first and second longitudinal sections travel through the lumen in order to be inserted into the aneurysm; wherein at least portions of the first and second longitudinal sections are configured in parallel within the lumen; wherein portions of the first and second longitudinal sections which are not connected by connections move apart from each other after exiting the lumen and connections move closer to each other after exiting the lumen in order to form a plurality of loops within the aneurysm; wherein part of the perimeter of a loop is comprised of a portion of the first longitudinal section and part of the perimeter of a loop is comprised of a portion of the second longitudinal section; wherein a loop has a contiguous 360-degree perimeter with ends which are connected to each other; and wherein loops are interconnected at the connections.

FIGS. 4 through 6 also show an example of a device to occlude an aneurysm comprising: (a) a flexible longitudinal lumen that is configured to be inserted into a blood vessel, wherein this blood vessel is the parent vessel from which an aneurysm has formed; (b) a first flexible longitudinal embolic member that is configured to travel through the flexible longitudinal lumen and be inserted into the aneurysm sac; (c) a second flexible longitudinal embolic member that is configured to travel through the flexible longitudinal lumen and be inserted into the aneurysm sac; wherein the flexible longitudinal axes of the first and second longitudinal embolic members are substantially parallel as these longitudinal embolic members travel through the flexible longitudinal lumen; (d) a stretchable mesh which spans between the first and second flexible longitudinal sections; and (e) a plurality of connections which connect the first and second longitudinal embolic members at a plurality of locations along the lengths of the longitudinal embolic members; wherein the segments of the first and second longitudinal embolic members that are not connected by the connections move away from each other after they exit the flexible longitudinal lumen, thereby forming loops within the aneurysm sac; wherein these loops are connected by the connections; and wherein accumulation of these loops and the stretchable mesh within the aneurysm sac substantially occludes the aneurysm.

In an example, a longitudinal lumen can be a removable catheter. In an example, flexible longitudinal embolic members can be coils. In an example, connections can connect flexible longitudinal embolic members at uniformly-spaced locations along their lengths so as to form equal-size loops within the aneurysm sac and wherein these equal-size loops substantially span the circumference of the aneurysm sac. In an example, connections can connect flexible longitudinal embolic members at uniformly-spaced locations along their lengths so as to form equal-size loops within the aneurysm sac and these equal-size loops substantially span the circumference of the aneurysm sac without protruding into the parent vessel. In an example, connections can connect flexible longitudinal embolic members at non-uniformly-spaced locations along their lengths so as to form loops of different sizes within the aneurysm sac and these different size loops substantially occlude the interior as well as the circumference of the aneurysm sac. In an example, the embolic members can criss-cross each other at their connections, wherein the embolic members switch sides from one loop to the next. In an example, sinusoidal embolic members can criss-cross each other at their connections, wherein the embolic members switch sides from one loop to the next.

In an example, a stretchable mesh can be an elastic mesh. In an example, a stretchable mesh can be made from a polymer. In an example, a stretchable mesh can be made from metal. In an example, a stretchable mesh can be attached to the first and second flexible longitudinal embolic members. In an example, a stretchable mesh can loop around the first and second flexible longitudinal embolic members. In an example, a stretchable mesh can span the entire interiors of loops. In an example, a stretchable mesh can span at least 50% of the interiors of loops. In an example, a stretchable mesh can be impermeable to blood flow. In an example, a stretchable mesh can resist blood flow.

We now discuss the specific components of FIGS. 4 through 6 in detail. FIGS. 4 through 6 show three sequential views of the same example of a device and method to occlude an aneurysm. To provide anatomical context, FIG. 4 shows a longitudinal cross-sectional view of an aneurysm sac 1 which has formed on a longitudinal blood vessel. FIG. 4 also shows an occlusive device comprising: a longitudinal lumen 404 that has been inserted into the longitudinal blood vessel; a first flexible longitudinal embolic member 401 that travels through lumen 404 into aneurysm sac 1; a second flexible longitudinal embolic member 402 that travels through lumen 404 into aneurysm sac 1; a stretchable mesh 405 which spans between first flexible longitudinal embolic member 401 and second flexible longitudinal embolic member 402; and a plurality of connections (including 403) which connect first and second flexible longitudinal embolic members 401 and 402 at a plurality of locations along their longitudinal lengths. In this example, flexible longitudinal embolic members 401 and 402 are two different segments (or sides) of the same continuous embolic member. In this example, this continuous embolic member has two parallel segments or sides (comprising flexible longitudinal embolic members 401 and 402) within longitudinal lumen 404. In another example, flexible longitudinal embolic member 401 and flexible longitudinal embolic member 402 can be different flexible longitudinal embolic members that are connected in some other manner at their distal ends.

In this example, flexible longitudinal embolic members 401 and 402 are substantially parallel as they travel through longitudinal lumen 404. However, as shown in FIG. 5, portions of flexible longitudinal embolic members 401 and 402 which are not connected to each other separate from each other after they exit longitudinal lumen 404 within aneurysm sac 1. In an example, this separation can be partly caused by pressure from contact with the wall of aneurysm sac 1. In an example, this separation can be partly caused by flexible longitudinal embolic members 401 and 402 having a shape memory with a shape that is restored after these embolic members exit longitudinal lumen 404. In the example that is shown in FIGS. 1 and 2, segments of flexible longitudinal embolic members 401 and 402 which are not connected by connections (such as 403) move away from each other after they exit longitudinal lumen 404.

FIG. 6 shows the accumulation of a plurality of interconnected, contiguous loops within aneurysm sac 1 as flexible longitudinal embolic members 401 and 402 continue to be pushed into aneurysm sac 1. These loops are pair-wise connected to each other by the plurality of connections (including connection 403). As shown in FIG. 6, the stretchable mesh stretches to span the arcuate interiors of these loops. As shown in FIG. 6, accumulation of this plurality of loops and the stretchable mesh within aneurysm sac 1 forms an embolic coil-and-mesh mass (such as a coil-and-mesh ball) which substantially occludes the aneurysm. In this example, the interconnected and contiguous nature of these loops helps to prevent loops from prolapsing out of aneurysm sac 1 into the parent blood vessel. This can result in less prolapse of coils into the parent vessel than is the case with coils in the prior art which disperse and accumulate in a free-form spiraling manner within the aneurysm sac. Also, FIG. 6 shows longitudinal lumen 404 as having been removed.

In the example shown in FIGS. 4 through 6, the connections (such as 403) between embolic members 401 and 402 are relatively evenly-spaced along the longitudinal lengths of embolic members 401 and 402. In an example, the spacing of these connections can be selected for a specific aneurysm with a specific size and shape in order to most efficiently occlude that specific aneurysm. In an example, the spacing of connections can differ between devices which are configured to occlude narrow-neck aneurysms and devices which are configured to occlude wide-neck aneurysms. In an example, the spacing of these connections can be pre-selected to vary along the length of embolic members 401 and 402 in order to most efficiently occlude an aneurysm at different times or stages during the occlusion procedure. For example, connections can be separated by longer distances at the most distal portions of embolic members 401 and 402 and become progressively shorter at more proximal portions of embolic members 401 and 402. In an example, the most distal connections can be spaced to form loops which span the entire circumference of the aneurysm sac but successive loops can become smaller and smaller to better fill the central space of the aneurysm sac. In an example, connections which connect flexible longitudinal embolic members can be at non-uniform distances along their lengths in order to better occlude an aneurysm sac.

In an example, the device shown in FIGS. 4 through 6 can be described as a device to occlude an aneurysm comprising a series of proximally-and-distally-connected mesh-filled loops. In an example, the device shown in FIGS. 4 through 6 can be described as a device to occlude an aneurysm comprising a series of proximally-and-distally-connected mesh-filled loops which overlap within an aneurysm sac to create a coil-and-mesh mass (such as a coil-and-mesh ball). In an example, the device shown in FIGS. 4 through 6 can be described as a device to occlude an aneurysm comprising a series of proximally-and-distally-connected mesh-filled loops whose sides are relatively parallel as they travel through a lumen and whose sides become concave after they exit the lumen into an aneurysm sac in order to create a coil-and-mesh mass (such as a coil-and-mesh ball).

In an example, FIGS. 4 though 6 show a device for occluding an aneurysm comprising: a catheter; a first segment of a longitudinal embolic coil; a second segment of a longitudinal embolic coil, wherein the first and second segments are connected to each other at a proximal location along their length and are connected to each other at a distal location along their length, wherein the first and second segments have a first configuration when they are within the catheter, wherein there is a first average distance between the first and second segments when they are in the first configuration, wherein the first and second segments have a second configuration after they exit the catheter into an aneurysm sac, wherein there is a second average distance between the first and second segments when they are in the second configuration, and wherein the second distance is greater than the first distance; and a stretchable mesh which spans between the first and second segments.

In an example, FIGS. 4 though 6 show a device for occluding an aneurysm comprising: a catheter; a first longitudinal embolic coil; a second longitudinal embolic coil, wherein the first and second longitudinal embolic coils are connected to each other at a plurality of locations along their lengths, forming a plurality of loops whose sides comprise segments of the first longitudinal embolic coil and segments of the second longitudinal embolic coil, wherein the first and second longitudinal embolic coils have a first configuration when they are within the catheter and a second configuration after they exit the catheter into an aneurysm sac, wherein the sides of the loops are further apart in the second configuration than in the first configuration; and a stretchable mesh which spans the interiors of the loops between the first and second longitudinal embolic coils. Relevant design variations discussed elsewhere in this disclosure or in priority-linked disclosures can also be applied to the example shown here.

Figure 7:
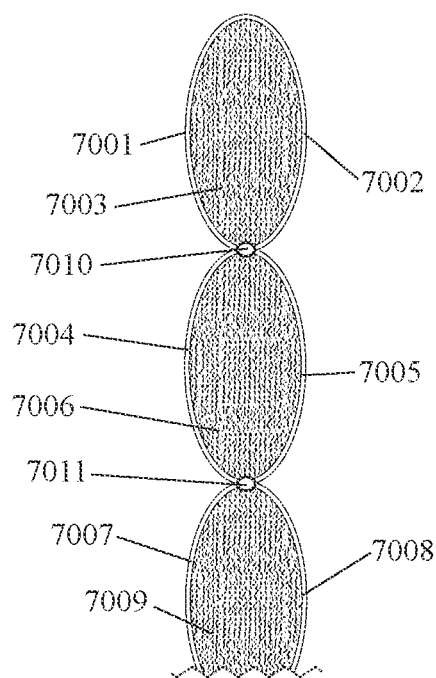
FIG. 7 shows an intrasacular aneurysm occlusion device with mesh-filled loops formed by intersecting or overlapping first and second wires.

FIG. 7 shows an example of an aneurysm occlusion device with a plurality of connected longitudinal segments. Each longitudinal segment has a first longitudinal wire which forms one side of the segment, a second longitudinal wire which forms the opposite side of the segment, and an inner mesh which spans between the first and second wires. In this example, the first and second wires in a segment combine to form an oval or elliptical loop. This example also shows connectors between segments.

Specifically, FIG. 7 shows an aneurysm occlusion device with a plurality of longitudinal segments, three of which are shown here. Each of the three segments has a first longitudinal wire (7001, 7004, and 7007, respectively), a second longitudinal wire (7002, 7005, and 7008, respectively), and an inner mesh (7003, 7006, and 7009, respectively) which spans between the first and second wires. This example also includes connectors 7010 and 7011 between segments. Example variations and descriptions discussed elsewhere in this disclosure or in priority-linked disclosures can be applied to this example, but are not repeated here in order to reduce redundancy.

Figure 8:
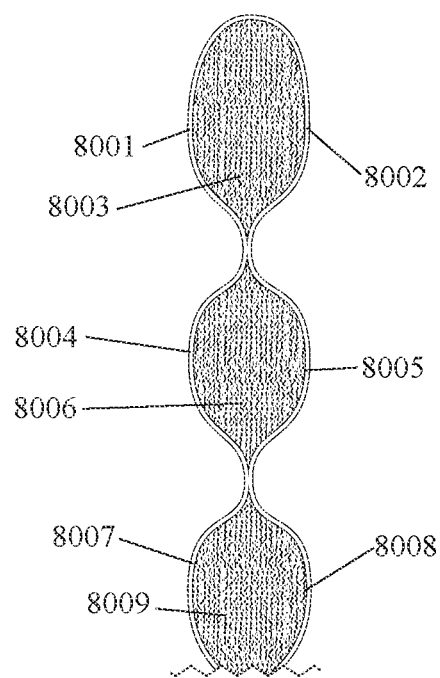
FIG. 8 shows an intrasacular aneurysm occlusion device with mesh-filled loops formed by converging and diverging first and second wires.

FIG. 8 shows an example of an aneurysm occlusion device with a plurality of connected longitudinal segments. Each longitudinal segment has a first longitudinal wire which forms one side of the segment, a second longitudinal wire which forms the opposite side of the segment, and an inner mesh which spans between the first and second wires. In this example, the same continuous first longitudinal wire spans the same side of each of the segments and the same continuous second longitudinal wire spans the opposite side of each of the segments. In this example, the longitudinal segments are shaped like flower petals.

Specifically, FIG. 8 shows an aneurysm occlusion device with a plurality of petal-shaped longitudinal segments, three of which are shown here. Each of the three segments has a first longitudinal wire (8001, 8004, and 8007, respectively), a second longitudinal wire (8002, 8005, and 8008, respectively), and an inner mesh (8003, 8006, and 8009, respectively) which spans between the first and second wires. In this example, the same continuous first longitudinal wire spans the same side of each of the three segments and the same continuous second longitudinal wire spans the opposite side of each of the three segments. In an example, a first longitudinal wire can span alternating (e.g. right vs. left) sides in a sequence of segments and a second longitudinal wire can span alternating (e.g. left vs. right) sides in the sequence of segments. In an example, different segments can have separate wires. Example variations and descriptions discussed elsewhere in this disclosure or in priority-linked disclosures can be applied to this example, but are not repeated here in order to reduce redundancy.

Figure 9:
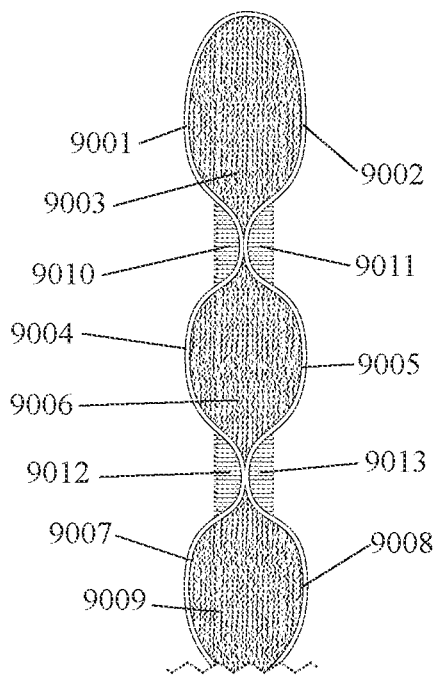
FIG. 9 shows an intrasacular aneurysm occlusion device with mesh-filled loops which are bilaterally connected by elastic material.

FIG. 9 shows an example of an aneurysm occlusion device with a plurality of connected longitudinal segments. Each longitudinal segment has a first longitudinal wire which forms one side of the segment, a second longitudinal wire which forms the opposite side of the segment, and a mesh which spans between the first and second wires. In this example, the same continuous first longitudinal wire spans the same side of each of the segments and the same continuous second longitudinal wire spans the opposite side of each of the segments. In this example, the longitudinal segments are shaped like flower petals. This example also includes left-side and right-side elastic connectors between segments.

Specifically, FIG. 9 shows an aneurysm occlusion device with a plurality of petal-shaped longitudinal segments, three of which are shown here. Each of the three segments has a first longitudinal wire (9001, 9004, and 9007, respectively), a second longitudinal wire (9002, 9005, and 9008, respectively), and an inner mesh (9003, 9006, and 9009, respectively) which spans between the first and second wires. This example also includes left-side and right-side elastic connectors (9010, 9011, 9012, and 9013) between segments. In an example, a first side connector (such as 9010) can have a first level of elasticity or flexibility, an opposite side connector (such as 9011) can have a second level of elasticity flexibility, and the first level can be different than the second level. In an example, differences in elasticity or flexibility between (left-side vs. right-side) connectors can bias the longitudinal axis of connected segments into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 10:
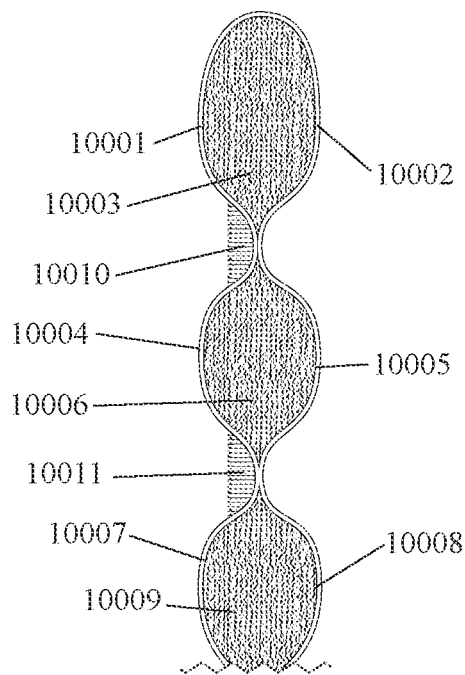
FIG. 10 shows an intrasacular aneurysm occlusion device with mesh-filled loops which are unilaterally connected by elastic material.

FIG. 10 shows an example of an aneurysm occlusion device that is similar to the one shown in FIG. 9 except that it has longitudinally asymmetric (one side only) elastic connectors between segments. Specifically, FIG. 10 shows an aneurysm occlusion device with a plurality of petal-shaped longitudinal segments, three of which are shown here. Each of the three segments has a first longitudinal wire (10001, 10004, and 10007, respectively), a second longitudinal wire (10002, 10005, and 10008, respectively), and an inner mesh (10003, 10006, and 10009, respectively) which spans between the first and second wires. This example also includes left-side-only elastic connectors (10010 and 10011) between segments. In an example, such longitudinally-asymmetric (e.g. left-side only) connectors can bias the longitudinal axis of connected segments into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 11:
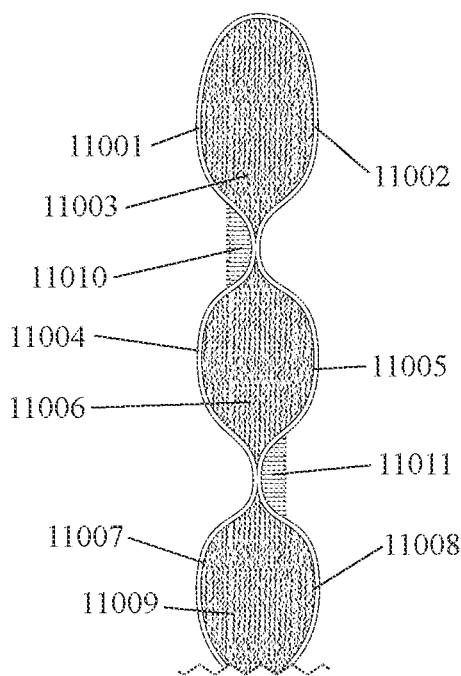
FIG. 11 shows an intrasacular aneurysm occlusion device with mesh-filled loops which are connected on alternating sides by elastic material.

FIG. 11 shows an example of an aneurysm occlusion device that is similar to the one shown in FIG. 9 except that it has longitudinally asymmetric (alternating side) elastic connectors between segments. Specifically, FIG. 11 shows an aneurysm occlusion device with a plurality of petal-shaped longitudinal segments, three of which are shown here. Each of the three segments has a first longitudinal wire (11001, 11004, and 11007, respectively), a second longitudinal wire (11002, 11005, and 11008, respectively), and an inner mesh (11003, 11006, and 11009, respectively) which spans between the first and second wires. This example also includes alternating (e.g. left vs. right) side elastic connectors (11010 and 11011) between segments. In an example, such longitudinally-asymmetric (alternating side) connectors can bias the longitudinal axis of connected segments into curvature in a first direction and then in a second direction as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 12:
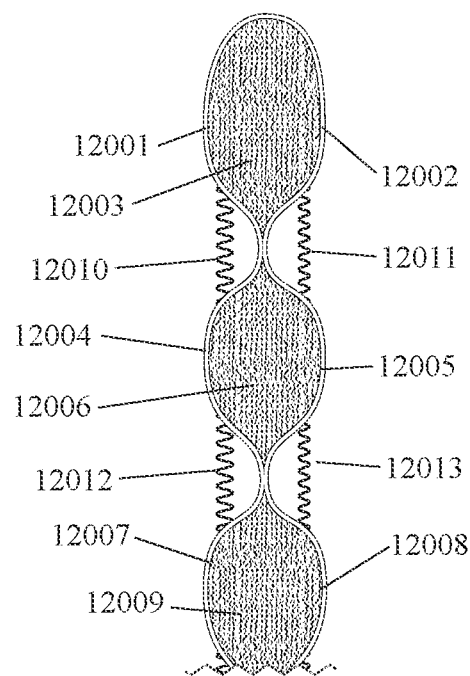
FIG. 12 shows an intrasacular aneurysm occlusion device with mesh-filled loops which are bilaterally connected by springs.

FIG. 12 shows an example of an aneurysm occlusion device with a plurality of connected petal-shaped longitudinal segments. Each longitudinal segment has a first longitudinal wire which forms one side of the segment, a second longitudinal wire which forms the opposite side of the segment, and a mesh which spans between the first and second wires. This example also includes left-side and right-side spring connectors between segments.

Specifically, FIG. 12 shows an aneurysm occlusion device with a plurality of petal-shaped longitudinal segments, three of which are shown here. Each of the three segments has a first longitudinal wire (12001, 12004, and 12007, respectively), a second longitudinal wire (12002, 12005, and 12008, respectively), and an inner mesh (12003, 12006, and 12009, respectively) which spans between the first and second wires. This example also includes left-side and right-side spring connectors (12010, 12011, 12012, and 12013) between segments. In an example, a first side spring (such as 12010) can have a first level of elasticity or tensile strength, an opposite side spring (such as 12011) can have a second level of elasticity or tensile strength, and the first level can be different than the second level. In an example, differences in elasticity or tensile strength between (left-side vs. right-side) springs can bias the longitudinal axis of connected segments into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 13:
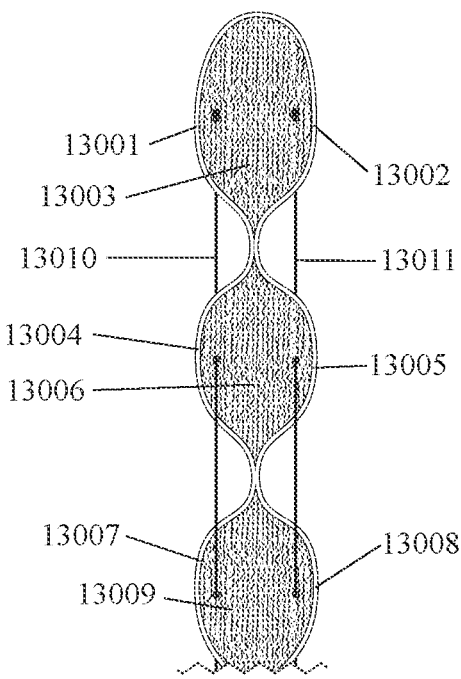
FIG. 13 shows a first intrasacular aneurysm occlusion device with mesh-filled loops which are bilaterally connected by pull cords.

FIG. 13 shows an example of an aneurysm occlusion device with a plurality of connected petal-shaped longitudinal segments. Each longitudinal segment has a first longitudinal wire which forms one side of the segment, a second longitudinal wire which forms the opposite side of the segment, and a mesh which spans between the first and second wires. This example also includes left-side and right-side pull-cords which span and connect segments.

Specifically, FIG. 13 shows an aneurysm occlusion device with a plurality of petal-shaped longitudinal segments, three of which are shown here. Each of the three segments has a first longitudinal wire (13001, 13004, and 13007, respectively), a second longitudinal wire (13002, 13005, and 13008, respectively), and an inner mesh (13003, 13006, and 13009, respectively) which spans between the first and second wires. This example also includes left-side and right-side pull-cords (13010 and 13011) which span and connect segments. In an example, when a user pulls on a pull-cord, it pulls longitudinal segments closer together. In this example, pulling on pull-cords draws segments together in an alternating side (e.g. zigzag) manner. In an example, differential pulling on left-side vs. right-side pull-cords can bias the longitudinal axis of connected segments into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 14:
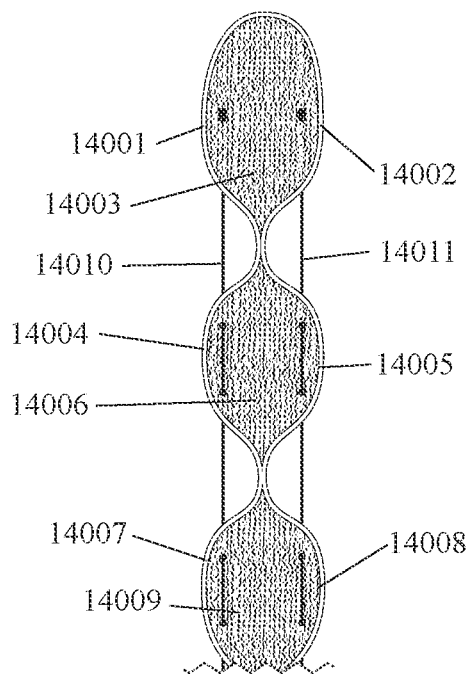
FIG. 14 shows a second intrasacular aneurysm occlusion device with mesh-filled loops which are bilaterally connected by pull cords.

FIG. 14 shows an example of an aneurysm occlusion device like the one in FIG. 13 except that pulling on pull-cords draws segments together in a same-side (spiral) manner. Specifically, FIG. 14 shows an aneurysm occlusion device with a plurality of petal-shaped longitudinal segments, three of which are shown here. Each of the three segments has a first longitudinal wire (14001, 14004, and 14007, respectively), a second longitudinal wire (14002, 14005, and 14008, respectively), and an inner mesh (14003, 14006, and 14009, respectively) which spans between the first and second wires. This example also includes left-side and right-side pull-cords (14010 and 14011) which span and connect segments. In this example, pulling on pull-cords draws segments together in a same-side (e.g. spiral) manner. In an example, differential pulling on left-side vs. right-side pull-cords can bias the longitudinal axis of connected segments into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 15:
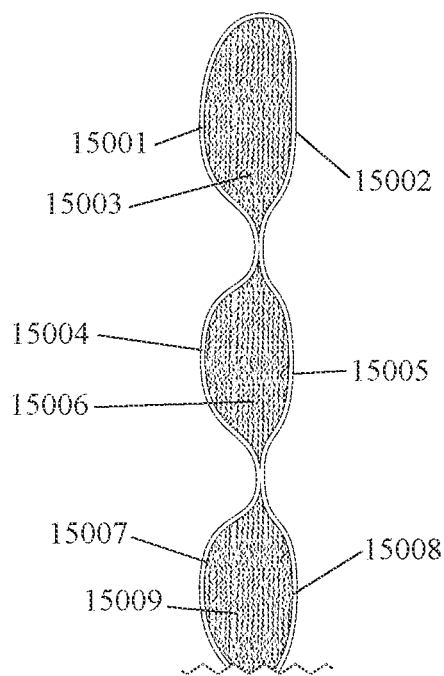
FIG. 15 shows an intrasacular aneurysm occlusion device with asymmetric undulating mesh-filled loops.

FIG. 15 shows an example of an aneurysm occlusion device with a plurality of connected longitudinal segments. Each longitudinal segment has a first longitudinal wire which forms one side of the segment, a second longitudinal wire which forms the opposite side of the segment, and a mesh which spans between the first and second wires. In this example, the longitudinal segments are geometrically-asymmetric with respect to their longitudinal axes, but each have the same shape and orientation.

Specifically, FIG. 15 shows an aneurysm occlusion device with a plurality of longitudinal segments which are geometrically-asymmetric with respect to their longitudinal axes. Three segments are shown here. Each of the three segments has a first longitudinal wire (15001, 15004, and 15007, respectively), a second longitudinal wire (15002, 15005, and 15008, respectively), and an inner mesh (15003, 15006, and 15009, respectively) which spans between the first and second wires. In this example, the three segments each have the same shape and orientation. The geometric-asymmetry of these segments with respect to their common longitudinal axis can bias this longitudinal axis into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 16:
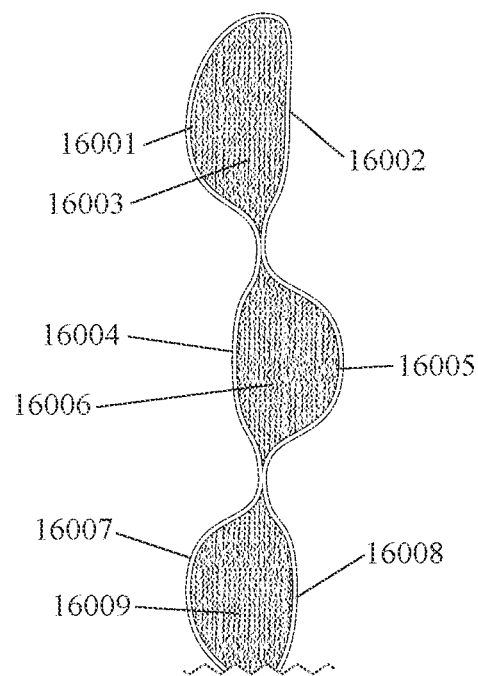
FIG. 16 shows an intrasacular aneurysm occlusion device with alternating asymmetric undulating mesh-filled loops.

FIG. 16 shows an example of an aneurysm occlusion device with a plurality of connected longitudinal segments. Each longitudinal segment has a first longitudinal wire which forms one side of the segment, a second longitudinal wire which forms the opposite side of the segment, and a mesh which spans between the first and second wires. In this example, the longitudinal segments are geometrically-asymmetric with respect to their longitudinal axes. The segments each have the same shape, but differ in orientation.

Specifically, FIG. 16 shows an aneurysm occlusion device with a plurality of longitudinal segments which are geometrically-asymmetric with respect to their longitudinal axes. Three segments are shown here. Each of the three segments has a first longitudinal wire (16001, 16004, and 16007, respectively), a second longitudinal wire (16002, 16005, and 16008, respectively), and an inner mesh (16003, 16006, and 16009, respectively) which spans between the first and second wires. In this example, the three segments each have the same shape, but differ in orientation. The geometric-asymmetry of these segments with respect to their longitudinal axes and their differences in orientation can bias their common longitudinal axis into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 17:
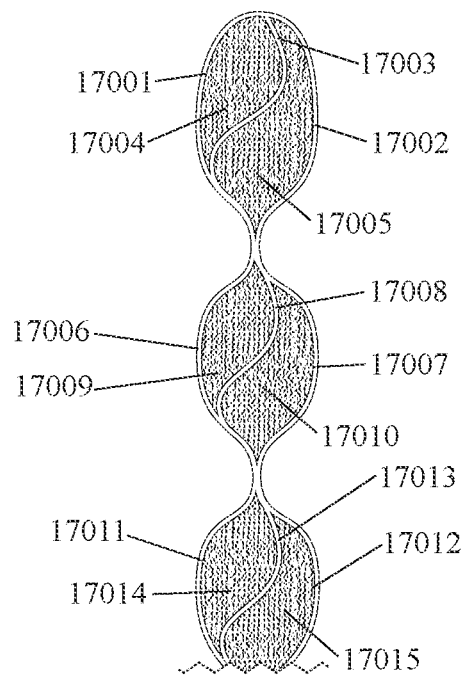
FIG. 17 shows an intrasacular aneurysm occlusion device with a series of mesh-filled loops and a central sinusoidal wire.

FIG. 17 shows an example of an aneurysm occlusion device with a plurality of connected petal-shaped longitudinal segments. Each longitudinal segment has a first longitudinal wire which forms one side of the segment, a second longitudinal wire which forms the opposite side of the segment, a mesh which spans between the first and second wires, and an undulating longitudinal wire between the first and second longitudinal wires.

Specifically, FIG. 17 shows an aneurysm occlusion device with a plurality of connected petal-shaped longitudinal segments. Three segments are shown here. Each of the three segments has a first longitudinal wire (17001, 17006, and 17011, respectively), a second longitudinal wire (17002, 17007, and 17012, respectively), a (two-part) mesh (17004 and 17005, 17009 and 17010, and 17014 and 17015, respectively) which spans between the first and second wires, and an undulating longitudinal wire (17003, 17008, and 17013, respectively) between the first and second wires. In an example, an undulating longitudinal wire can be sinusoidal. In an example, an undulating longitudinal wire can span a longitudinal segment in a distal-to-proximal manner. Undulating longitudinal wires can bias the common longitudinal axis of segments into curvature as they are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 18:
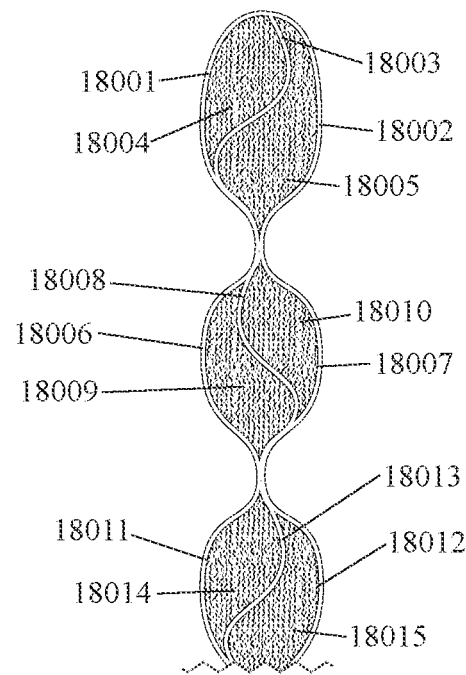
FIG. 18 shows an intrasacular aneurysm occlusion device with a series of mesh-filled loops and a central compound sinusoidal wire.

FIG. 18 shows an example of an aneurysm occlusion device like the one shown in FIG. 17 except that the orientation of undulating longitudinal wires differs between longitudinal segments. Specifically, FIG. 18 shows an aneurysm occlusion device with a plurality of connected petal-shaped longitudinal segments. Three segments are shown here. Each of the three segments has a first longitudinal wire (18001, 18006, and 18011, respectively), a second longitudinal wire (18002, 18007, and 18012, respectively), a (two-part) mesh (18004 and 18005, 18009 and 18010, and 18014 and 18015, respectively) which spans between the first and second wires, and an undulating longitudinal wire (18003, 18008, and 18013, respectively) between the first and second wires. Undulating longitudinal wires can bias the common longitudinal axis of segments into curvature as they are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 19:
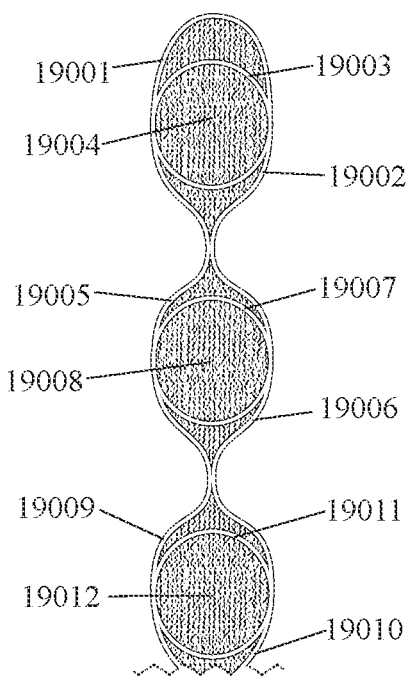
FIG. 19 shows an intrasacular aneurysm occlusion device with a series of concentric mesh-filled loops.

FIG. 19 shows an example of an aneurysm occlusion device with a plurality of connected petal-shaped longitudinal segments (three shown here), wherein each of the three segments has a first-side longitudinal wire (19001, 19005, and 19009, respectively), a second-side longitudinal wire (19002, 19006, and 19010, respectively), an inner wire loop (19003, 19007, and 19011, respectively) between the first-side and second-side wires, and a mesh (19004, 19008, and 19012, respectively) within the inner wire loop. In an example, an inner wire loop can be circular, elliptical, or oval. In an example, an inner wire loop can expand laterally and shrink longitudinally as a segment is inserted into an aneurysm sac. Example variations and descriptions discussed elsewhere in this disclosure or in priority-linked disclosures can be applied to this example, but are not repeated here in order to reduce redundancy.

Figure 20:
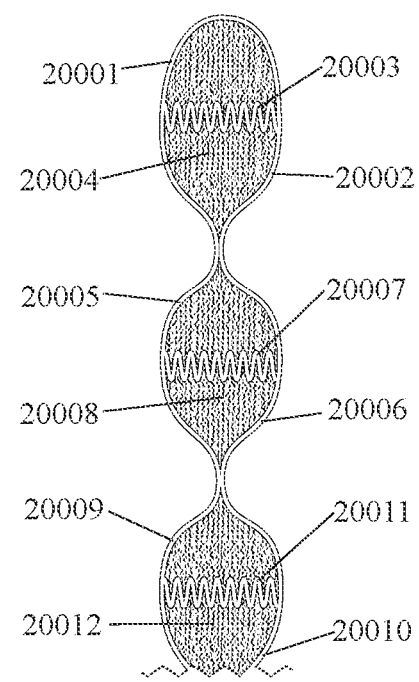
FIG. 20 shows an intrasacular aneurysm occlusion device with a series of mesh-filled loops with lateral springs.

FIG. 20 shows an example of an aneurysm occlusion device with a plurality of connected petal-shaped longitudinal segments (three shown here), wherein each of the three segments has a first-side longitudinal wire (20001, 20005, and 20009, respectively), a second-side longitudinal wire (20002, 20006, and 20010, respectively), a mesh (20004, 20008, and 20012, respectively) between the first-side and second-side wires, and a spring and/or coil (20003, 20007, and 20011, respectively) between the first-side and second-side wires. In an example, a spring and/or coil can connect first-side and second-side wires in a lateral manner. In an example, a spring and/or coil can push first-side and second-side wires apart as a segment is inserted into an aneurysm sac. Example variations and descriptions discussed elsewhere in this disclosure or in priority-linked disclosures can be applied to this example, but are not repeated here in order to reduce redundancy.

Figure 21:
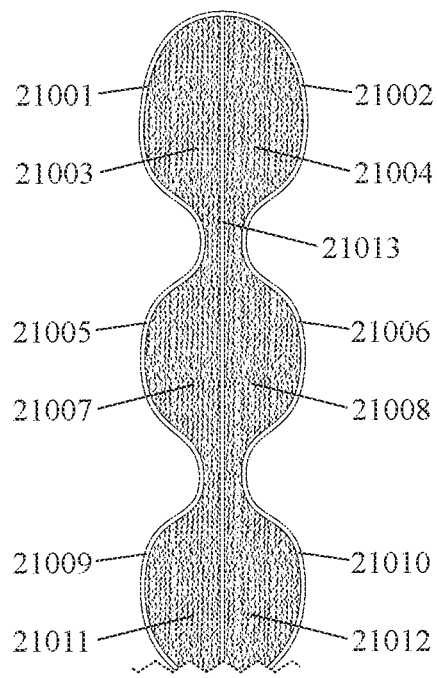
FIG. 21 shows an intrasacular aneurysm occlusion device with a series of mesh-filled loops with a central straight longitudinal wire.

FIG. 21 shows an example of an aneurysm occlusion device with an undulating (e.g. sinusoidal-sided) sequence of (alternating) wide and narrow longitudinal segments (three shown here), wherein each of the three segments has a first-side longitudinal wire (21001, 21005, and 21009, respectively), a second-side longitudinal wire (21002, 21006, and 21010, respectively), and a two-part mesh (21003 and 21004, 21007 and 21008, and 21011 and 21012, respectively) between the first-side and second-side wires. This example also includes a central longitudinal wire 21013 which spans all segments. In this example, the same continuous first-side longitudinal wire also spans all segments and the same continuous second-side longitudinal wire also spans all segments. In other examples, there can be separate first-side and second-side side wires for different segments. In this example, the same side of a two-part mesh spans all segments. In other examples, there can be separate side meshes for different segments.

In an example, a first part of mesh (e.g. 21003) on a first side (e.g. left side) relative to a longitudinal axis can have a first level of elasticity and/or flexibility, a second part of mesh (e.g. 21004) on a second side (e.g. right side) of the longitudinal axis can have a second level of elasticity and/or flexibility, and the second level can be different than the first level. In an example, such a longitudinally-asymmetric (left-side vs. right-side) difference in mesh elasticity and/or flexibility can bias the longitudinal axis of segments into curvature as they are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 22:
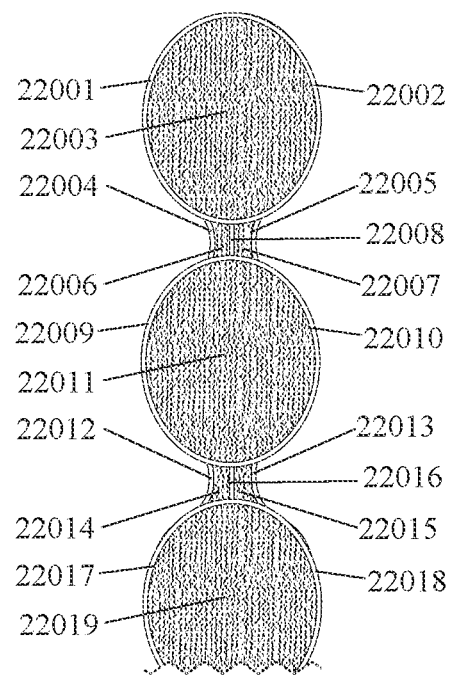
FIG. 22 shows an intrasacular aneurysm occlusion device with a series of wide mesh-filled loops connected by narrow mesh-filled segments.

FIG. 22 shows an example of an aneurysm occlusion device with a sequence of connected (alternating) wide and narrow longitudinal segments. Three wide segments and two narrow segments shown here. In this example, each of the three wide segments has a first-side wide segment wire (22001, 22009, and 22017, respectively), a second-side wide segment wire (22002, 22010, and 22018, respectively), and a wide segment mesh (22003, 22011, and 22019, respectively) between the first-side and second-side wide segment wires. In this example, the first-side wide segment wire and the second-side wide segment wire are both part of the same continuous circular, elliptical, or oval loop. In this example, each of the two narrow segments has a first-side narrow segment wire (22004 and 22012, respectively), a second-side narrow segment wire (22005 and 22013, respectively), a central longitudinal narrow segment wire (22008 and 22016, respectively), a first-side narrow segment mesh and/or elastic band (22006 and 22014, respectively), and a second-side narrow segment mesh and/or elastic band (22007 and 22015, respectively).

In an example, a first-side (e.g. left side) narrow segment mesh and/or elastic band (e.g. 22006) can have a first level of elasticity and/or flexibility, a second-side (e.g. right side) narrow segment mesh and/or elastic band (e.g. 22007) can have a second level of elasticity and/or flexibility, and the second level can be different than the first level. In an example, such a longitudinally-asymmetric (left-side vs. right-side) difference in narrow segment mesh elasticity and/or flexibility can bias the longitudinal axis of segments into curvature as they are inserted into an aneurysm. In an example, this curvature can cause connected wide segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 23:
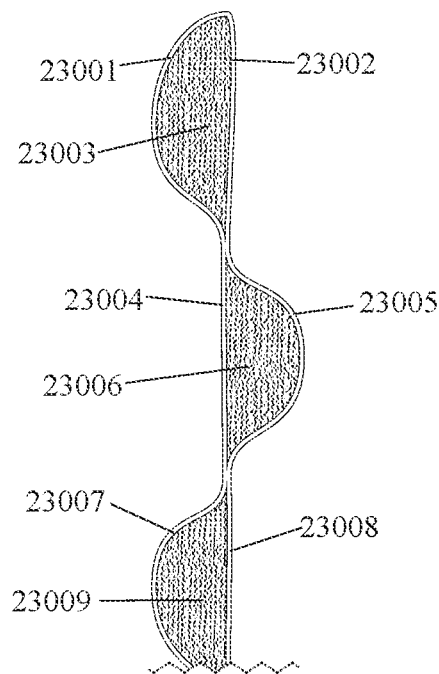
FIG. 23 shows an intrasacular aneurysm occlusion device with a series of alternating single-phase-sinusoidal mesh-filled loops.

FIG. 23 shows an example of an aneurysm occlusion device with a sequence of single-phase sinusoidal segments (e.g. positive half of sinusoidal cycle and then negative half of sinusoidal cycle) with alternating (left side and then right side) orientations. Three segments are shown here. Each of these three segments has a first-side (e.g. left side) longitudinal wire (23001, 23004, and 23007, respectively), a second-side (e.g. right side) longitudinal wire (23002, 23005, and 23008, respectively), and an inner mesh (23003, 23006, and 23009, respectively) which spans between the first-side and second-side wires. The alternating (left side vs. right side) orientations of segments can bias their longitudinal axis into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 24:
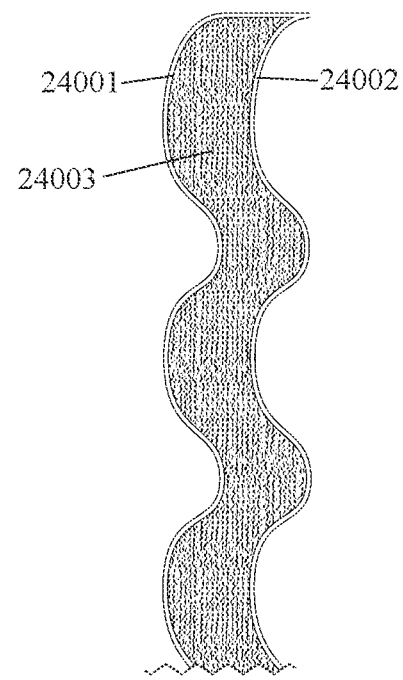
FIG. 24 shows an intrasacular aneurysm occlusion device with two parallel undulating wires connected by a mesh.

FIG. 24 shows an example of an aneurysm occlusion device with an undulating embolic ribbon comprising a first-side (e.g. left-side) undulating longitudinal wire 24001, a second-side (e.g. right-side) undulating longitudinal wire 24002, and a mesh 24003 between the first-side and second-side longitudinal wires. In an example, undulations can be sinusoidal. In an example, a ribbon's undulations can bias it into curvature as it is inserted into an aneurysm. In an example, this curvature can cause the ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 25:
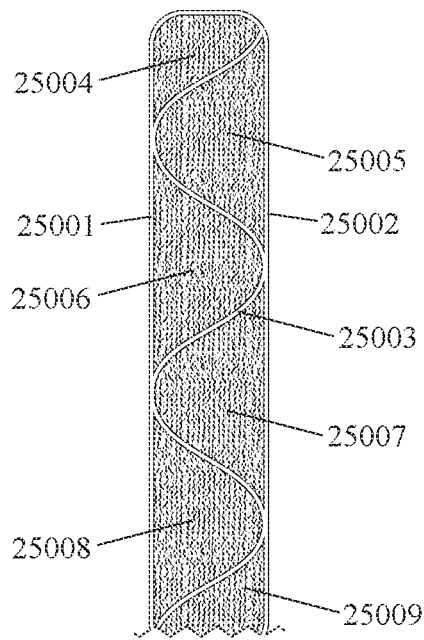
FIG. 25 shows an intrasacular aneurysm occlusion device with two straight wires connected by a mesh and a sinusoidal central wire.

FIG. 25 shows an example of an aneurysm occlusion device with an embolic ribbon comprising a first-side (e.g. left-side) longitudinal wire 25001, a second-side (e.g. right-side) longitudinal wire 25002, a central arcuate longitudinal wire 25003 between the first-side and second-side longitudinal wires, and a plurality of mesh sections (25004, 25005, 25006, 25007, 25008, and 25009) between the first-side and second-side longitudinal wires (on different sides of the central arcuate longitudinal wire). In an example, a central arcuate longitudinal wire can be sinusoidal. In an example, a first mesh section (e.g. 25004) on a first side (e.g. the left side) of a central arcuate longitudinal wire can have a first level of elasticity and/or flexibility, a second mesh section (e.g. 25005) on a second side (e.g. the right side) of a central arcuate longitudinal wire can have a second level of elasticity and/or flexibility, and the second level can be different than the first level. In an example, such a longitudinally-asymmetric (left-side vs. right-side) difference in elasticity and/or flexibility can bias a ribbon into curvature as it is inserted into an aneurysm. In an example, this curvature can cause the ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 26:
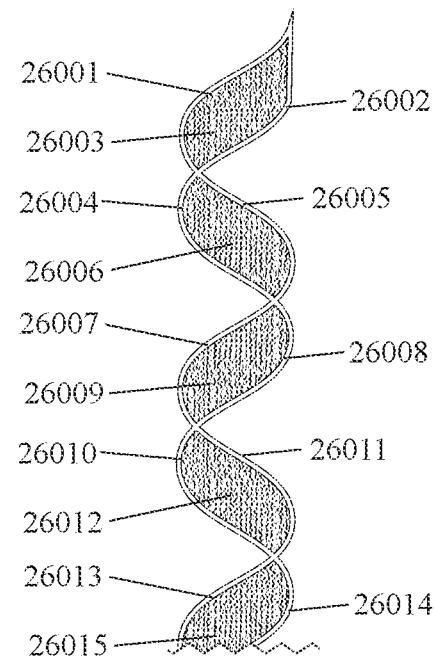
FIG. 26 shows an intrasacular aneurysm occlusion device with two overlapping out-of-phase-sinusoidal wires and a mesh between them.

FIG. 26 shows an example of an aneurysm occlusion device comprising a longitudinal sequence of segments formed by the areas between two intersecting sinusoidal side wires. In this example, the two side wires are sinusoidal with the same amplitude, wavelength, and central longitudinal axis—but are out of phase with each other. In an example, two side wires can be sinusoidal and out of phase by approximately 90 degrees. In an example, two side wires can be sinusoidal and out of phase by a number of degrees within the range of 20 to 160. FIG. 26 shows five segments formed by the intersection of two out-of-phase sinusoidal side wires. Each of the five segments comprises: a first-side (e.g. left side) longitudinal wire portion (26001, 26004, 26007, 26010, and 26013, respectively), a second-side (e.g. right side) longitudinal wire portion (26002, 26005, 26008, 26011, and 26014, respectively), and an inner mesh (26003, 26006, 26009, 26012, and 26015, respectively) between the first-side and second-side wire portions. The alternating orientations of segments formed by the intersecting sinusoidal side wires can bias the longitudinal axis of the sequence into curvature as the segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 27:
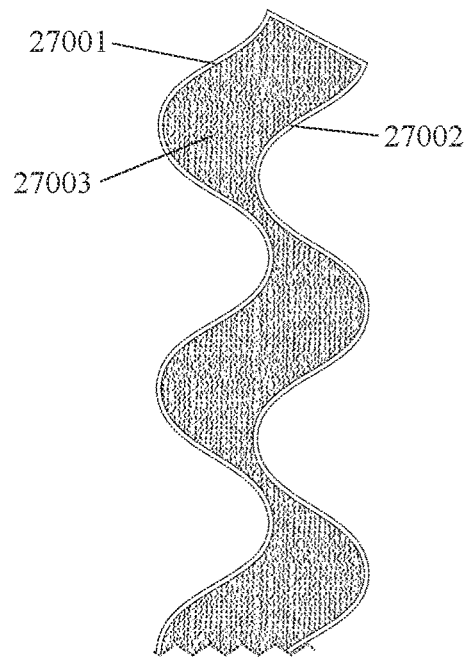
FIG. 27 shows a first intrasacular aneurysm occlusion device with two non-overlapping out-of-phase-sinusoidal wires and a mesh between them.

FIG. 27 shows an example of an aneurysm occlusion device comprising an undulating embolic ribbon formed by the area between two non-intersecting sinusoidal side wires which have the same amplitude and wavelength, but have different longitudinal axes and are out of phase with each other. In an example, two non-intersecting sinusoidal side wires can be out of phase by approximately 90 degrees. In an example, two non-intersecting sinusoidal side wires can be out of phase by a number of degrees within the range of 20 to 160. FIG. 27 shows an undulating embolic ribbon comprising a first-side (e.g. left-side) undulating longitudinal wire 27001, a second-side (e.g. right-side) undulating longitudinal wire 27002, and a mesh 27003 between the first-side and second-side longitudinal wires. In an example, a ribbon's undulations can bias it into curvature as it is inserted into an aneurysm. In an example, this curvature can cause the ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 28:
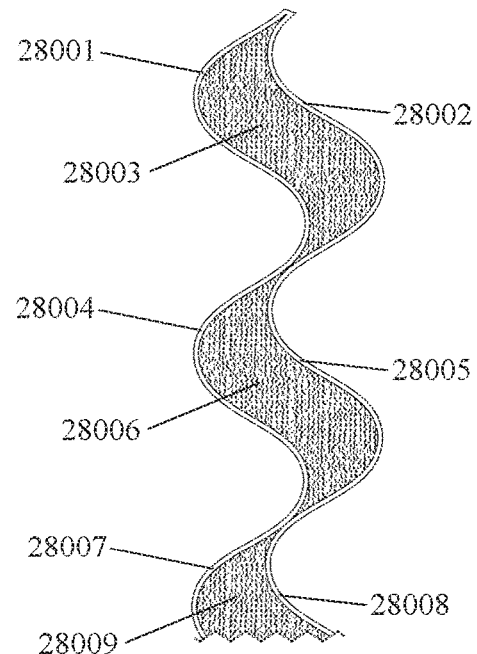
FIG. 28 shows a second intrasacular aneurysm occlusion device with two non-overlapping out-of-phase-sinusoidal wires and a mesh between them.

FIG. 28 shows an example of an aneurysm occlusion device comprising a longitudinal sequence of segments formed by the areas between two tangential sinusoidal side wires. In this example, the two side wires are sinusoidal with the same amplitude and wavelength, but are out of phase with each other by a number of degrees within the range of 20 to 160. FIG. 28 shows three segments formed between two out-of-phase sinusoidal side wires. Each of the three segments comprises: a first-side (e.g. left side) longitudinal wire portion (28001, 28004, and 28007, respectively), a second-side (e.g. right side) longitudinal wire portion (28002, 28005, and 28008, respectively), and an inner mesh (28003, 28006, and 28009, respectively) between the first-side and second-side wire portions. The alternating orientations of segments formed by the sinusoidal side wires can bias the longitudinal axis of the sequence into curvature as the segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 29:
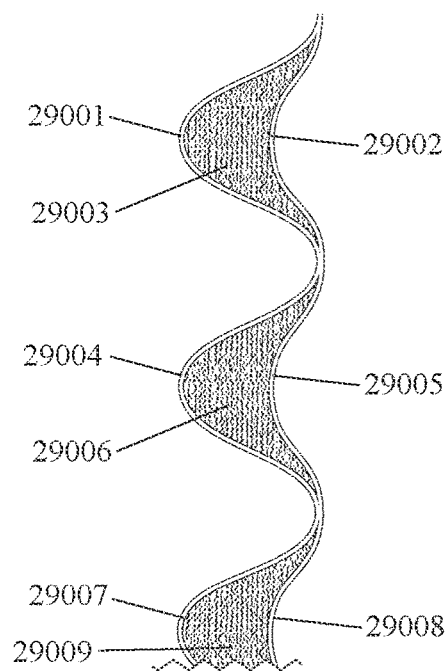
FIG. 29 shows an intrasacular aneurysm occlusion device with two sinusoidal wires with different amplitudes and a mesh between them.

FIG. 29 shows an example of an aneurysm occlusion device comprising a longitudinal sequence of segments formed by the areas between two tangential sinusoidal side wires with the same wavelength and phase, but different amplitudes. FIG. 29 shows three segments formed the intersection of these two sinusoidal side wires. Each of the three segments comprises: a first-side (e.g. left side) longitudinal wire portion (29001, 29004, and 29007, respectively), a second-side (e.g. right side) longitudinal wire portion (29002, 29005, and 29008, respectively), and an inner mesh (29003, 29006, and 29009, respectively) between the first-side and second-side wire portions. In this example, the first-side longitudinal wire is sinusoidal with a first amplitude, the second-side longitudinal wire is sinusoidal with a second amplitude, and the second amplitude is different than the first amplitude. The longitudinally-asymmetric (right side vs. left side) geometry of these segments can bias their common longitudinal axis into curvature as the segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 30:
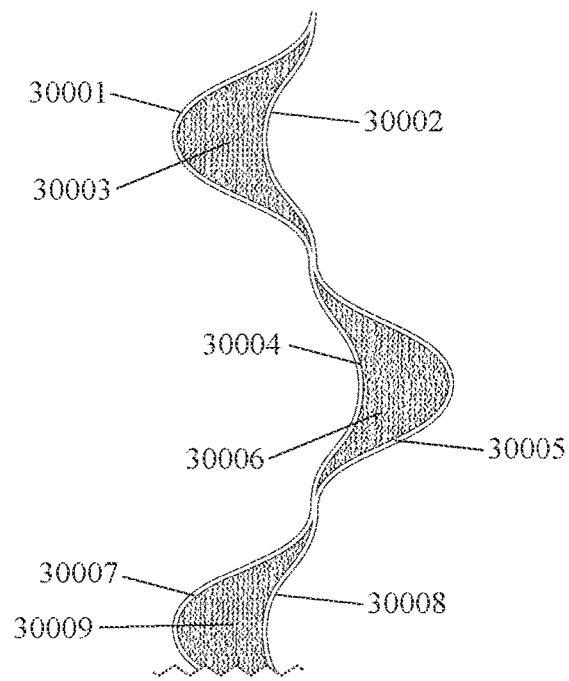
FIG. 30 shows an intrasacular aneurysm occlusion device with laterally-alternating sinusoidal mesh-filled segments.

FIG. 30 shows an example of an aneurysm occlusion device with a plurality of longitudinal segments which are geometrically-asymmetric with respect to their longitudinal axes, which each have the same shape, and which differ in orientation. Three segments are shown here. Each of the three segments has a first-side longitudinal wire (30001, 30004, and 30007, respectively), a second-side longitudinal wire (30002, 30005, and 30008, respectively), and an inner mesh (30003, 30006, and 30009, respectively) between the first-side and second-side wires. The geometric-asymmetry of these segments with respect to their longitudinal axes and their differences in orientation can bias their common longitudinal axis into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 31:
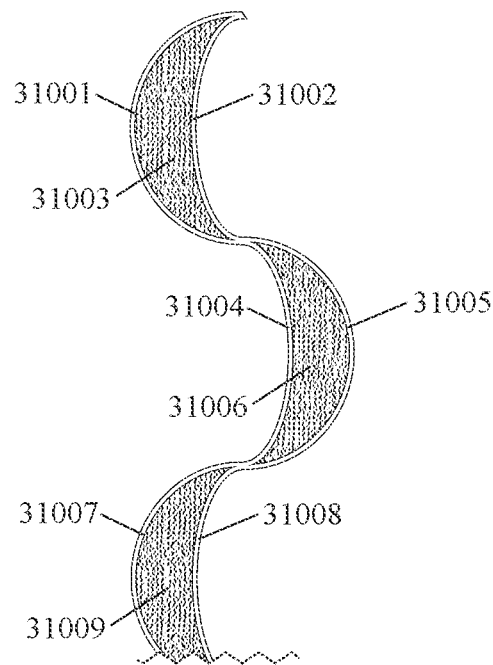
FIG. 31 shows an intrasacular aneurysm occlusion device with a series of laterally-alternating crescent-shaped mesh-filled segments.

FIG. 31 shows an example of an aneurysm occlusion device with a plurality of connected crescent-shaped longitudinal segments. Three segments are shown here. In this example, crescent-shaped segments have different orientations. In an example, crescent-shaped segments can all have the same orientation. In this example, each of the three segments has a first longitudinal wire (31001, 31004, and 31007, respectively), a second longitudinal wire (31002, 31005, and 31008, respectively), and an inner mesh (31003, 31006, and 31009, respectively) between the first and second wires. The geometric-asymmetry of these segments with respect to their longitudinal axes and their differences in orientation can bias their common longitudinal axis into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 32:
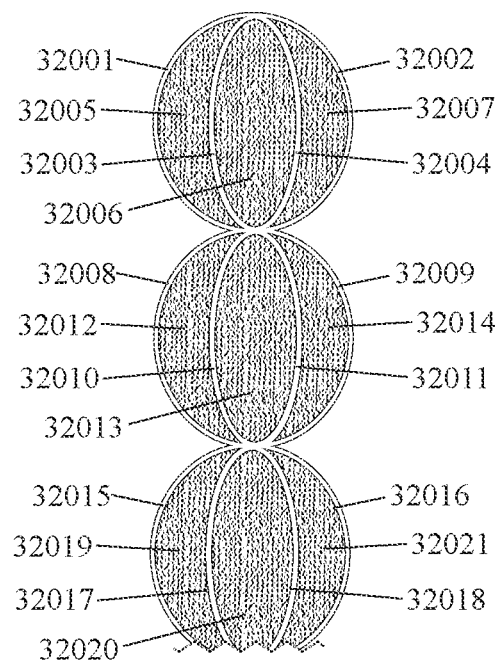
FIG. 32 shows an intrasacular aneurysm occlusion device with a series of concentric elliptical mesh-filled loops.

FIG. 32 shows an example of an aneurysm occlusion device with a plurality of connected arcuate segments. Three segments are shown here. In this example, each of the arcuate segments is circular with an inner elliptical loop. In an example, an arcuate segment can be circular, elliptical, or oval. Each of the three segments has a first side exterior wire (32001, 32008, and 32015, respectively), a second side exterior wire (32002, 32009, and 32016, respectively), a first side loop wire (32003, 32010, and 32017, respectively), a second side loop wire (32004, 32011, and 32018, respectively), a first side mesh (32005, 32012, and 32019, respectively) between the first side and second side exterior wires, a second side mesh (32007, 32014, 32021, respectively) between the first side and second side exterior wires, and a central mesh (32006, 32013, and 32020, respectively) between the first side loop wire and the second side loop wire. In an example, a first side mesh (e.g. 32005) on a first side (e.g. the left side) can have a first level of elasticity and/or flexibility, a second mesh section (e.g. 32007) on a second side (e.g. the right side) can have a second level of elasticity and/or flexibility, and the second level can be different than the first level. In an example, such a longitudinally-asymmetric (left-side vs. right-side) difference in elasticity and/or flexibility can bias the longitudinal axis of a plurality of segments into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 33:
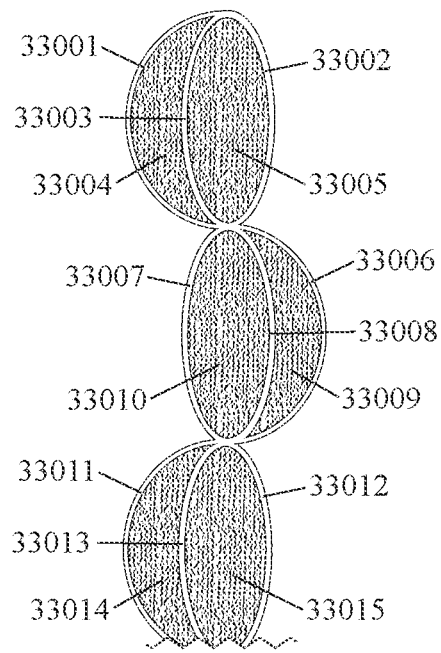
FIG. 33 shows an intrasacular aneurysm occlusion device with a series of laterally-alternating bowl-shaped mesh-filled segments.

FIG. 33 shows an example of an aneurysm occlusion device with a plurality of connected arcuate segments. Three segments are shown here. Each of the three segments has a first side wire (33001, 33007, and 33011, respectively), a second side wire (33002, 33006, and 33012, respectively), an interior wire (33003, 33008, and 33013, respectively) between the first side and second side wires, a central mesh (33005, 33010, and 33015, respectively), and a side mesh (33004, 33009, and 33014, respectively). In an example, such a longitudinally-asymmetric (left-side vs. right-side) geometry and the different orientations of the segments can bias their longitudinal axis into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 34:
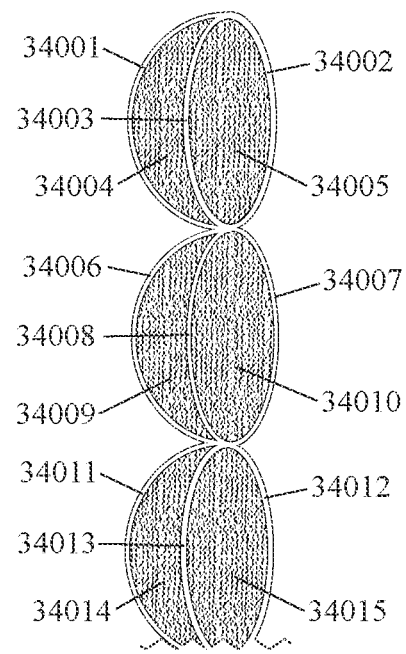
FIG. 34 shows an intrasacular aneurysm occlusion device with a series of collateral bowl-shaped mesh-filled segments.

FIG. 34 shows an example of an aneurysm occlusion device with a plurality of connected arcuate segments. Three segments are shown here. Each of the three segments has a first side wire (34001, 34006, and 34011, respectively), a second side wire (34002, 34007, and 34012, respectively), an interior wire (34003, 34008, and 34013, respectively) between the first side and second side wires, a central mesh (34005, 34010, and 34015, respectively), and a side mesh (34004, 34009, and 34014, respectively). In an example, having longitudinally-asymmetric (left-side vs. right-side) segments can bias their common longitudinal axis into curvature as these segments are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 35:
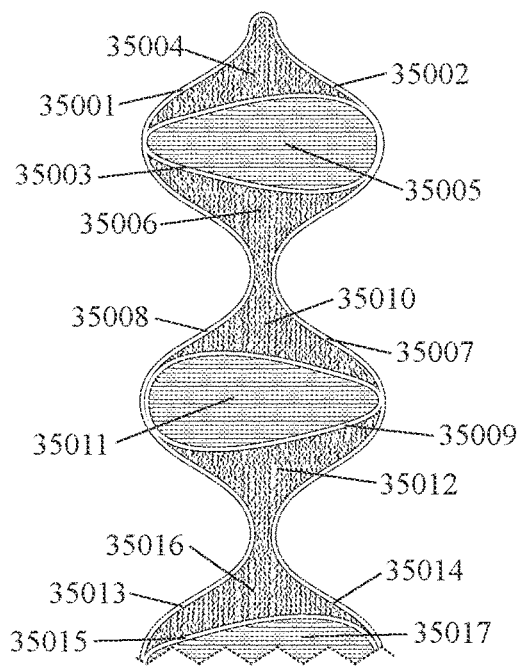
FIG. 35 shows an intrasacular aneurysm occlusion device with two sinusoidal wires and laterally-alternating asymmetric mesh-filled loops.

FIG. 35 shows an example of an aneurysm occlusion device with a sequence of (wide and narrow) segments formed by the areas between two non-intersecting sinusoidal (right and left) side wires with the same wavelength and amplitude, but opposite phases (i.e. a 180-degree phase difference). Further, each of the wide segments contains a longitudinally-asymmetric inner loop. Three wide segments are shown. Each of the three wide segments has a first-side longitudinal wire (35001, 35008, and 35013, respectively), a second-side longitudinal wire (35002, 35007, and 35014, respectively), a longitudinally-asymmetric inner wire loop (35003, 35009, and 35015, respectively) between the first-side and second-side wires, one or more outer mesh portions (35004, 35006, 35010, 35012, and 35016) between the first-side and second-side wires, and a inner mesh portion (35005, 35011, and 35017, respectively) within the inner wire loop. In this example, the orientations of the longitudinally-asymmetric loops differ between segments. The longitudinally-asymmetric (left-side vs. right-side) geometry of the inner wire loops and their differing orientations can bias the common longitudinal axis of the segments into curvature as they are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 36:
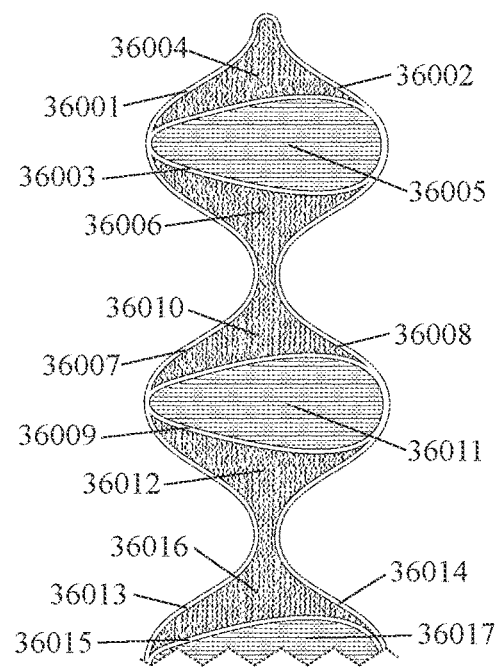
FIG. 36 shows an intrasacular aneurysm occlusion device with two sinusoidal wires and collateral asymmetric mesh-filled loops.

FIG. 36 shows an example of an aneurysm occlusion device with a sequence of (wide and narrow) segments formed by the areas between two non-intersecting sinusoidal (right and left) side wires with the same wavelength and amplitude, but opposite phases (i.e. a 180-degree phase difference). Further, each of the wide segments contains a longitudinally-asymmetric inner loop. Three wide segments are shown. Each of the three wide segments has a first-side longitudinal wire (36001, 36007, and 36013, respectively), a second-side longitudinal wire (36002, 36008, and 36014, respectively), a longitudinally-asymmetric inner wire loop (36003, 36009, and 36015, respectively) between the first-side and second-side wires, one or more outer mesh portions (36004, 36006, 36010, 36012, and 36016) between the first-side and second-side wires, and a inner mesh portion (36005, 36011, and 36017, respectively) within the inner wire loop. In this example, the orientations of the longitudinally-asymmetric loops are the same in all segments. The longitudinally-asymmetric (left-side vs. right-side) geometry of the inner wire loops can bias the common longitudinal axis of the segments into curvature as they are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 37:
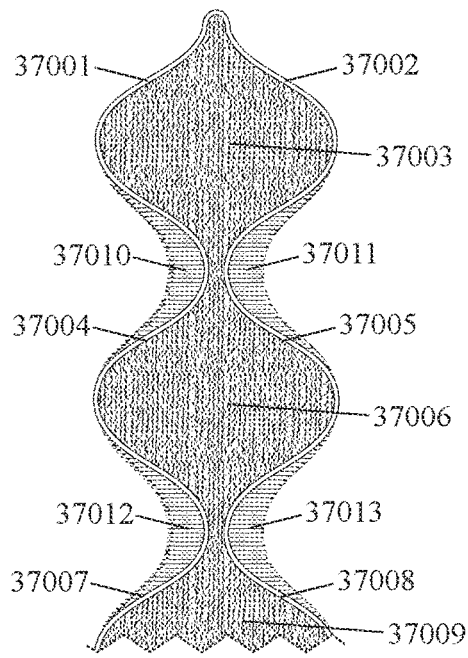
FIG. 37 shows an intrasacular aneurysm occlusion device with two sinusoidal wires and bilateral elastic connectors.

FIG. 37 shows an example of an aneurysm occlusion device with a sequence of (wide and narrow) segments formed by the areas between two non-intersecting sinusoidal (right and left) side wires with the same wavelength and amplitude, but opposite phases (i.e. a 180-degree phase difference). This example also includes longitudinally-symmetric (e.g. left side and right side) elastic connectors between pairs of wide segments. Three wide segments are shown. Each of the three wide segments has a first-side longitudinal wire (37001, 37004, and 37007, respectively), a second-side longitudinal wire (37002, 37005, and 37008, respectively), and a mesh (37003, 37006, and 37009, respectively) between the first-side and second-side longitudinal wires. There are also first-side (e.g. left-side) elastic connectors (37010 and 37012) and second-side (e.g. right-side) elastic connectors (37011 and 37013) between pairs of wide segments. In an example, a first-side elastic connector (e.g. 37010) can have a first level of elasticity and/or flexibility, a second-side elastic connector (e.g. 37011) can have a second level of elasticity and/or flexibility, and the second level can be different than the first level. In an example, such a longitudinally-asymmetric (left-side vs. right-side) difference in elasticity and/or flexibility can bias the common longitudinal axis of segments into curvature as they are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 38:
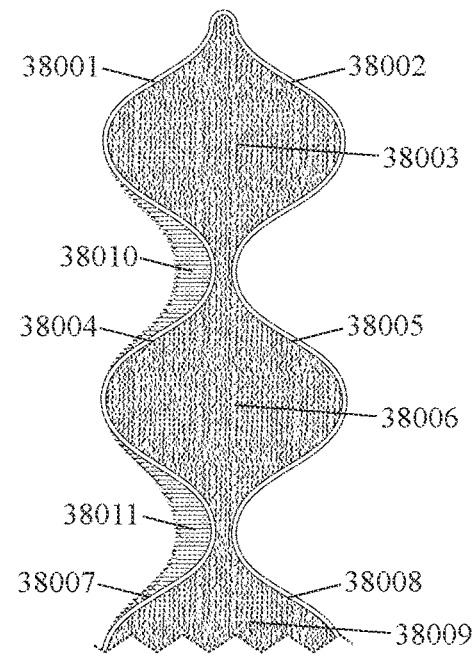
FIG. 38 shows an intrasacular aneurysm occlusion device with two sinusoidal wires and unilateral elastic connectors.

FIG. 38 shows an example of an aneurysm occlusion device with a sequence of (wide and narrow) segments formed by the areas between two non-intersecting sinusoidal (right and left) side wires with the same wavelength and amplitude, but opposite phases (i.e. a 180-degree phase difference). This example also includes longitudinally-asymmetric (e.g. left side only) elastic connectors between pairs of wide segments. Three wide segments are shown. Each of the three wide segments has a first-side longitudinal wire (38001, 38004, and 38007, respectively), a second-side longitudinal wire (38002, 38005, and 38008, respectively), and a mesh (38003, 38006, and 38009, respectively) between the first-side and second-side longitudinal wires.

There are also first-side only (e.g. left-side only) elastic connectors 38010 and 38011 between pairs of wide segments. In an example, longitudinally-asymmetric (left-side only) elastic connectors can bias the common longitudinal axis of segments into curvature as they are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 39:
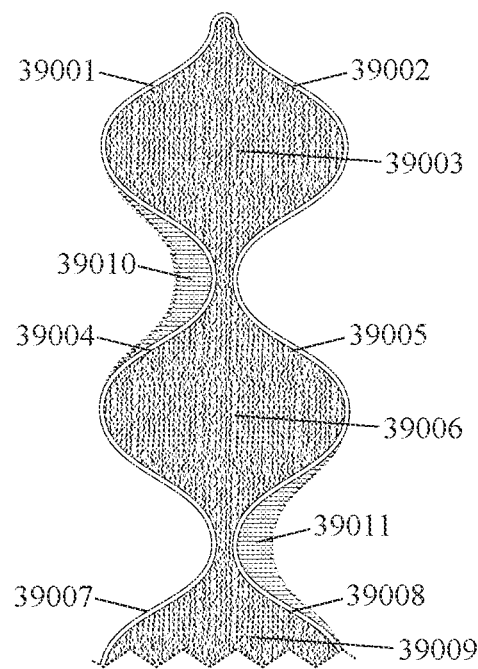
FIG. 39 shows an intrasacular aneurysm occlusion device with two sinusoidal wires and laterally-alternating elastic connectors.

FIG. 39 shows an example of an aneurysm occlusion device with a sequence of (wide and narrow) segments formed by the areas between two non-intersecting sinusoidal (right and left) side wires with the same wavelength and amplitude, but opposite phases (i.e. a 180-degree phase difference). This example also includes longitudinally-asymmetric (e.g. alternating left-side and right-side) elastic connectors between pairs of wide segments. Three wide segments are shown. Each of the three wide segments has a first-side longitudinal wire (39001, 39004, and 39007, respectively), a second-side longitudinal wire (39002, 39005, and 39008, respectively), and a mesh (39003, 39006, and 39009, respectively) between the first-side and second-side longitudinal wires. There is one left-side elastic connector 39010 between one pair of wide segments and one right-side elastic connector 39011 between another pair of wide segments. In an example, such longitudinally-asymmetric elastic connectors can bias the common longitudinal axis of segments into curvature as they are inserted into an aneurysm. In an example, this curvature can cause connected segments to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 40:
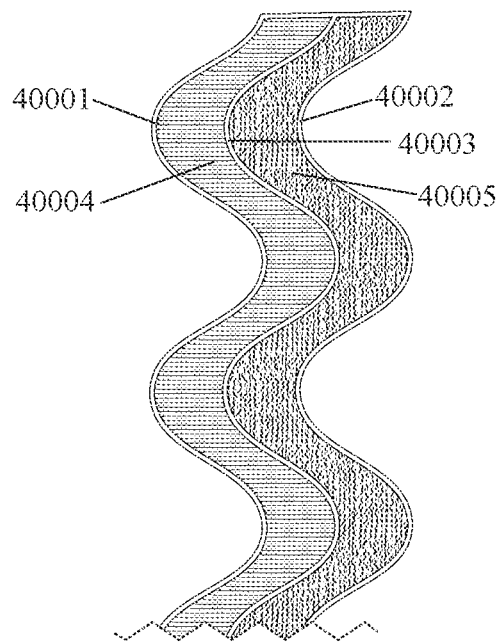
FIG. 40 shows an intrasacular aneurysm occlusion device with three parallel sinusoidal wires connected by mesh.

FIG. 40 shows an example of an aneurysm occlusion device with an undulating embolic ribbon comprising a first-side (e.g. left-side) undulating wire 40001, a second-side (e.g. right-side) undulating wire 40002, a central undulating wire 40003 between the first-side and second-side undulating wires, a first-side mesh and/or elastic band 40004 between the first-side undulating wire and the central undulating wire, and a second-side mesh and/or elastic band 40005 between the second-side undulating wire and the central undulating wire. In this example, the first-side and second-side undulating wires are non-intersecting and sinusoidal, with the same wavelength, amplitude, and phase. They are also parallel to each other. In an example, a ribbon's undulations can bias it into curvature as it is inserted into an aneurysm. In an example, a first-side mesh and/or elastic band can have a first level of elasticity and/or flexibility, a second-side mesh and/or elastic band can have a second level of elasticity and/or flexibility, and the second level can be different than the first level. In an example, a longitudinally-asymmetric (left-side vs. right-side) difference in elasticity and/or flexibility can bias a ribbon into curvature as it is inserted into an aneurysm. In an example, such curvature can cause a ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 41:
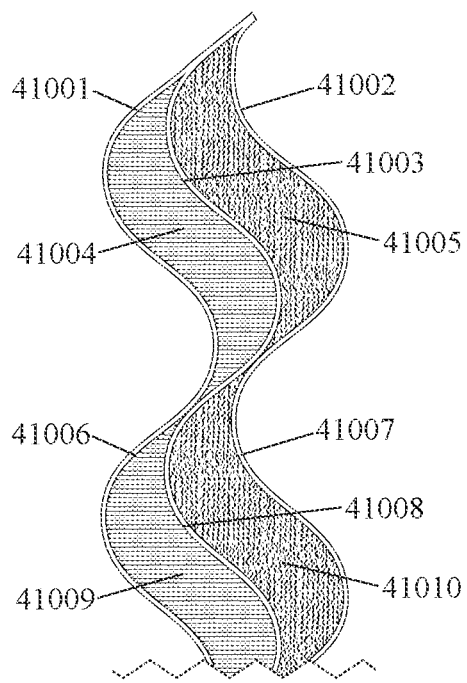
FIG. 41 shows an intrasacular aneurysm occlusion device with three out-of-phase-sinusoidal wires connected by mesh.

FIG. 41 shows an example of an aneurysm occlusion device with an undulating embolic ribbon comprising "flame-shaped" wide and narrow segments. Two wide segments are shown here. Each of the two wide segments includes a first-side (e.g. left-side) undulating wire (41001 and 41006, respectively), a second-side (e.g. right-side) undulating wire (41002 and 41007, respectively), a central undulating wire (41003 and 41008, respectively) between the first-side and second-side undulating wires, a first-side mesh and/or elastic band (41004 and 41009, respectively) between the first-side undulating wire and the central undulating wire, and a second-side mesh and/or elastic band (41005 and 41010, respectively) between the second-side undulating wire and the central undulating wire. In this example, the undulating wires are non-intersectional and sinusoidal, with a common wavelength and amplitude, but they are out-of-phase with each other. In an example, they are out-of-phase by a number of degrees ranging from 20 to 160 degrees. In an example, a ribbon's charismatic undulations can bias it into curvature as it is inserted into an aneurysm. In an example, a first-side mesh and/or elastic band can have a first level of elasticity and/or flexibility, a second-side mesh and/or elastic band can have a second level of elasticity and/or flexibility, and the second level can be different than the first level. In an example, a longitudinally-asymmetric (left-side vs. right-side) difference in elasticity and/or flexibility can bias a ribbon into curvature as it is inserted into an aneurysm. In an example, such curvature can cause a ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 42:
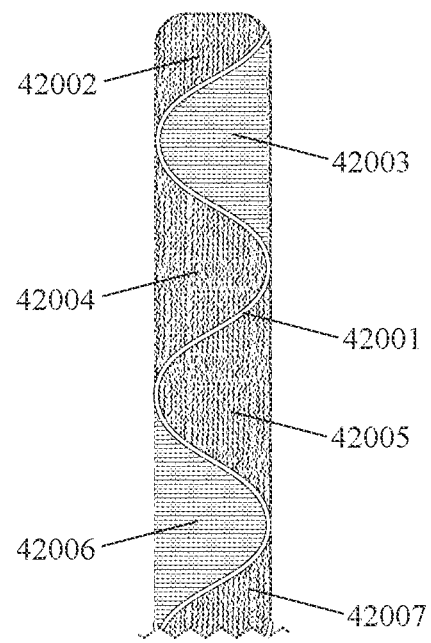
FIG. 42 shows a first intrasacular aneurysm occlusion device with two straight wires, a central sinusoidal wire, and different types of mesh between them.

FIG. 42 shows an example of an aneurysm occlusion device with an embolic ribbon comprising a central undulating wire 42001, a plurality of first-side (e.g. left-side) mesh and/or elastic sections (including 42002, 42004, and 42006) filling the (convex or concave) areas between curves on the first side of the central undulating wire, and a plurality of second-side (e.g. right-side) mesh and/or elastic sections (including 42003, 42005, and 42007) filling the (concave or convex) areas between curves on the second side of the central undulating wire. In an example, a central undulating wire can be sinusoidal. In an example, a first-side mesh and/or elastic section (e.g. 42002) can have a first level of elasticity and/or flexibility, a second-side mesh and/or elastic section (e.g. 42003) can have a second level of elasticity and/or flexibility, and the second level can be different than the first level. In an example, one first-side mesh and/or elastic section (e.g. 42002) can have a first level of elasticity and/or flexibility, a different first-side mesh and/or elastic section (e.g. 42006) can have a second level of elasticity and/or flexibility, and the second level can be different than the first level. In an example, such differences in elasticity and/or flexibility can bias a ribbon into curvature as it is inserted into an aneurysm. In an example, this curvature can cause the ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 43:
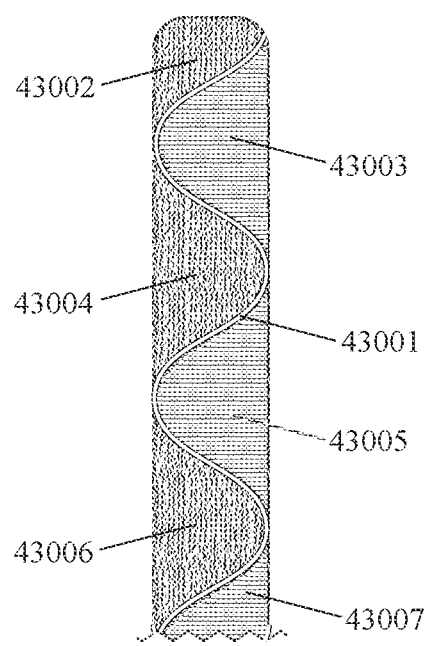
FIG. 43 shows a second intrasacular aneurysm occlusion device with two straight wires, a central sinusoidal wire, and different types of mesh between them.

FIG. 43 shows an example of an aneurysm occlusion device with an embolic ribbon comprising a central undulating wire 43001, a plurality of first-side (e.g. left-side) mesh and/or elastic sections (including 43002, 43004, and 43006) filling the (convex or concave) areas between curves on the first side of the central undulating wire, and a plurality of second-side (e.g. right-side) mesh and/or elastic sections (including 43003, 43005, and 43007) filling the (concave or convex) areas between curves on the second side of the central undulating wire. In an example, a central undulating wire can be sinusoidal. In an example, first-side meshes and/or elastic sections can have a first level of elasticity and/or flexibility, second-side meshes and/or elastic sections can have a second level of elasticity and/or flexibility, and the second level can be different than the first level. In an example, such a longitudinally-asymmetric (left-side vs. right-side) difference in elasticity and/or flexibility can bias a ribbon into curvature as it is inserted into an aneurysm. In an example, this curvature can cause the ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 44:
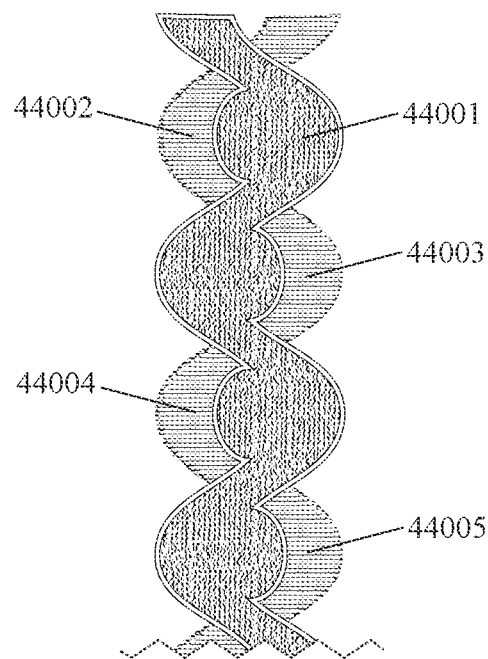
FIG. 44 shows an intrasacular aneurysm occlusion device with inter-twined undulating bands.

FIG. 44 is a weird design that will probably never see the light of day, but Al might like it. Did you know that Al was valedictorian of his class at Lynwood High School? He does amazing parodies. Ah well, now back to aneurysm occlusion devices. FIG. 44 is an aneurysm occlusion device comprising: a sinusoidal ribbon 44001 with intra-curve bulges (looking like a series of apostrophes or commas with alternating orientations); and a plurality of inter-curve elastic meshes or bands (44002, 44003, 44004, and 44005). In an example, longitudinally-asymmetric (left-side vs. right-side) differences in elasticity and/or flexibility can bias a ribbon into curvature as it is inserted into an aneurysm. In an example, this curvature can cause the ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 45:
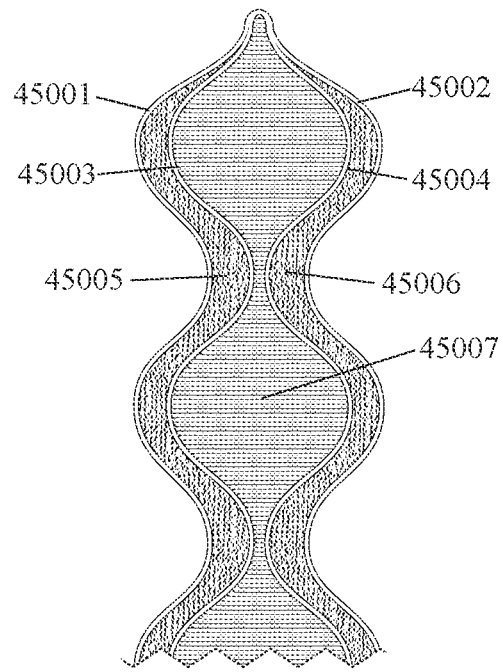
FIG. 45 shows a first intrasacular aneurysm occlusion device with four sinusoidal wires connected by mesh.

FIG. 45 shows an example of an aneurysm occlusion device with a sequence of wide and narrow segments formed by two sinusoidally-undulating ribbons with the same central longitudinal axis. In this example, each the ribbon is formed by the area between two sinusoidal side wires, wherein the two sinusoidal side wires have the same wavelength and amplitude, but opposite phases (i.e. a 180-degree phase difference). The first (outer) ribbon has a first width and the second (inner) ribbon has a second width. The first width is greater than the second width. FIG. 45 shows a first-side (e.g. left-side) sinusoidal wire 45001 of the first (outer) ribbon, a second-side (e.g. right-side) sinusoidal wire 45002 of the first (outer) ribbon, a first-side sinusoidal wire 45003 of the second (inner) ribbon, a second-side sinusoidal wire 45004 of the second (inner) ribbon, a first-side mesh 45005 between first and second ribbons, a second-side mesh 45006 between the first and second ribbons, and an inner mesh 45007 within the second ribbon. In an example, a first-side mesh can have a first level of elasticity and/or flexibility, a second-side mesh can have a second level of elasticity and/or flexibility, and the second level can be different than the first level. In an example, such a longitudinally-asymmetric (left-side vs. right-side) difference in elasticity and/or flexibility can bias the longitudinal axis of the ribbon into curvature as it is inserted into an aneurysm. In an example, this curvature can cause the ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 46:
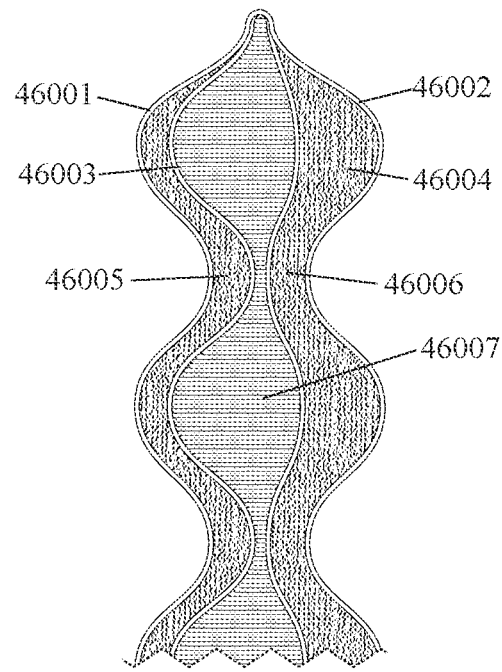
FIG. 46 shows a second intrasacular aneurysm occlusion device with four sinusoidal wires connected by mesh.

FIG. 46 shows an example of an aneurysm occlusion device like the one in FIG. 45 except that the second (inner) ribbon is longitudinally asymmetric. FIG. 46 shows a first-side (e.g. left-side) sinusoidal wire 46001 of the first (outer) ribbon, a second-side (e.g. right-side) sinusoidal wire 46002 of the first (outer) ribbon, a first-side sinusoidal wire 46003 of the second (inner) ribbon, a second-side sinusoidal wire 46004 of the second (inner) ribbon, a first-side mesh 46005 between first and second ribbons, a second-side mesh 46006 between the first and second ribbons, and an inner mesh 46007 within the second ribbon. In an example, the longitudinal asymmetry of the second (inner) ribbon can bias the longitudinal axis of the ribbon into curvature as it is inserted into an aneurysm. In an example, this curvature can cause the ribbon to accumulate into a spherical, elliptical, or other arcuate mass which occludes the aneurysm. Example variations and descriptions discussed elsewhere in this disclosure or in priority-linked disclosures can be applied to this example, but are not repeated here in order to reduce redundancy.

Figure 47:
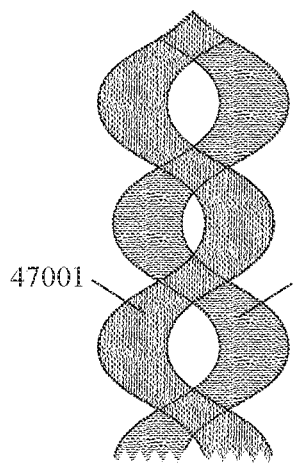
FIGS. 47 and 48 show stand-alone and sac-deployed views of an intrasacular aneurysm occlusion device with inter-twined sinusoidal bands.
Figure 48:
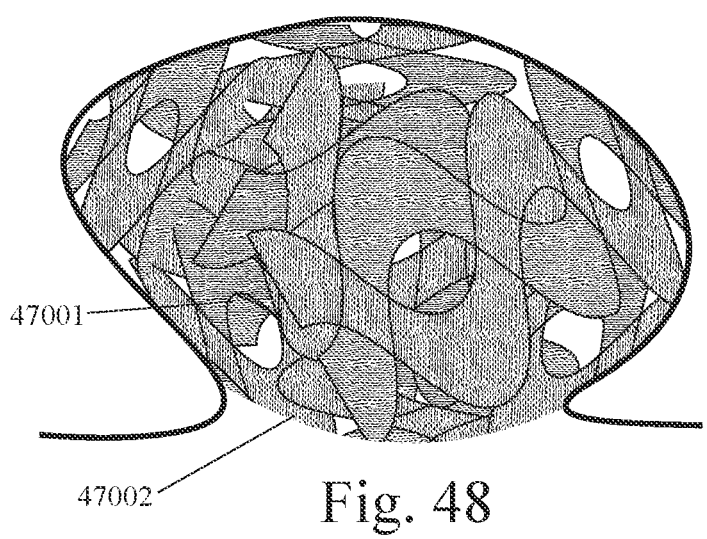

FIGS. 47 and 48 show two sequential views of an aneurysm occlusion device comprising an undulating embolic ribbon which is configured to be inserted into an aneurysm sac. This undulating embolic ribbon is configured to accumulate into an arcuate three-dimensional occlusive mass which fills an aneurysm sac. This undulating embolic ribbon further comprises a first undulating strip 47001 and a second undulating strip 47002. In this example, the second undulating strip is a reflected version of the first undulating strip, having been reflected across a longitudinal axis of the undulating embolic ribbon.

FIG. 47 shows this device at a first point in time, before it has been inserted into an aneurysm sac. FIG. 48 shows this device at a second point in time, after it has been inserted into an aneurysm sac and accumulated in an overlapping manner into an arcuate three-dimensional occlusive mass which fills an aneurysm sac. In an example, an arcuate three-dimensional occlusive mass formed within an aneurysm sac can have a shape selected from the group consisting of: sphere; ellipsoid; ovaloid; pumpkin; apple; pear; and torus. In an example, an arcuate three-dimensional occlusive mass can also have bulges and bumps which enable it to conform to the walls of an irregularly-shaped aneurysm sac. This is especially important for aneurysms which are not perfectly spherical, ellipsoidal, or ovaloidal.

Expressing this embodiment with different words, FIGS. 47 and 48 show an aneurysm occlusion device comprising: an undulating embolic ribbon which is configured to be inserted into an aneurysm sac so as to accumulate into an arcuate three-dimensional occlusive mass within the aneurysm sac, wherein the undulating embolic ribbon further comprises a first undulating strip and a second undulating strip, and wherein the first and second undulating strips are symmetric relative to each other across a longitudinal axis of the undulating embolic ribbon. In an example, an undulating strip can be sinusoidal. In an example, this aneurysm occlusion device can comprise: an undulating embolic ribbon which is configured to be inserted into an aneurysm sac so as to accumulate into an arcuate three-dimensional occlusive mass within the aneurysm sac, wherein the undulating embolic ribbon further comprises a first sinusoidal strip and a second sinusoidal strip.

In an example, a sinusoidal strip can have a constant wavelength along its entire length. In an example, the wavelength of a distal portion of a sinusoidal strip can be greater than the wavelength of a proximal portion of a sinusoidal strip, or vice versa. In an example, a sinusoidal strip can have a constant width along its entire length. In an example, the width of a distal portion of a sinusoidal strip can be greater than the width of a proximal portion of a sinusoidal strip, or vice versa. In an example, a sinusoidal strip can have a constant thickness along its entire length. In an example, the thickness of a distal portion of a sinusoidal strip can be greater than the thickness of a proximal portion of a sinusoidal strip, or vice versa. In an example, a sinusoidal strip can have a constant elasticity and/or flexibility level along its entire length. In an example, the elasticity and/or flexibility level of a distal portion of a sinusoidal strip can be greater than the elasticity and/or flexibility level of a proximal portion of a sinusoidal strip, or vice versa.

In an example, an undulating strip can be made from a metal, a polymer, or both. In an example, an undulating strip can comprise a wire mesh, net, or lattice. In an example, an undulating strip can further comprise two or more undulating wires with a mesh, net, or lattice between them. In an example, an undulating strip can further comprise two or more undulating wires with fabric between them. In an example, there can be gaps between first and second undulating strips. In an example, these gaps can vary sequentially in shape. In an example, there may be no gaps between the first and second undulating strips. In an example, first and second undulating strips can overlap. In an example, the first and second undulating strips can be attached to each other.

In an example, an undulating embolic ribbon can have cross-sectional asymmetry. In an example, this cross-sectional asymmetry can be due to cross-sectional differences in elasticity, flexibility, shape, length, and/or width. In an example, a first undulating strip can have a first elasticity level and a second undulating strip can have a second elasticity level, wherein the second elasticity level is greater than the first elasticity level. In an example, a first undulating strip can have a first flexibility level and a second undulating strip can have a second flexibility level, wherein the second flexibility level is greater than the first flexibility level. In an example, a first undulating strip can have a first width and a second undulating strip can have a second width, wherein the second width is greater than the first width.

In an example, the cross-sectional asymmetry of an undulating embolic ribbon can bias the embolic ribbon to bend to the right or to the left as it exits a catheter. Such bending can cause the undulating embolic ribbon to form an arcuate three-dimensional occlusive mass as it accumulates within an aneurysm sac. In an example, the cross-sectional asymmetry of an undulating embolic ribbon can bias the embolic ribbon to bend sequentially back and forth, oscillating to the right and to the left. Such oscillating bending can cause an undulating embolic ribbon to form an arcuate three-dimensional mass as it accumulates within an aneurysm sac. In an example, an arcuate three-dimensional mass occlusive formed with an aneurysm sac can be generally spherical, ellipsoidal, or ovaloidal in shape. In an example, an arcuate three-dimensional occlusive mass can also have bulges and/or bumps so as conform to the walls of an irregularly-shaped (e.g. non-spherical) aneurysm sac.

In an example, the cross-sectional symmetry of an undulating embolic ribbon can be adjusted by a user in real-time (as an embolic ribbon is being inserted into an aneurysm sac) so as to guide and/or steer the bending movement of the ribbon as it is deployed. This enables a user to guide the formation of an arcuate three-dimensional occlusive mass which confirms to the walls of an irregularly-shaped aneurysm sac. In an example, a user can adjust the cross-sectional asymmetry of an undulating embolic ribbon by adjusting its elasticity, flexibility, shape, length, and/or width as it is deployed within an aneurysm sac. In an example, application of electromagnetic energy to a first undulating strip and/or to a second undulating strip can change the cross-sectional asymmetry of the undulating embolic ribbon, thereby biasing the embolic ribbon to bend to the right or to the left. In an example, pulling or pushing a wire connected to the first undulating strip or connected to the second undulating strip can bias the undulating embolic ribbon to bend to the right or to the left.

In an example, this device can further comprise an electromagnetic energy source which enables a user to selectively apply electromagnetic energy to a portion of an embolic ribbon as the ribbon is deployed within an aneurysm sac. In an example, selective application of electromagnetic energy to a portion of an embolic ribbon can change the elasticity, flexibility, and/or shape of that portion. In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, this enables a user to guide and/or steer the embolic ribbon during deployment so as to create an arcuate three-dimensional occlusive mass which optimally fills an aneurysm sac.

In an example, an undulating embolic ribbon can accumulate within an aneurysm sac so as to form an arcuate three-dimensional occlusive mass, progressively filling it from the outside of the mass to the inside of the mass. In an example, a catheter dispensing an undulating embolic ribbon can be positioned in the center of an aneurysm sac so as to form an arcuate three-dimensional occlusive mass starting from the outside of the mass and then progressively filling the inside.

In an example, an undulating embolic ribbon can accumulate within an aneurysm sac so as to form an arcuate three-dimensional occlusive mass, progressing from the inside of the mass to the outside of the mass, like wrapping a ball of yarn. In an example, a catheter dispensing an undulating embolic ribbon can be positioned near the wall of an aneurysm sac so as to form an arcuate three-dimensional occlusive mass starting from the inside of the mass and then progressively covering the outside, like wrapping a ball of yarn. Relevant design variations discussed elsewhere in this disclosure or in priority-linked disclosures can also be applied to the example shown here.

Figure 49:
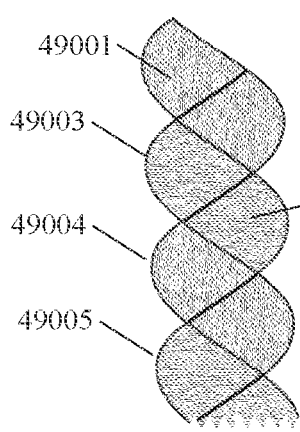
FIGS. 49 and 50 show stand-alone and sac-deployed views of an intrasacular aneurysm occlusion device with three coaxial sinusoidal wires connected by mesh.
Figure 50:
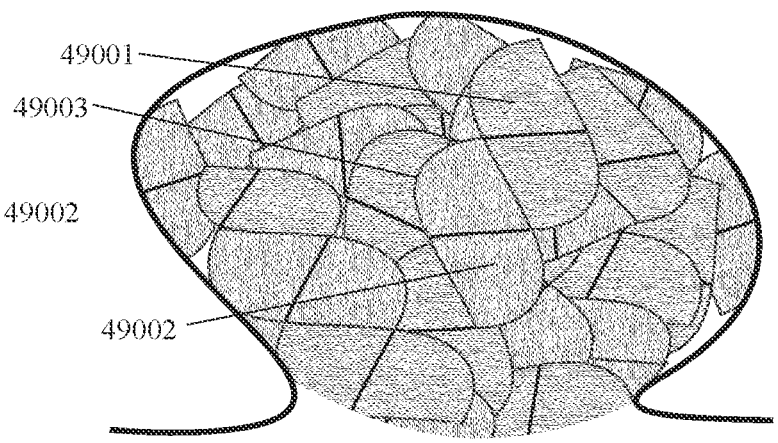

FIGS. 49 and 50 show two sequential views of an aneurysm occlusion device comprising an undulating embolic ribbon which is configured to be inserted into an aneurysm sac. This undulating embolic ribbon is configured to accumulate into an arcuate three-dimensional occlusive mass which fills an aneurysm sac. In this example, the undulating embolic ribbon further comprises: a first set of pie-slice portions (shaped like slices of pie), including 49001, along the left side of the ribbon; and a second set of pie-slice portions, including 49002, along the right side of the ribbon.

FIG. 49 shows this device at a first point in time, before it has been inserted into an aneurysm sac. FIG. 50 shows this device at a second point in time, after it has been inserted into an aneurysm sac and accumulated in an overlapping manner into an arcuate three-dimensional occlusive mass which fills the aneurysm sac. In an example, an arcuate three-dimensional occlusive mass formed within an aneurysm sac can have a shape selected from the group consisting of: sphere; ellipsoid; ovaloid; pumpkin; apple; pear; and torus. In an example, an arcuate three-dimensional occlusive mass can also have bulges and bumps which enable it to conform to the walls of an irregularly-shaped aneurysm sac. This is especially important for aneurysms which are not perfectly spherical, ellipsoidal, or ovaloidal.

In an example, pie-slice portions in a first set or in a second set can be contiguous to each other. In an example, pie-slice portions in first and second sets can interdigitate. In an example, the rounded edges of pie-slice portions can point away from the central longitudinal axis of an embolic ribbon. In an example, pie-slice portions in a second set can be made from a different material than pie-slice portions in a first set. In an example, pie-slice portions in a second set can have a different elasticity, thickness, width, and/or size than pie-slice portions in a first set. In an example, differences in material characteristics between pie-slice portions in first and second sets can bias an embolic ribbon to bend to one side (or the other) as it exits a catheter within an aneurysm sac in order to form an arcuate three-dimensional occlusive mass which fills the aneurysm sac.

This example can also be described as comprising three undulating wires, 49003, 49004, and 49005. In this example, these undulating wires are sinusoidal. In this example, there is occluding mesh or fabric between the wires. In an example, multiple sinusoidal wires in an embolic ribbon can share the same central longitudinal axis. In an example, multiple sinusoidal wires can have the same wavelength, but have different phases. In an example, the phase of a second sinusoidal wire can differ from the phase of a first sinusoidal wire by 120 degrees and the phase of a third sinusoidal wire can differ from the phase of a first sinusoidal wire by 240 degrees. In an example, the phase of a second sinusoidal wire can differ from the phase of a first sinusoidal wire by 60 degrees and the phase of a third sinusoidal wire can differ from the phase of a first sinusoidal wire by 120 degrees.

In an example, an embolic ribbon can have the same width along its entire length. In an example, a proximal portion of an embolic ribbon can be wider than its distal portion, or vice versa. In an example, an embolic ribbon can have the same thickness along its entire length. In an example, a proximal portion of an embolic ribbon can be thicker than its distal portion, or vice versa. In an example, an embolic ribbon can have the same elasticity level along its entire length. In an example, a proximal portion of an embolic ribbon can be more elastic than its distal portion, or vice versa.

In an example, there can be variation in cross-sectional differences in material characteristics in an embolic ribbon along its longitudinal axis. In an example, there can be variation in material characteristics between first set and second set portions along the longitudinal axis of an embolic ribbon. In an example, portions in a first set can be more flexible, thicker, or wider along a first segment of the longitudinal axis of a ribbon and portions in a second set can be more flexible, thicker, or wider along a second segment of the longitudinal axis of the ribbon.

In an example, variation in cross-sectional differences can cause an embolic ribbon to bend in different directions along different sections of its longitudinal axis as it exits a catheter within an aneurysm sac. In an example, variation in cross-sectional differences can cause an embolic ribbon to oscillate between bending to the left and bending to the right as it exits a catheter within an aneurysm sac. In an example, variation in differences between first and second sets can cause an embolic ribbon to oscillate and/or alternate between bending to the left and bending to the right as it exits a catheter within an aneurysm sac.

In an example, this device can further comprise an electromagnetic energy source which enables a user to selectively apply electromagnetic energy to a first set or to a second set of pie-shape portions as an embolic ribbon is deployed within an aneurysm sac. In an example, selective application of electromagnetic energy can change the elasticity, flexibility, and/or shape of a first set or a second set. In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, this enables a user to guide and/or steer the embolic ribbon during deployment so as to create an arcuate three-dimensional occlusive mass which optimally fills an aneurysm sac. Relevant design variations discussed elsewhere in this disclosure or in priority-linked disclosures can also be applied to the example shown here.

Figure 51:
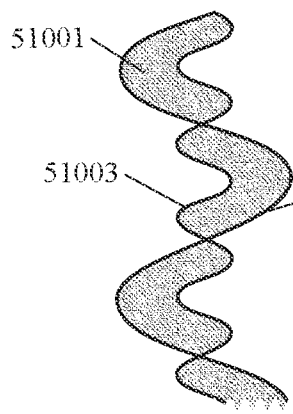
FIGS. 51 and 52 show stand-alone and sac-deployed views of an intrasacular aneurysm occlusion device with two sinusoidal wires with different frequencies connected by mesh.
Figure 52:
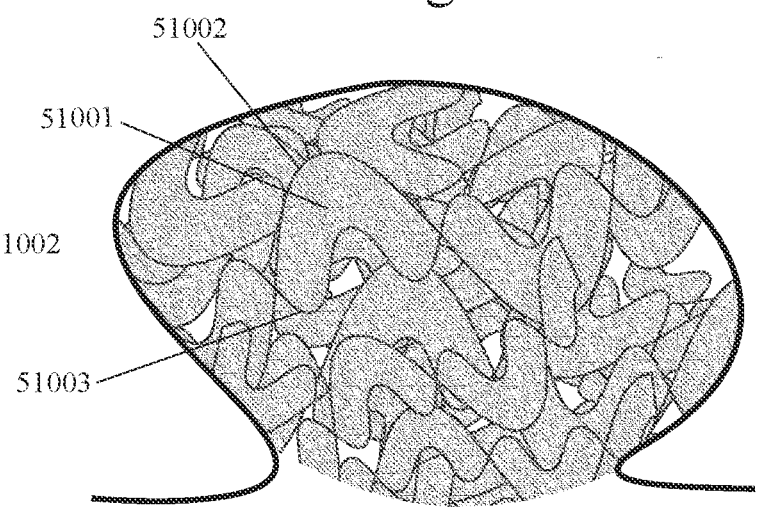

FIGS. 51 and 52 show two sequential views of an aneurysm occlusion device comprising an undulating embolic ribbon which is configured to be inserted into an aneurysm sac. This undulating embolic ribbon 51001 is configured to accumulate into an arcuate three-dimensional occlusive mass which fills the aneurysm sac. In this example, the undulating embolic ribbon further comprises: a first sinusoidal wire 51002 with a first wavelength; a second sinusoidal wire 51003 with a second wavelength, wherein the second wavelength is half of the first wavelength; and an occlusive mesh or fabric between the first sinusoidal wire and the second sinusoidal wire. In this example, the first and second sinusoidal wires share a common central longitudinal axis.

FIG. 51 shows this device at a first point in time, before it has been inserted into an aneurysm sac. FIG. 52 shows this device at a second point in time, after it has been inserted into an aneurysm sac and accumulated in an overlapping manner into an arcuate three-dimensional occlusive mass which fills the aneurysm sac. In an example, an arcuate three-dimensional occlusive mass formed within an aneurysm sac can have a shape selected from the group consisting of: sphere; ellipsoid; ovaloid; pumpkin; apple; pear; and torus. In an example, an arcuate three-dimensional occlusive mass can also have bulges and bumps which enable it to conform to the walls of an irregularly-shaped aneurysm sac. This is especially important for aneurysms which are not perfectly spherical, ellipsoidal, or ovaloidal. Relevant design variations discussed elsewhere in this disclosure or in priority-linked disclosures can also be applied to the example shown here.

Figure 53:
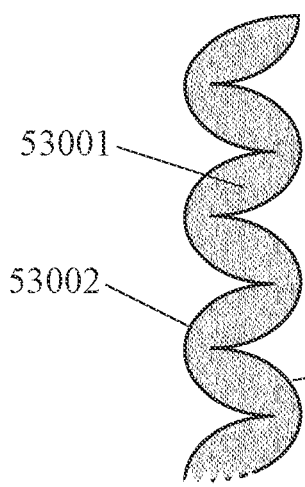
FIGS. 53 and 54 show stand-alone and sac-deployed views of an intrasacular aneurysm occlusion device with two catenary-or-semicircle-sequence wires connected by mesh.
Figure 54:
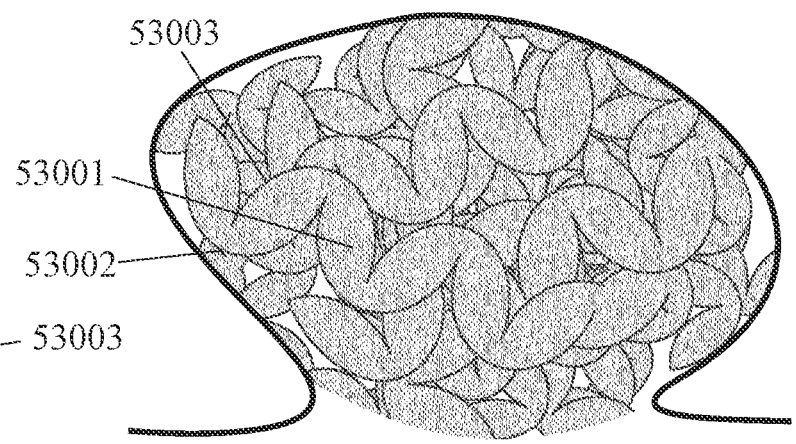

FIGS. 53 and 54 show two sequential views of an aneurysm occlusion device comprising an undulating embolic ribbon 53001 which is configured to be inserted into an aneurysm sac. This undulating embolic ribbon is configured to accumulate into an arcuate three-dimensional occlusive mass which fills the aneurysm sac. In this example, an undulating embolic ribbon further comprises: a first longitudinal series of (pair-wise) connected arcs 53002 comprising a first-side (e.g. left side) perimeter of the ribbon; a second longitudinal series of (pair-wise) connected arcs 53003 comprising a second-side (e.g. right side) perimeter of the ribbon; and an occlusive mesh or fabric between the first longitudinal series and the second longitudinal series.

FIG. 53 shows this device at a first point in time, before it has been inserted into an aneurysm sac. FIG. 54 shows this device at a second point in time, after it has been inserted into an aneurysm sac and accumulated in an overlapping manner into an arcuate three-dimensional occlusive mass which fills the aneurysm sac. In an example, an arcuate three-dimensional occlusive mass formed within an aneurysm sac can have a shape selected from the group consisting of: sphere; ellipsoid; ovaloid; pumpkin; apple; pear; and torus. In an example, an arcuate three-dimensional occlusive mass can also have bulges and bumps which enable it to conform to the walls of an irregularly-shaped aneurysm sac. This is especially important for aneurysms which are not perfectly spherical, ellipsoidal, or ovaloidal.

In an example, an arc can be a semi-circle or other segment of a circle. In an example, an arc can have a centenary shape. In an example, an arc can be a (180-degree) segment of a sinusoidal curve. In an example, a longitudinal series of connected arcs can comprise a wire. In an example, the left and right sides of an embolic ribbon can be comprises of two longitudinal wires, each of which is a longitudinal series of connected arcs. In an example, an embolic ribbon can further comprise a central wire between the two longitudinal wires on the left and right rides of the ribbon. In an example, a central wire can have a sinusoidal or other undulating shape.

In an example, connected arcs within a longitudinal series can be oriented in the same direction. In an example, connected arcs in a longitudinal series can have convexities which face in the same direction. In an example, connected arcs in a first longitudinal series can be convex in a first direction, connected arcs in a second longitudinal series can be convex in a second direction, and the first and second directions can be opposites of each other. In an example, a second longitudinal series of connected arcs can be vertically reflected and phase shifted relative to a first longitudinal series of connected arcs. In an example, this phase shift can be 90 degrees. In an example, this phase shift can be 180 degrees.

In an example, the closest distances between first and second longitudinal series of connected arcs can occur where arcs within a series connect to each other. In this example, the closest distance is greater than zero. In another example, the closest distance can be zero, meaning that the first and second series contact each other. In an example, this device can form and/or comprise a longitudinal series of mesh or fabric segments, wherein the shape of each mesh or fabric segment in the series is selected from the group consisting of: convex lens; football; leaf; flower petal; stylized eye outline; tear drop; oval; and ellipse.

In an example, adjacent mesh or fabric segments in a longitudinal series of mesh or fabric segments can have different orientations. In an example, a series of mesh or fabric segments can have oscillating and/or alternating (e.g. right vs. left) orientations. In an example, a series of mesh or fabric segments can comprise a longitudinal zigzag pattern. In an example, a series of mesh or fabric segments can have longitudinal axes which zigzag relative to each other, forming 90-degree angles where their axes (or extensions thereof in space) intersect. In an example, a series of mesh or fabric segments can have longitudinal axes, wherein their axes (or extensions thereof in space) intersect at angles within the range of 60 to 120 degrees.

In an example, an embolic ribbon can have the same width along its entire length. In an example, a proximal portion of an embolic ribbon can be wider than its distal portion, or vice versa. In an example, an embolic ribbon can have the same thickness along its entire length. In an example, a proximal portion of an embolic ribbon can be thicker than its distal portion, or vice versa. In an example, an embolic ribbon can have the same elasticity level along its entire length. In an example, a proximal portion of an embolic ribbon can be more elastic than its distal portion, or vice versa.

In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, selective application of electromagnetic energy can change the elasticity, flexibility, and/or shape of a left-side portion or a right-side portion of the ribbon. In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, this can enable a user to guide and/or steer an embolic ribbon during deployment so as to create an arcuate three-dimensional occlusive mass which optimally fills an aneurysm sac.

In an example, an embolic ribbon can accumulate within an aneurysm sac so as to form an arcuate three-dimensional occlusive mass, progressively filling it from the outside of the mass to the inside of the mass. In an example, a catheter dispensing an embolic ribbon can be positioned in the center of an aneurysm sac so as to form an arcuate three-dimensional occlusive mass starting from the outside of the mass and then progressively filling the inside.

In an example, an embolic ribbon can accumulate within an aneurysm sac so as to form an arcuate three-dimensional occlusive mass, progressing from the inside of the mass to the outside of the mass, like wrapping a ball of yarn. In an example, a catheter dispensing an embolic ribbon can be positioned near the wall of an aneurysm sac so as to form an arcuate three-dimensional occlusive mass starting from the inside of the mass and then progressively covering the outside, like wrapping a ball of yarn. Relevant design variations discussed elsewhere in this disclosure or in priority-linked disclosures can also be applied to the example shown here.

Figure 55:
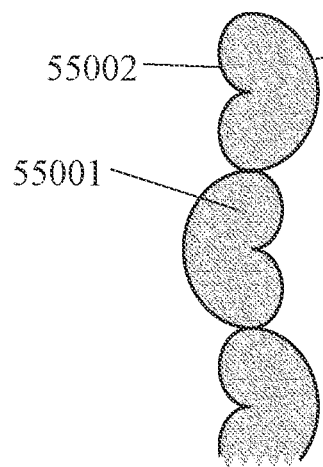
FIGS. 55 and 56 show stand-alone and sac-deployed views of an intrasacular aneurysm occlusion device with cardioid or kidney shaped mesh-filled loops.
Figure 56:
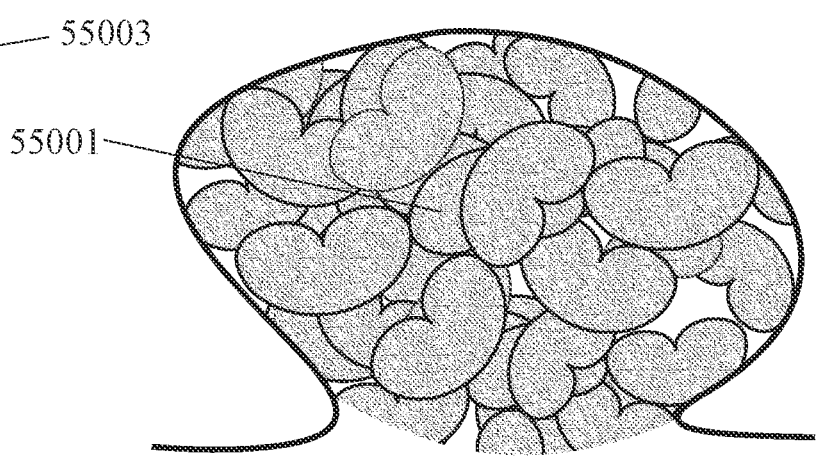

FIGS. 55 and 56 show two sequential views of an aneurysm occlusion device comprising an undulating embolic ribbon which is configured to be inserted into an aneurysm sac. This undulating embolic ribbon is configured to accumulate into an arcuate three-dimensional occlusive mass which fills the aneurysm sac. In an example, this undulating embolic ribbon can be described as comprising a connected longitudinal series of cardioid or kidney shaped mesh or fabric segments, including 55001. In this example, adjacent cardioid or kidney shaped segments face in opposite directions. In an example, this undulating embolic ribbon can be described as comprising: a first wire 55002 comprising a longitudinal series of (pair-wise) connected arcs; a second wire 55003 which is sinusoidal; and an occlusive mesh or fabric between the first wire and the second wire.

FIG. 55 shows this device at a first point in time, before it has been inserted into an aneurysm sac. FIG. 56 shows this device at a second point in time, after it has been inserted into an aneurysm sac and accumulated in an overlapping manner into an arcuate three-dimensional occlusive mass which fills an aneurysm sac. In an example, an arcuate three-dimensional occlusive mass formed within an aneurysm sac can have a shape selected from the group consisting of: sphere; ellipsoid; ovaloid; pumpkin; apple; pear; and torus. In an example, an arcuate three-dimensional occlusive mass can also have bulges and bumps which enable it to conform to the walls of an irregularly-shaped aneurysm sac. This is especially important for aneurysms which are not perfectly spherical, ellipsoidal, or ovaloidal. Relevant design variations discussed elsewhere in this disclosure or in priority-linked disclosures can also be applied to the example shown here.

Figure 57:
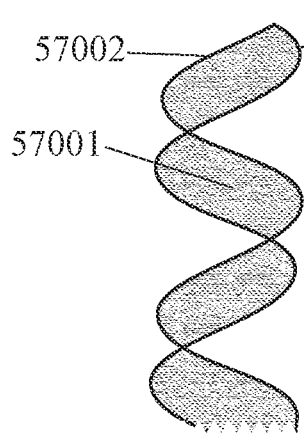
FIGS. 57 and 58 show stand-alone and sac-deployed views of an intrasacular aneurysm occlusion device with two out-of-phase-sinusoidal wires connected by mesh.
Figure 58:
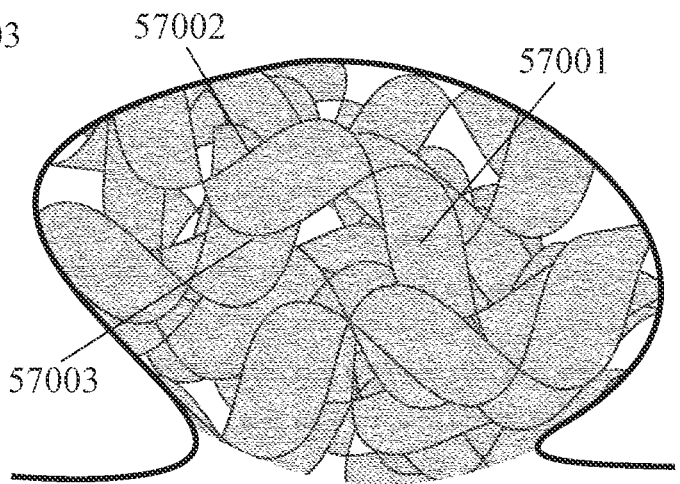

FIGS. 57 and 58 show two sequential views of an aneurysm occlusion device comprising an undulating embolic ribbon 57001 which is configured to be inserted into an aneurysm sac. This undulating embolic ribbon is configured to accumulate into an arcuate three-dimensional occlusive mass which fills the aneurysm sac. In this example, an undulating embolic ribbon further comprises: a first longitudinal sinusoidal wire 57002; a second longitudinal sinusoidal wire 57003, wherein the second longitudinal sinusoidal wire is phase-shifted relative to the first sinusoidal wire; and an occlusive mesh or fabric between the first longitudinal sinusoidal wire and the second longitudinal sinusoidal wire.

In an example, a phase shift between a first longitudinal sinusoidal wire and a second longitudinal sinusoidal wire can be 90 degrees. In an example, a phase shift between a first longitudinal sinusoidal wire and a second longitudinal sinusoidal wire can be between 20 and 160 degrees. In this example, the first longitudinal sinusoidal wire and the second longitudinal sinusoidal wire have the same wavelength. In this example, the first longitudinal sinusoidal wire and the second longitudinal sinusoidal wire have the same amplitude. In this example, the first longitudinal sinusoidal wire and the second longitudinal sinusoidal wire share the same central longitudinal axis. In another example, a first longitudinal sinusoidal wire and a second longitudinal sinusoidal wire can have different wavelengths. In another example, a first longitudinal sinusoidal wire and a second longitudinal sinusoidal wire can have different amplitudes. In another example, a first longitudinal sinusoidal wire and a second longitudinal sinusoidal wire can have different central longitudinal axes.

FIG. 57 shows this device at a first point in time, before it has been inserted into an aneurysm sac. FIG. 58 shows this device at a second point in time, after it has been inserted into an aneurysm sac and accumulated in an overlapping manner into an arcuate three-dimensional occlusive mass which fills the aneurysm sac. In an example, an arcuate three-dimensional occlusive mass formed within an aneurysm sac can have a shape selected from the group consisting of: sphere; ellipsoid; ovaloid; pumpkin; apple; pear; and torus. In an example, an arcuate three-dimensional occlusive mass can also have bulges and bumps which enable it to conform to the walls of an irregularly-shaped aneurysm sac. This is especially important for aneurysms which are not perfectly spherical, ellipsoidal, or ovaloidal.

In an example, an embolic ribbon can have the same width along its entire length. In an example, a proximal portion of an embolic ribbon can be wider than its distal portion, or vice versa. In an example, an embolic ribbon can have the same thickness along its entire length. In an example, a proximal portion of an embolic ribbon can be thicker than its distal portion, or vice versa. In an example, an embolic ribbon can have the same elasticity level along its entire length. In an example, a proximal portion of an embolic ribbon can be more elastic than its distal portion, or vice versa.

In an example, an embolic ribbon can accumulate within an aneurysm sac so as to form an arcuate three-dimensional occlusive mass, progressively filling it from the outside of the mass to the inside of the mass. In an example, a catheter dispensing an embolic ribbon can be positioned in the center of an aneurysm sac so as to form an arcuate three-dimensional occlusive mass starting from the outside of the mass and then progressively filling the inside.

In an example, an embolic ribbon can accumulate within an aneurysm sac so as to form an arcuate three-dimensional occlusive mass, progressing from the inside of the mass to the outside of the mass, like wrapping a ball of yarn. In an example, a catheter dispensing an embolic ribbon can be positioned near the wall of an aneurysm sac so as to form an arcuate three-dimensional occlusive mass starting from the inside of the mass and then progressively covering the outside, like wrapping a ball of yarn. Relevant design variations discussed elsewhere in this disclosure or in priority-linked disclosures can also be applied to the example shown here.

In an example, a device for occluding an aneurysm can comprise: a first longitudinal wire which is inserted into an aneurysm sac; a second longitudinal wire which is inserted into the aneurysm sac, wherein the first and second longitudinal wires intersect, overlap, or connect at least three times along their longitudinal axes, forming at least two wire loops between the first and second longitudinal wires; and a mesh material which spans the at least two loops. In an example, a device for occluding an aneurysm can comprise: a first longitudinal wire which is inserted into an aneurysm sac; a second longitudinal wire which is inserted into the aneurysm sac, wherein the first and second longitudinal wires converge and diverge at least three times along their longitudinal axes, forming at least two arcuate areas between the first and second longitudinal wires; and a mesh material which spans the at least two arcuate areas.

In an example, the first and second longitudinal wires can be undulating or sinusoidal. In an example, the first and second longitudinal wires can be sinusoidal and out-of-phase with each other. In an example, the device can further comprise a third longitudinal wire between the first and second longitudinal wires. In an example, the third longitudinal wire can be undulating or sinusoidal. In an example, the third longitudinal wire can be sinusoidal and out-of-phase with the first and second longitudinal wires. In an example, the device can be asymmetric with respect to its longitudinal axis. In an example, the device can be asymmetric with respect to its longitudinal axis and there is alternating side-to-side variation in this longitudinal asymmetry in different locations along its longitudinal axis.

Figure 59:
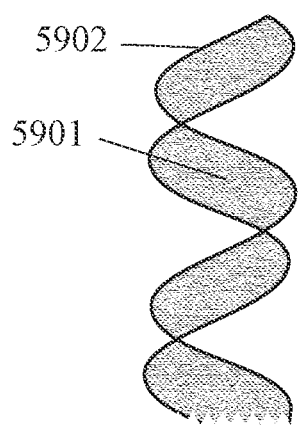
FIGS. 59 and 60 show stand-alone and sac-deployed views of an intrasacular aneurysm occlusion device comprising a ribbon with the same size loops along the length of the ribbon.
Figure 60:
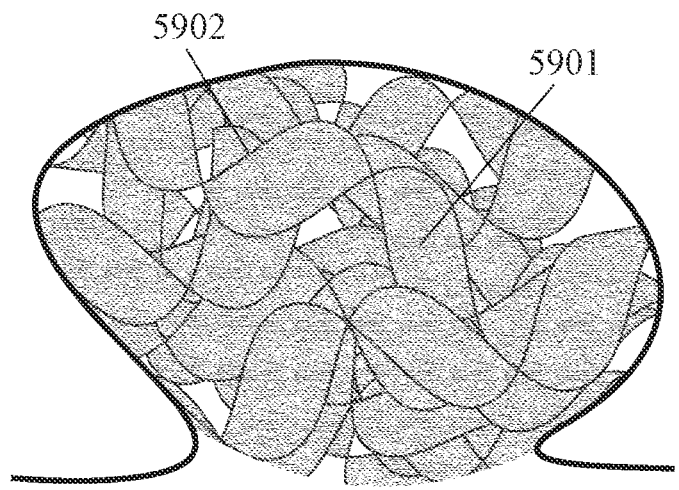

FIGS. 59 and 60 show two sequential views of another example of an intrasacular aneurysm occlusion device comprising a longitudinal mesh ribbon with a proximal-to-distal series of loops (and/or segments). The longitudinal mesh ribbon has a longitudinal series of loops (and/or segments), including first loop 5901 and second loop 5902, wherein the second loop is more distal than the first loop and, correspondingly, the first loop is more proximal than the second loop. In this example, the loops (and/or segments) in the series of loops all have the same length, width, and inter-loop (e.g. inter-segment) connection angle or curvature along the entire length of the ribbon. The ribbon is inserted into an aneurysm, where it accumulates and overlaps onto itself to form an arcuate three-dimensional occlusive mass which fills the aneurysm sac. In an example, the ribbon can progressively fill the aneurysm sac in an outer-layer to an inner-core progression. FIG. 59 shows this ribbon at a first point in time, before it has been inserted into an aneurysm sac. FIG. 60 shows this device at a second point in time, after it has been inserted into an aneurysm sac and accumulated in an overlapping manner into an arcuate three-dimensional occlusive mass which fills the aneurysm sac.

In an example, a longitudinal (distal-to-proximal) series of loops (and/or segments) in a longitudinal mesh ribbon can all have the same length, the same width, and the same inter-loop connection angle or curvature along the entire (distal-to-proximal) length of the ribbon. Alternatively, proximal loops (and/or segments) can have different lengths, widths, and/or inter-loop (inter-segment) connection angles or curvatures than distal loops on a longitudinal mesh ribbon. In an example, a longitudinal series of loops (and/or segments) in a longitudinal mesh ribbon can have different lengths, widths, and/or inter-loop (inter-segment) connection angles or curvatures along the distal-to-proximal length of the ribbon. In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form a better three-dimensional occlusive mass within an aneurysm sac.

In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form a denser three-dimensional occlusive mass within an aneurysm sac. In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form a generally-globular, spherical, and/or ellipsoidal three-dimensional occlusive mass within an aneurysm sac. In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form an irregularly-shaped three-dimensional occlusive mass which conforms to the walls of even an irregularly-shaped aneurysm sac.

In an example, proximal loops (and/or segments) can have a smaller lengths, widths, and/or inter-loop (inter-segment) connection angles or curvatures than distal loops in a longitudinal mesh ribbon. In an example, a longitudinal series of loops (and/or segments) in a longitudinal mesh ribbon can have progressively-smaller lengths, widths, and/or inter-loop connection angles or curvatures in a distal-to-proximal sequence along the length of the ribbon. In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form a better three-dimensional occlusive mass within an aneurysm sac. In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form a denser three-dimensional occlusive mass within an aneurysm sac.

In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form a generally-globular, spherical, and/or ellipsoidal three-dimensional occlusive mass within an aneurysm sac. In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form an irregularly-shaped three-dimensional occlusive mass which conforms to the walls of even an irregularly-shaped aneurysm sac.

In an example, loops (and/or segments) of a mesh ribbon can become smaller and smaller along the length of the ribbon to better fill the central space of an aneurysm sac. In an example, loops (and/or segments) can be arranged in a distal-to-proximal sequence of decreasing size, especially if they are configured to form a sphere by accumulation of mass in an outside-to-inside manner within a sphere. In an example, a distal (outer-placed) loop (and/or segment) in distal-to-proximal sequence of loops (and/or segments) can be larger than a proximal (inner-placed) loop (and/or segment) in that sequence. In an example, the most distal connections can be spaced to form loops which span the entire circumference of the aneurysm sac but successive loops can become smaller and smaller to better fill the central space of the aneurysm sac. In an example, loops (and/or segments) can be arranged in distal-to-proximal sequence of decreasing size, especially if they are configured to form a sphere by accumulation of mass in an outside-to-inside manner within a sphere.

In an example, pairs of loops (and/or segments) can be connected to each other at different angles (relative to a longitudinal axis of a device). In an example, a distal-to-proximal sequence of loops (and/or segments) can be connected to each other at a progressive sequence of angles. In an example, a distal-to-proximal sequence of loops (and/or segments) can be connected to each other with distal-to-proximally-decreasing angle degrees so that the loops (and/or segments) are biased to form a sphere, ellipsoid, or other three-dimensional mass upon insertion into an aneurysm sac. In an example, a distal-to-proximal sequence of loop sections can be connected to each other with distal-to-proximally-decreasing angle degrees so that the loops (and/or segments) are biased to form a sphere, ellipsoid, or other three-dimensional mass upon insertion into an aneurysm sac.

In an example, a longitudinal (distal-to-proximal) series of loops (and/or segments) in a longitudinal mesh ribbon can all have the same thickness, density, porosity, elasticity, stiffness, flexibility, and/or durometer along the entire (distal-to-proximal) length of the ribbon. Alternatively, proximal loops (and/or segments) can have different thicknesses, densities, porosities, elasticity levels, stiffness levels, flexibility levels, and/or durometers than distal loops in a longitudinal mesh ribbon. In an example, proximal loops (and/or segments) can be less thick, less dense, more porous, more elastic, less stiff, more flexible, and/or lower durometer than distal loops in a longitudinal mesh ribbon. In an example, a longitudinal series of loops (and/or segments) in a longitudinal mesh ribbon can have different thicknesses, densities, porosities, elasticity levels, stiffness levels, flexibility levels, and/or durometers along the distal-to-proximal length of the ribbon.

In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form a better three-dimensional occlusive mass within an aneurysm sac. In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form a denser three-dimensional occlusive mass within an aneurysm sac.

In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form a generally-globular, spherical, and/or ellipsoidal three-dimensional occlusive mass within an aneurysm sac. In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form an irregularly-shaped three-dimensional occlusive mass which conforms to the walls of even an irregularly-shaped aneurysm sac. Alternatively, distal loops (and/or segments) can be less thick, less dense, more porous, more elastic, less stiff, more flexible, and/or lower durometer than proximal loops in a longitudinal mesh ribbon.

In an example, a distal-to-proximal sequence of loops (and/or segments) can be connected to each other with a distal-to-proximal sequence of alternating (greater, then lower) angle degrees so that the loops (and/or segments) are biased to form a spherical, elliptical, or other arcuate mass upon insertion into an aneurysm sac. In an example, a proximal portion of an embolic ribbon can be more elastic than its distal portion, or vice versa. In an example, a proximal portion of an embolic ribbon can be thicker than its distal portion, or vice versa. In another example, a proximal portion of an embolic ribbon can be wider than its distal portion, or vice versa.

In an example, a device user can remotely change the density of a distal loop (and/or segment) relative to that of a proximal loop (and/or segment) in a longitudinal embolic ribbon during deployment of the ribbon into an aneurysm sac. In an example, a device user can remotely change the density of a loop (and/or segment) of a longitudinal embolic ribbon during deployment of the ribbon into an aneurysm sac. In an example, a device user can remotely change the density of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the durometer of a distal loop (and/or segment) relative to that of a proximal loop (and/or segment) in a longitudinal embolic ribbon during deployment of the ribbon into an aneurysm sac. In an example, a device user can remotely change the durometer of a loop (and/or segment) of a longitudinal embolic ribbon during deployment of the ribbon into an aneurysm sac. In an example, a device user can remotely change the durometer of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the elasticity of a distal loop (and/or segment) relative to that of a proximal loop (and/or segment) in a longitudinal embolic ribbon during deployment of the ribbon into an aneurysm sac. In an example, a device user can remotely change the elasticity of a loop (and/or segment) of a longitudinal embolic ribbon during deployment of the ribbon into an aneurysm sac. In an example, a device user can remotely change the elasticity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the flexibility of a distal loop (and/or segment) relative to that of a proximal loop (and/or segment) in a longitudinal embolic ribbon during deployment of the ribbon into an aneurysm sac. In an example, a device user can remotely change the flexibility of a loop (and/or segment) of a longitudinal embolic ribbon during deployment of the ribbon into an aneurysm sac. In an example, a device user can remotely change the flexibility of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac. In an example, a device user can remotely change the inter-loop (inter-segment) connection angle or curvature of a loop (and/or segment) of a longitudinal embolic ribbon during deployment of the ribbon into an aneurysm sac. In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the length of a distal loop (and/or segment) relative to that of a proximal loop (and/or segment) in a longitudinal embolic ribbon during deployment of the ribbon into an aneurysm sac. In an example, a device user can remotely change the length of a loop (and/or segment) of a longitudinal embolic ribbon during deployment of the ribbon into an aneurysm sac. In an example, a device user can remotely change the length of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the porosity of a distal loop (and/or segment) relative to that of a proximal loop (and/or segment) in a longitudinal embolic ribbon during deployment of the ribbon into an aneurysm sac. In an example, a device user can remotely change the porosity of a loop (and/or segment) of a longitudinal embolic ribbon during deployment of the ribbon into an aneurysm sac. In an example, a device user can remotely change the porosity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the stiffness of a distal loop (and/or segment) relative to that of a proximal loop (and/or segment) in a longitudinal embolic ribbon during deployment of the ribbon into an aneurysm sac. In an example, a device user can remotely change the stiffness of a loop (and/or segment) of a longitudinal embolic ribbon during deployment of the ribbon into an aneurysm sac. In an example, a device user can remotely change the stiffness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the thickness of a distal loop (and/or segment) relative to that of a proximal loop (and/or segment) in a longitudinal embolic ribbon during deployment of the ribbon into an aneurysm sac. In an example, a device user can remotely change the thickness of a loop (and/or segment) of a longitudinal embolic ribbon during deployment of the ribbon into an aneurysm sac. In an example, a device user can remotely change the thickness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the width of a distal loop (and/or segment) relative to that of a proximal loop (and/or segment) in a longitudinal embolic ribbon during deployment of the ribbon into an aneurysm sac. In an example, a device user can remotely change the width of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon. In an example, a device user can remotely change the width of a loop (and/or segment) of a longitudinal embolic ribbon during deployment of the ribbon into an aneurysm sac.

In an example, a user can adjust the cross-sectional asymmetry of an embolic ribbon by adjusting its elasticity, flexibility, shape, length, and/or width as it is deployed within an aneurysm sac. In an example, the cross-sectional symmetry of an embolic ribbon can be adjusted by a user in real-time (as an embolic ribbon is being inserted into an aneurysm sac) so as to guide and/or steer the bending movement of the ribbon as it is deployed. In an example, the direction in which one loop (and/or segment) of this device moves relative to another loop (and/or segment) as the sections are inserted into an aneurysm can be steered, changed, and/or adjusted by a user in real time. In an example, the orientation of one loop (and/or segment) relative to another loop (and/or segment) can be steered and/or adjusted in real time as the sections are inserted into an aneurysm.

In an example, a progression of sizes and/or widths of a series of multiple loops (and/or segments) can be adjusted, controlled, and/or varied in real time by a person deploying them in order to best match the contours of a specific aneurysm sac. In an example, a progression of sizes and/or widths of a series of multiple loops (and/or segments) can be adjusted, controlled, and/or varied in real time by a person deploying them in order to best fill a specific aneurysm sac. This enables a user to guide the formation of an arcuate three-dimensional occlusive mass which confirms to the walls of an irregularly-shaped aneurysm sac.

In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first loop (and/or segment) and/or to a second loop (and/or segment) can change the cross-sectional asymmetry of an embolic ribbon, thereby biasing the embolic ribbon to bend to the right or to the left. In an example, selective application of electromagnetic energy can change the elasticity, flexibility, and/or shape of a left-side portion or a right-side portion of the ribbon.

In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, this device can further comprise an electromagnetic energy source which enables a user to selectively apply electromagnetic energy to a portion of an embolic ribbon as the ribbon is deployed within an aneurysm sac. In an example, application of electromagnetic energy to a portion of an embolic ribbon can change the size, shape, and/or orientation of one or more loops in the ribbon by expanding or contracting one or more wires in the ribbon. In an example, application of electromagnetic energy to a portion of an embolic ribbon can change the size, shape, and/or orientation of one or more loops in the ribbon by detaching one or more wires in the ribbon.

In an example, differential pulling on left-side vs. right-side pull-cords can bias the longitudinal axis of connected loops (and/or segments) into curvature as these segments are inserted into an aneurysm. In an example, pulling or pushing a wire connected to the first loop (and/or segment) or connected to the second loop (and/or segment) can bias the embolic ribbon to bend to the right or to the left. In an example, this curvature can cause connected segments to accumulate into a spherical, elliptical, or other arcuate mass which occludes the aneurysm. In an example, the orientation of one loop (and/or segment) relative to another loop (and/or segment) can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections.

In an example, successive loops and/or wide longitudinal segments can become smaller to better fill the central space of an aneurysm sac. In an example, the most distal connections can be spaced to form loops which span the entire circumference of the aneurysm sac but successive loops can become smaller and smaller to better fill the central space of the aneurysm sac. In an example, wide longitudinal segments can be arranged in distal-to-proximal sequence of decreasing size, especially if they are configured to form a sphere by accumulation of mass in an outside-to-inside manner within a sphere. In an example, a distal (outer-placed) segment in distal-to-proximal sequence of wide longitudinal segments can be larger than a proximal (inner-placed) segment in that sequence.

In an example, a distal-to-proximal sequence of longitudinal sections can be connected to each other at a progressive sequence of angles. In an example, a distal-to-proximal sequence of longitudinal sections can be connected to each other with distal-to-proximally-decreasing angle degrees so that the longitudinal sections are biased to form a sphere, ellipsoid, or other three-dimensional mass upon insertion into an aneurysm sac. In an example, a distal-to-proximal sequence of longitudinal sections can be connected to each other with a distal-to-proximal sequence of alternating (greater, then lower) angle degrees so that the longitudinal sections are biased to form a spherical, elliptical, or other arcuate mass upon insertion into an aneurysm sac. In an example, pairs of longitudinal sections can be connected to each other at different angles (relative to a longitudinal axis of a device).

In an example, the progression of sizes and/or widths of a series of multiple shape-changing embolic members can be adjusted, controlled, and/or varied in real time by a person deploying them in order to best match the contours of a specific aneurysm sac. In an example, the progression of sizes and/or widths of a series of multiple shape-changing embolic members can be adjusted, controlled, and/or varied in real time by a person deploying them in order to best fill a specific aneurysm sac. In an example, the direction in which one longitudinal section of this device moves relative to another longitudinal section as the sections are inserted into an aneurysm can be steered, changed, and/or adjusted by a user in real time. In an example, the orientation of one longitudinal section relative to another longitudinal section can be steered and/or adjusted in real time as the sections are inserted into an aneurysm. In an example, the cross-sectional symmetry of an undulating embolic ribbon can be adjusted by a user in real-time (as an embolic ribbon is being inserted into an aneurysm sac) so as to guide and/or steer the bending movement of the ribbon as it is deployed. This enables a user to guide the formation of an arcuate three-dimensional occlusive mass which confirms to the walls of an irregularly-shaped aneurysm sac. In an example, a user can adjust the cross-sectional asymmetry of an undulating embolic ribbon by adjusting its elasticity, flexibility, shape, length, and/or width as it is deployed within an aneurysm sac.

In an example, this device can further comprise an electromagnetic energy source which enables a user to selectively apply electromagnetic energy to a portion of an embolic ribbon as the ribbon is deployed within an aneurysm sac. In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first undulating strip and/or to a second undulating strip can change the cross-sectional asymmetry of the undulating embolic ribbon, thereby biasing the embolic ribbon to bend to the right or to the left. In an example, selective application of electromagnetic energy can change the elasticity, flexibility, and/or shape of a left-side portion or a right-side portion of the ribbon. In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, differential pulling on left-side vs. right-side pull-cords can bias the longitudinal axis of connected segments into curvature as these segments are inserted into an aneurysm. In an example, this curvature can cause connected segments to accumulate into a spherical, elliptical, or other arcuate mass which occludes the aneurysm. In an example, pulling or pushing a wire connected to the first undulating strip or connected to the second undulating strip can bias the undulating embolic ribbon to bend to the right or to the left. In an example, the orientation of one longitudinal section relative to another longitudinal section can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections. Relevant variations discussed elsewhere in this or prior-linked disclosures can also be applied to this example.

Figure 61:
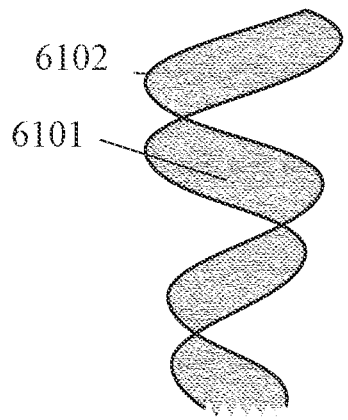
FIGS. 61 and 62 show stand-alone and sac-deployed views of an intrasacular aneurysm occlusion device comprising a ribbon wherein more distal loops are larger than more proximal loops.
Figure 62:
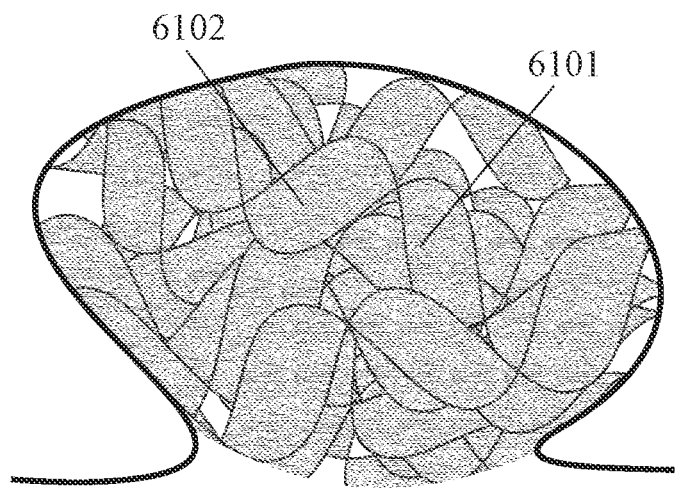

FIGS. 61 and 62 show two sequential views of another example of an intrasacular aneurysm occlusion device comprising a longitudinal mesh ribbon with a proximal-to-distal series of loops (and/or segments). The longitudinal mesh ribbon has a longitudinal series of loops (and/or segments), including first loop 6101 and second loop 6202, wherein the second loop is more distal than the first loop and, correspondingly, the first loop is more proximal than the second loop. In this example, more distal loops (and/or segments) in the series of loops have a greater length and/or width than more proximal loops along the length of the ribbon. The ribbon is inserted into an aneurysm, where it accumulates and overlaps onto itself into an arcuate three-dimensional occlusive mass which fills the aneurysm sac. In an example, the ribbon can progressively fill the aneurysm sac in an outer-layer to inner-core progression. FIG. 61 shows this ribbon at a first point in time, before it has been inserted into an aneurysm sac. FIG. 62 shows this device at a second point in time, after it has been inserted into an aneurysm sac and accumulated in an overlapping manner into an arcuate three-dimensional occlusive mass which fills the aneurysm sac.

In an example, a longitudinal (distal-to-proximal) series of loops (and/or segments) in a longitudinal mesh ribbon can all have the same length, the same width, and the same inter-loop connection angle or curvature along the entire (distal-to-proximal) length of the ribbon. Alternatively, proximal loops (and/or segments) can have different lengths, widths, and/or inter-loop (inter-segment) connection angles or curvatures than distal loops on a longitudinal mesh ribbon. In an example, a longitudinal series of loops (and/or segments) in a longitudinal mesh ribbon can have different lengths, widths, and/or inter-loop (inter-segment) connection angles or curvatures along the distal-to-proximal length of the ribbon. In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form a better three-dimensional occlusive mass within an aneurysm sac.

In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form a denser three-dimensional occlusive mass within an aneurysm sac. In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form a generally-globular, spherical, and/or ellipsoidal three-dimensional occlusive mass within an aneurysm sac. In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form an irregularly-shaped three-dimensional occlusive mass which conforms to the walls of even an irregularly-shaped aneurysm sac.

In an example, proximal loops (and/or segments) can have a smaller lengths, widths, and/or inter-loop (inter-segment) connection angles or curvatures than distal loops in a longitudinal mesh ribbon. In an example, a longitudinal series of loops (and/or segments) in a longitudinal mesh ribbon can have progressively-smaller lengths, widths, and/or inter-loop connection angles or curvatures in a distal-to-proximal sequence along the length of the ribbon. In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form a better three-dimensional occlusive mass within an aneurysm sac. In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form a denser three-dimensional occlusive mass within an aneurysm sac.

In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form a generally-globular, spherical, and/or ellipsoidal three-dimensional occlusive mass within an aneurysm sac. In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form an irregularly-shaped three-dimensional occlusive mass which conforms to the walls of even an irregularly-shaped aneurysm sac.

In an example, loops (and/or segments) of a mesh ribbon can become smaller and smaller along the length of the ribbon to better fill the central space of an aneurysm sac. In an example, loops (and/or segments) can be arranged in a distal-to-proximal sequence of decreasing size, especially if they are configured to form a sphere by accumulation of mass in an outside-to-inside manner within a sphere. In an example, a distal (outer-placed) loop (and/or segment) in distal-to-proximal sequence of loops (and/or segments) can be larger than a proximal (inner-placed) loop (and/or segment) in that sequence. In an example, the most distal connections can be spaced to form loops which span the entire circumference of the aneurysm sac but successive loops can become smaller and smaller to better fill the central space of the aneurysm sac. In an example, loops (and/or segments) can be arranged in distal-to-proximal sequence of decreasing size, especially if they are configured to form a sphere by accumulation of mass in an outside-to-inside manner within a sphere.

In an example, pairs of loops (and/or segments) can be connected to each other at different angles (relative to a longitudinal axis of a device). In an example, a distal-to-proximal sequence of loops (and/or segments) can be connected to each other at a progressive sequence of angles. In an example, a distal-to-proximal sequence of loops (and/or segments) can be connected to each other with distal-to-proximally-decreasing angle degrees so that the loops (and/or segments) are biased to form a sphere, ellipsoid, or other three-dimensional mass upon insertion into an aneurysm sac. In an example, a distal-to-proximal sequence of loop sections can be connected to each other with distal-to-proximally-decreasing angle degrees so that the loops (and/or segments) are biased to form a sphere, ellipsoid, or other three-dimensional mass upon insertion into an aneurysm sac.

In an example, a longitudinal (distal-to-proximal) series of loops (and/or segments) in a longitudinal mesh ribbon can all have the same thickness, density, porosity, elasticity, stiffness, flexibility, and/or durometer along the entire (distal-to-proximal) length of the ribbon. Alternatively, proximal loops (and/or segments) can have different thicknesses, densities, porosities, elasticity levels, stiffness levels, flexibility levels, and/or durometers than distal loops in a longitudinal mesh ribbon. In an example, proximal loops (and/or segments) can be less thick, less dense, more porous, more elastic, less stiff, more flexible, and/or lower durometer than distal loops in a longitudinal mesh ribbon. In an example, a longitudinal series of loops (and/or segments) in a longitudinal mesh ribbon can have different thicknesses, densities, porosities, elasticity levels, stiffness levels, flexibility levels, and/or durometers along the distal-to-proximal length of the ribbon.

In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form a better three-dimensional occlusive mass within an aneurysm sac. In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form a denser three-dimensional occlusive mass within an aneurysm sac.

In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form a generally-globular, spherical, and/or ellipsoidal three-dimensional occlusive mass within an aneurysm sac.

In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form an irregularly-shaped three-dimensional occlusive mass which conforms to the walls of even an irregularly-shaped aneurysm sac. Alternatively, distal loops (and/or segments) can be less thick, less dense, more porous, more elastic, less stiff, more flexible, and/or lower durometer than proximal loops in a longitudinal mesh ribbon.

In an example, a distal-to-proximal sequence of loops (and/or segments) can be connected to each other with a distal-to-proximal sequence of alternating (greater, then lower) angle degrees so that the loops (and/or segments) are biased to form a spherical, elliptical, or other arcuate mass upon insertion into an aneurysm sac. In an example, a proximal portion of an embolic ribbon can be more elastic than its distal portion, or vice versa. In an example, a proximal portion of an embolic ribbon can be thicker than its distal portion, or vice versa. In another example, a proximal portion of an embolic ribbon can be wider than its distal portion, or vice versa.

In an example, a device user can remotely change the density of a distal loop (and/or segment) relative to that of a proximal loop (and/or segment) in a longitudinal embolic ribbon during deployment of the ribbon into an aneurysm sac. In an example, a device user can remotely change the density of a loop (and/or segment) of a longitudinal embolic ribbon during deployment of the ribbon into an aneurysm sac. In an example, a device user can remotely change the density of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the durometer of a distal loop (and/or segment) relative to that of a proximal loop (and/or segment) in a longitudinal embolic ribbon during deployment of the ribbon into an aneurysm sac. In an example, a device user can remotely change the durometer of a loop (and/or segment) of a longitudinal embolic ribbon during deployment of the ribbon into an aneurysm sac. In an example, a device user can remotely change the durometer of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the elasticity of a distal loop (and/or segment) relative to that of a proximal loop (and/or segment) in a longitudinal embolic ribbon during deployment of the ribbon into an aneurysm sac. In an example, a device user can remotely change the elasticity of a loop (and/or segment) of a longitudinal embolic ribbon during deployment of the ribbon into an aneurysm sac. In an example, a device user can remotely change the elasticity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the flexibility of a distal loop (and/or segment) relative to that of a proximal loop (and/or segment) in a longitudinal embolic ribbon during deployment of the ribbon into an aneurysm sac. In an example, a device user can remotely change the flexibility of a loop (and/or segment) of a longitudinal embolic ribbon during deployment of the ribbon into an aneurysm sac. In an example, a device user can remotely change the flexibility of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac. In an example, a device user can remotely change the inter-loop (inter-segment) connection angle or curvature of a loop (and/or segment) of a longitudinal embolic ribbon during deployment of the ribbon into an aneurysm sac. In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the length of a distal loop (and/or segment) relative to that of a proximal loop (and/or segment) in a longitudinal embolic ribbon during deployment of the ribbon into an aneurysm sac. In an example, a device user can remotely change the length of a loop (and/or segment) of a longitudinal embolic ribbon during deployment of the ribbon into an aneurysm sac. In an example, a device user can remotely change the length of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the porosity of a distal loop (and/or segment) relative to that of a proximal loop (and/or segment) in a longitudinal embolic ribbon during deployment of the ribbon into an aneurysm sac. In an example, a device user can remotely change the porosity of a loop (and/or segment) of a longitudinal embolic ribbon during deployment of the ribbon into an aneurysm sac. In an example, a device user can remotely change the porosity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the stiffness of a distal loop (and/or segment) relative to that of a proximal loop (and/or segment) in a longitudinal embolic ribbon during deployment of the ribbon into an aneurysm sac. In an example, a device user can remotely change the stiffness of a loop (and/or segment) of a longitudinal embolic ribbon during deployment of the ribbon into an aneurysm sac. In an example, a device user can remotely change the stiffness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the thickness of a distal loop (and/or segment) relative to that of a proximal loop (and/or segment) in a longitudinal embolic ribbon during deployment of the ribbon into an aneurysm sac. In an example, a device user can remotely change the thickness of a loop (and/or segment) of a longitudinal embolic ribbon during deployment of the ribbon into an aneurysm sac. In an example, a device user can remotely change the thickness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the width of a distal loop (and/or segment) relative to that of a proximal loop (and/or segment) in a longitudinal embolic ribbon during deployment of the ribbon into an aneurysm sac. In an example, a device user can remotely change the width of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon. In an example, a device user can remotely change the width of a loop (and/or segment) of a longitudinal embolic ribbon during deployment of the ribbon into an aneurysm sac.

In an example, a user can adjust the cross-sectional asymmetry of an embolic ribbon by adjusting its elasticity, flexibility, shape, length, and/or width as it is deployed within an aneurysm sac. In an example, the cross-sectional symmetry of an embolic ribbon can be adjusted by a user in real-time (as an embolic ribbon is being inserted into an aneurysm sac) so as to guide and/or steer the bending movement of the ribbon as it is deployed. In an example, the direction in which one loop (and/or segment) of this device moves relative to another loop (and/or segment) as the sections are inserted into an aneurysm can be steered, changed, and/or adjusted by a user in real time. In an example, the orientation of one loop (and/or segment) relative to another loop (and/or segment) can be steered and/or adjusted in real time as the sections are inserted into an aneurysm.

In an example, a progression of sizes and/or widths of a series of multiple loops (and/or segments) can be adjusted, controlled, and/or varied in real time by a person deploying them in order to best match the contours of a specific aneurysm sac. In an example, a progression of sizes and/or widths of a series of multiple loops (and/or segments) can be adjusted, controlled, and/or varied in real time by a person deploying them in order to best fill a specific aneurysm sac. This enables a user to guide the formation of an arcuate three-dimensional occlusive mass which confirms to the walls of an irregularly-shaped aneurysm sac.

In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first loop (and/or segment) and/or to a second loop (and/or segment) can change the cross-sectional asymmetry of an embolic ribbon, thereby biasing the embolic ribbon to bend to the right or to the left. In an example, selective application of electromagnetic energy can change the elasticity, flexibility, and/or shape of a left-side portion or a right-side portion of the ribbon.

In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, this device can further comprise an electromagnetic energy source which enables a user to selectively apply electromagnetic energy to a portion of an embolic ribbon as the ribbon is deployed within an aneurysm sac. In an example, application of electromagnetic energy to a portion of an embolic ribbon can change the size, shape, and/or orientation of one or more loops in the ribbon by expanding or contracting one or more wires in the ribbon. In an example, application of electromagnetic energy to a portion of an embolic ribbon can change the size, shape, and/or orientation of one or more loops in the ribbon by detaching one or more wires in the ribbon.

In an example, differential pulling on left-side vs. right-side pull-cords can bias the longitudinal axis of connected loops (and/or segments) into curvature as these segments are inserted into an aneurysm. In an example, pulling or pushing a wire connected to the first loop (and/or segment) or connected to the second loop (and/or segment) can bias the embolic ribbon to bend to the right or to the left. In an example, this curvature can cause connected segments to accumulate into a spherical, elliptical, or other arcuate mass which occludes the aneurysm. In an example, the orientation of one loop (and/or segment) relative to another loop (and/or segment) can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections.

In an example, successive loops and/or wide longitudinal segments can become smaller to better fill the central space of an aneurysm sac. In an example, the most distal connections can be spaced to form loops which span the entire circumference of the aneurysm sac but successive loops can become smaller and smaller to better fill the central space of the aneurysm sac. In an example, wide longitudinal segments can be arranged in distal-to-proximal sequence of decreasing size, especially if they are configured to form a sphere by accumulation of mass in an outside-to-inside manner within a sphere. In an example, a distal (outer-placed) segment in distal-to-proximal sequence of wide longitudinal segments can be larger than a proximal (inner-placed) segment in that sequence.

In an example, a distal-to-proximal sequence of longitudinal sections can be connected to each other at a progressive sequence of angles. In an example, a distal-to-proximal sequence of longitudinal sections can be connected to each other with distal-to-proximally-decreasing angle degrees so that the longitudinal sections are biased to form a sphere, ellipsoid, or other three-dimensional mass upon insertion into an aneurysm sac. In an example, a distal-to-proximal sequence of longitudinal sections can be connected to each other with a distal-to-proximal sequence of alternating (greater, then lower) angle degrees so that the longitudinal sections are biased to form a spherical, elliptical, or other arcuate mass upon insertion into an aneurysm sac. In an example, pairs of longitudinal sections can be connected to each other at different angles (relative to a longitudinal axis of a device).

In an example, the progression of sizes and/or widths of a series of multiple shape-changing embolic members can be adjusted, controlled, and/or varied in real time by a person deploying them in order to best match the contours of a specific aneurysm sac. In an example, the progression of sizes and/or widths of a series of multiple shape-changing embolic members can be adjusted, controlled, and/or varied in real time by a person deploying them in order to best fill a specific aneurysm sac. In an example, the direction in which one longitudinal section of this device moves relative to another longitudinal section as the sections are inserted into an aneurysm can be steered, changed, and/or adjusted by a user in real time. In an example, the orientation of one longitudinal section relative to another longitudinal section can be steered and/or adjusted in real time as the sections are inserted into an aneurysm. In an example, the cross-sectional symmetry of an undulating embolic ribbon can be adjusted by a user in real-time (as an embolic ribbon is being inserted into an aneurysm sac) so as to guide and/or steer the bending movement of the ribbon as it is deployed. This enables a user to guide the formation of an arcuate three-dimensional occlusive mass which confirms to the walls of an irregularly-shaped aneurysm sac. In an example, a user can adjust the cross-sectional asymmetry of an undulating embolic ribbon by adjusting its elasticity, flexibility, shape, length, and/or width as it is deployed within an aneurysm sac.

In an example, this device can further comprise an electromagnetic energy source which enables a user to selectively apply electromagnetic energy to a portion of an embolic ribbon as the ribbon is deployed within an aneurysm sac. In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first undulating strip and/or to a second undulating strip can change the cross-sectional asymmetry of the undulating embolic ribbon, thereby biasing the embolic ribbon to bend to the right or to the left. In an example, selective application of electromagnetic energy can change the elasticity, flexibility, and/or shape of a left-side portion or a right-side portion of the ribbon. In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, differential pulling on left-side vs. right-side pull-cords can bias the longitudinal axis of connected segments into curvature as these segments are inserted into an aneurysm. In an example, this curvature can cause connected segments to accumulate into a spherical, elliptical, or other arcuate mass which occludes the aneurysm. In an example, pulling or pushing a wire connected to the first undulating strip or connected to the second undulating strip can bias the undulating embolic ribbon to bend to the right or to the left. In an example, the orientation of one longitudinal section relative to another longitudinal section can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections. Relevant variations discussed elsewhere in this or prior-linked disclosures can also be applied to this example.

Figure 63:
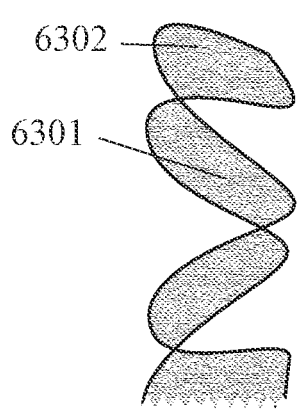
FIGS. 63 and 64 show stand-alone and sac-deployed views of an intrasacular aneurysm occlusion device comprising a ribbon wherein inter-loop connection angles or curvatures are larger for more distal loops than for more proximal loops.
Figure 64:
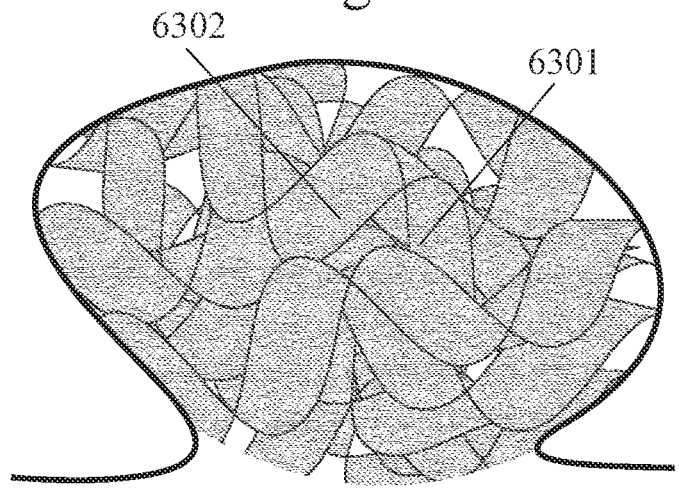

FIGS. 63 and 64 show two sequential views of another example of an intrasacular aneurysm occlusion device comprising a longitudinal mesh ribbon with a proximal-to-distal series of loops (and/or segments). The longitudinal mesh ribbon has a longitudinal series of loops (and/or segments), including first loop 6301 and second loop 6302, wherein the second loop is more distal than the first loop and, correspondingly, the first loop is more proximal than the second loop. In this example, more distal loops (and/or segments) in the series of loops have greater inter-loop (e.g. inter-segment) connection angles or curvatures than more proximal loops along the length of the ribbon. The ribbon is inserted into an aneurysm, where it accumulates and overlaps onto itself into an arcuate three-dimensional occlusive mass which fills the aneurysm sac. In an example, the ribbon can progressively fill the aneurysm sac in an outer-layer to inner-core progression. FIG. 63 shows this ribbon at a first point in time, before it has been inserted into an aneurysm sac. FIG. 64 shows this device at a second point in time, after it has been inserted into an aneurysm sac and accumulated in an overlapping manner into an arcuate three-dimensional occlusive mass which fills the aneurysm sac.

In an example, a longitudinal (distal-to-proximal) series of loops (and/or segments) in a longitudinal mesh ribbon can all have the same length, the same width, and the same inter-loop connection angle or curvature along the entire (distal-to-proximal) length of the ribbon. Alternatively, proximal loops (and/or segments) can have different lengths, widths, and/or inter-loop (inter-segment) connection angles or curvatures than distal loops on a longitudinal mesh ribbon. In an example, a longitudinal series of loops (and/or segments) in a longitudinal mesh ribbon can have different lengths, widths, and/or inter-loop (inter-segment) connection angles or curvatures along the distal-to-proximal length of the ribbon. In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form a better three-dimensional occlusive mass within an aneurysm sac.

In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form a denser three-dimensional occlusive mass within an aneurysm sac. In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form a generally-globular, spherical, and/or ellipsoidal three-dimensional occlusive mass within an aneurysm sac. In an example, a longitudinal series of loops (and/or segments) in a longitudinal mesh ribbon can have different lengths, widths, and/or inter-loop (inter-segment) connection angles or curvatures in a distal-to-proximal progression along the length of the ribbon in order to form an irregularly-shaped three-dimensional occlusive mass which conforms to the walls of even an irregularly-shaped aneurysm sac.

In an example, proximal loops (and/or segments) can have a smaller lengths, widths, and/or inter-loop (inter-segment) connection angles or curvatures than distal loops in a longitudinal mesh ribbon. In an example, a longitudinal series of loops (and/or segments) in a longitudinal mesh ribbon can have progressively-smaller lengths, widths, and/or inter-loop connection angles or curvatures in a distal-to-proximal sequence along the length of the ribbon. In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form a better three-dimensional occlusive mass within an aneurysm sac. In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form a denser three-dimensional occlusive mass within an aneurysm sac.

In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form a generally-globular, spherical, and/or ellipsoidal three-dimensional occlusive mass within an aneurysm sac. In an example, a longitudinal series of loops (and/or segments) in a longitudinal mesh ribbon can have progressively-smaller lengths, widths, and/or inter-loop connection angles or curvatures in a distal-to-proximal progression along the length of the ribbon in order to form an irregularly-shaped three-dimensional occlusive mass which conforms to the walls of even an irregularly-shaped aneurysm sac.

In an example, loops (and/or segments) of a mesh ribbon can become smaller and smaller along the length of the ribbon to better fill the central space of an aneurysm sac. In an example, loops (and/or segments) can be arranged in a distal-to-proximal sequence of decreasing size, especially if they are configured to form a sphere by accumulation of mass in an outside-to-inside manner within a sphere. In an example, a distal (outer-placed) loop (and/or segment) in distal-to-proximal sequence of loops (and/or segments) can be larger than a proximal (inner-placed) loop (and/or segment) in that sequence. In an example, the most distal connections can be spaced to form loops which span the entire circumference of the aneurysm sac but successive loops can become smaller and smaller to better fill the central space of the aneurysm sac. In an example, loops (and/or segments) can be arranged in distal-to-proximal sequence of decreasing size, especially if they are configured to form a sphere by accumulation of mass in an outside-to-inside manner within a sphere.

In an example, pairs of loops (and/or segments) can be connected to each other at different angles (relative to a longitudinal axis of a device). In an example, a distal-to-proximal sequence of loops (and/or segments) can be connected to each other at a progressive sequence of angles. In an example, a distal-to-proximal sequence of loops (and/or segments) can be connected to each other with distal-to-proximally-decreasing angle degrees so that the loops (and/or segments) are biased to form a sphere, ellipsoid, or other three-dimensional mass upon insertion into an aneurysm sac. In an example, a distal-to-proximal sequence of loop sections can be connected to each other with distal-to-proximally-decreasing angle degrees so that the loops (and/or segments) are biased to form a sphere, ellipsoid, or other three-dimensional mass upon insertion into an aneurysm sac.

In an example, a longitudinal (distal-to-proximal) series of loops (and/or segments) in a longitudinal mesh ribbon can all have the same thickness, density, porosity, elasticity, stiffness, flexibility, and/or durometer along the entire (distal-to-proximal) length of the ribbon. Alternatively, proximal loops (and/or segments) can have different thicknesses, densities, porosities, elasticity levels, stiffness levels, flexibility levels, and/or durometers than distal loops in a longitudinal mesh ribbon. In an example, proximal loops (and/or segments) can be less thick, less dense, more porous, more elastic, less stiff, more flexible, and/or lower durometer than distal loops in a longitudinal mesh ribbon. In an example, a longitudinal series of loops (and/or segments) in a longitudinal mesh ribbon can have different thicknesses, densities, porosities, elasticity levels, stiffness levels, flexibility levels, and/or durometers along the distal-to-proximal length of the ribbon.

In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form a better three-dimensional occlusive mass within an aneurysm sac. In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form a denser three-dimensional occlusive mass within an aneurysm sac.

In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form a generally-globular, spherical, and/or ellipsoidal three-dimensional occlusive mass within an aneurysm sac. In an example, a longitudinal series of loops (and/or segments) in a longitudinal mesh ribbon can have different thicknesses, densities, porosities, elasticity levels, stiffness levels, flexibility levels, and/or durometers in a distal-to-proximal progression along the length of the ribbon in order to form an irregularly-shaped three-dimensional occlusive mass which conforms to the walls of even an irregularly-shaped aneurysm sac. Alternatively, distal loops (and/or segments) can be less thick, less dense, more porous, more elastic, less stiff, more flexible, and/or lower durometer than proximal loops in a longitudinal mesh ribbon.

In an example, a distal-to-proximal sequence of loops (and/or segments) can be connected to each other with a distal-to-proximal sequence of alternating (greater, then lower) angle degrees so that the loops (and/or segments) are biased to form a spherical, elliptical, or other arcuate mass upon insertion into an aneurysm sac. In an example, a proximal portion of an embolic ribbon can be more elastic than its distal portion, or vice versa. In an example, a proximal portion of an embolic ribbon can be thicker than its distal portion, or vice versa. In another example, a proximal portion of an embolic ribbon can be wider than its distal portion, or vice versa.

In an example, a device user can remotely change the density of a distal loop (and/or segment) relative to that of a proximal loop (and/or segment) in a longitudinal embolic ribbon during deployment of the ribbon into an aneurysm sac. In an example, a device user can remotely change the density of a loop (and/or segment) of a longitudinal embolic ribbon during deployment of the ribbon into an aneurysm sac. In an example, a device user can remotely change the density of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the durometer of a distal loop (and/or segment) relative to that of a proximal loop (and/or segment) in a longitudinal embolic ribbon during deployment of the ribbon into an aneurysm sac. In an example, a device user can remotely change the durometer of a loop (and/or segment) of a longitudinal embolic ribbon during deployment of the ribbon into an aneurysm sac. In an example, a device user can remotely change the durometer of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the elasticity of a distal loop (and/or segment) relative to that of a proximal loop (and/or segment) in a longitudinal embolic ribbon during deployment of the ribbon into an aneurysm sac. In an example, a device user can remotely change the elasticity of a loop (and/or segment) of a longitudinal embolic ribbon during deployment of the ribbon into an aneurysm sac. In an example, a device user can remotely change the elasticity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the flexibility of a distal loop (and/or segment) relative to that of a proximal loop (and/or segment) in a longitudinal embolic ribbon during deployment of the ribbon into an aneurysm sac. In an example, a device user can remotely change the flexibility of a loop (and/or segment) of a longitudinal embolic ribbon during deployment of the ribbon into an aneurysm sac. In an example, a device user can remotely change the flexibility of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac. In an example, a device user can remotely change the inter-loop (inter-segment) connection angle or curvature of a loop (and/or segment) of a longitudinal embolic ribbon during deployment of the ribbon into an aneurysm sac. In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the length of a distal loop (and/or segment) relative to that of a proximal loop (and/or segment) in a longitudinal embolic ribbon during deployment of the ribbon into an aneurysm sac. In an example, a device user can remotely change the length of a loop (and/or segment) of a longitudinal embolic ribbon during deployment of the ribbon into an aneurysm sac. In an example, a device user can remotely change the length of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the porosity of a distal loop (and/or segment) relative to that of a proximal loop (and/or segment) in a longitudinal embolic ribbon during deployment of the ribbon into an aneurysm sac. In an example, a device user can remotely change the porosity of a loop (and/or segment) of a longitudinal embolic ribbon during deployment of the ribbon into an aneurysm sac. In an example, a device user can remotely change the porosity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the stiffness of a distal loop (and/or segment) relative to that of a proximal loop (and/or segment) in a longitudinal embolic ribbon during deployment of the ribbon into an aneurysm sac. In an example, a device user can remotely change the stiffness of a loop (and/or segment) of a longitudinal embolic ribbon during deployment of the ribbon into an aneurysm sac. In an example, a device user can remotely change the stiffness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the thickness of a distal loop (and/or segment) relative to that of a proximal loop (and/or segment) in a longitudinal embolic ribbon during deployment of the ribbon into an aneurysm sac. In an example, a device user can remotely change the thickness of a loop (and/or segment) of a longitudinal embolic ribbon during deployment of the ribbon into an aneurysm sac. In an example, a device user can remotely change the thickness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the width of a distal loop (and/or segment) relative to that of a proximal loop (and/or segment) in a longitudinal embolic ribbon during deployment of the ribbon into an aneurysm sac. In an example, a device user can remotely change the width of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon. In an example, a device user can remotely change the width of a loop (and/or segment) of a longitudinal embolic ribbon during deployment of the ribbon into an aneurysm sac.

In an example, a user can adjust the cross-sectional asymmetry of an embolic ribbon by adjusting its elasticity, flexibility, shape, length, and/or width as it is deployed within an aneurysm sac. In an example, the cross-sectional symmetry of an embolic ribbon can be adjusted by a user in real-time (as an embolic ribbon is being inserted into an aneurysm sac) so as to guide and/or steer the bending movement of the ribbon as it is deployed. In an example, the direction in which one loop (and/or segment) of this device moves relative to another loop (and/or segment) as the sections are inserted into an aneurysm can be steered, changed, and/or adjusted by a user in real time. In an example, the orientation of one loop (and/or segment) relative to another loop (and/or segment) can be steered and/or adjusted in real time as the sections are inserted into an aneurysm.

In an example, a progression of sizes and/or widths of a series of multiple loops (and/or segments) can be adjusted, controlled, and/or varied in real time by a person deploying them in order to best match the contours of a specific aneurysm sac. In an example, a progression of sizes and/or widths of a series of multiple loops (and/or segments) can be adjusted, controlled, and/or varied in real time by a person deploying them in order to best fill a specific aneurysm sac. This enables a user to guide the formation of an arcuate three-dimensional occlusive mass which confirms to the walls of an irregularly-shaped aneurysm sac.

In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first loop (and/or segment) and/or to a second loop (and/or segment) can change the cross-sectional asymmetry of an embolic ribbon, thereby biasing the embolic ribbon to bend to the right or to the left. In an example, selective application of electromagnetic energy can change the elasticity, flexibility, and/or shape of a left-side portion or a right-side portion of the ribbon.

In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, this device can further comprise an electromagnetic energy source which enables a user to selectively apply electromagnetic energy to a portion of an embolic ribbon as the ribbon is deployed within an aneurysm sac. In an example, application of electromagnetic energy to a portion of an embolic ribbon can change the size, shape, and/or orientation of one or more loops in the ribbon by expanding or contracting one or more wires in the ribbon. In an example, application of electromagnetic energy to a portion of an embolic ribbon can change the size, shape, and/or orientation of one or more loops in the ribbon by detaching one or more wires in the ribbon.

In an example, differential pulling on left-side vs. right-side pull-cords can bias the longitudinal axis of connected loops (and/or segments) into curvature as these segments are inserted into an aneurysm. In an example, pulling or pushing a wire connected to the first loop (and/or segment) or connected to the second loop (and/or segment) can bias the embolic ribbon to bend to the right or to the left. In an example, this curvature can cause connected segments to accumulate into a spherical, elliptical, or other arcuate mass which occludes the aneurysm. In an example, the orientation of one loop (and/or segment) relative to another loop (and/or segment) can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections.

In an example, successive loops and/or wide longitudinal segments can become smaller to better fill the central space of an aneurysm sac. In an example, the most distal connections can be spaced to form loops which span the entire circumference of the aneurysm sac but successive loops can become smaller and smaller to better fill the central space of the aneurysm sac. In an example, wide longitudinal segments can be arranged in distal-to-proximal sequence of decreasing size, especially if they are configured to form a sphere by accumulation of mass in an outside-to-inside manner within a sphere. In an example, a distal (outer-placed) segment in distal-to-proximal sequence of wide longitudinal segments can be larger than a proximal (inner-placed) segment in that sequence.

In an example, a distal-to-proximal sequence of longitudinal sections can be connected to each other at a progressive sequence of angles. In an example, a distal-to-proximal sequence of longitudinal sections can be connected to each other with distal-to-proximally-decreasing angle degrees so that the longitudinal sections are biased to form a sphere, ellipsoid, or other three-dimensional mass upon insertion into an aneurysm sac. In an example, a distal-to-proximal sequence of longitudinal sections can be connected to each other with a distal-to-proximal sequence of alternating (greater, then lower) angle degrees so that the longitudinal sections are biased to form a spherical, elliptical, or other arcuate mass upon insertion into an aneurysm sac. In an example, pairs of longitudinal sections can be connected to each other at different angles (relative to a longitudinal axis of a device).

In an example, the progression of sizes and/or widths of a series of multiple shape-changing embolic members can be adjusted, controlled, and/or varied in real time by a person deploying them in order to best match the contours of a specific aneurysm sac. In an example, the progression of sizes and/or widths of a series of multiple shape-changing embolic members can be adjusted, controlled, and/or varied in real time by a person deploying them in order to best fill a specific aneurysm sac. In an example, the direction in which one longitudinal section of this device moves relative to another longitudinal section as the sections are inserted into an aneurysm can be steered, changed, and/or adjusted by a user in real time. In an example, the orientation of one longitudinal section relative to another longitudinal section can be steered and/or adjusted in real time as the sections are inserted into an aneurysm. In an example, the cross-sectional symmetry of an undulating embolic ribbon can be adjusted by a user in real-time (as an embolic ribbon is being inserted into an aneurysm sac) so as to guide and/or steer the bending movement of the ribbon as it is deployed. This enables a user to guide the formation of an arcuate three-dimensional occlusive mass which confirms to the walls of an irregularly-shaped aneurysm sac. In an example, a user can adjust the cross-sectional asymmetry of an undulating embolic ribbon by adjusting its elasticity, flexibility, shape, length, and/or width as it is deployed within an aneurysm sac.

In an example, this device can further comprise an electromagnetic energy source which enables a user to selectively apply electromagnetic energy to a portion of an embolic ribbon as the ribbon is deployed within an aneurysm sac. In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first undulating strip and/or to a second undulating strip can change the cross-sectional asymmetry of the undulating embolic ribbon, thereby biasing the embolic ribbon to bend to the right or to the left. In an example, selective application of electromagnetic energy can change the elasticity, flexibility, and/or shape of a left-side portion or a right-side portion of the ribbon. In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, differential pulling on left-side vs. right-side pull-cords can bias the longitudinal axis of connected segments into curvature as these segments are inserted into an aneurysm. In an example, this curvature can cause connected segments to accumulate into a spherical, elliptical, or other arcuate mass which occludes the aneurysm. In an example, pulling or pushing a wire connected to the first undulating strip or connected to the second undulating strip can bias the undulating embolic ribbon to bend to the right or to the left. In an example, the orientation of one longitudinal section relative to another longitudinal section can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections. Relevant variations discussed elsewhere in this or prior-linked disclosures can also be applied to this example.

Figure 65:
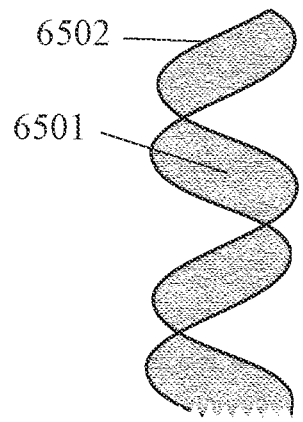
FIGS. 65 through 67 show three views of an intrasacular aneurysm occlusion device comprising a ribbon with loops whose length can be selectively changed by a user during deployment.
Figure 66:
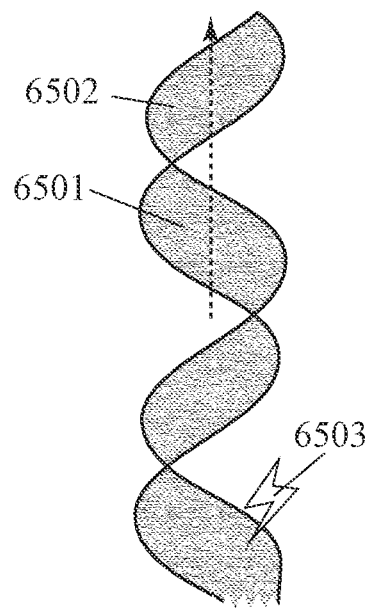
Figure 67:
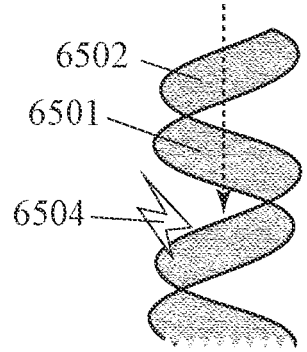

FIGS. 65 through 67 show three views at different times of another example of an intrasacular aneurysm occlusion device comprising a longitudinal mesh ribbon with a proximal-to-distal series of loops (and/or segments). The longitudinal mesh ribbon has a longitudinal series of loops (and/or segments), including first loop 6501 and second loop 6502, wherein the second loop is more distal than the first loop and, correspondingly, the first loop is more proximal than the second loop. The ribbon is inserted into an aneurysm, where it accumulates and overlaps onto itself into an arcuate three-dimensional occlusive mass which fills the aneurysm sac. In an example, the ribbon can progressively fill the aneurysm sac in an outer-layer to inner-core progression. In this example, the lengths of one or more loops (and/or segments) of the ribbon are changed by the user of the device by the application of electromagnetic energy (6503 or 6504) to one or more portions of the ribbon during deployment of the device into an aneurysm sac.

FIG. 65 shows this ribbon at a one point in time before electromagnetic energy has been applied to the ribbon. FIG. 66 shows this device at a different point in time wherein electromagnetic energy 6503 has been applied to a first portion of the ribbon, thereby causing one or more loops (and/or segments) in the ribbon to become longer. FIG. 67 shows this device at a different point in time wherein electromagnetic energy 6504 has been applied to a second portion of the ribbon, thereby causing one or more loops (and/or segments) in the ribbon to become shorter. Giving a user the ability to selectively increase or decrease the length of one or more loops (and/or segments) of the ribbon during deployment can help the user to steer and shape the ribbon to form a better three-dimensional occlusive mass in the aneurysm sac.

In an example, a device user can remotely change the density of a distal loop (and/or segment) relative to that of a proximal loop (and/or segment) in a longitudinal embolic ribbon during deployment of the ribbon into an aneurysm sac. In an example, a device user can remotely change the density of a loop (and/or segment) of a longitudinal embolic ribbon during deployment of the ribbon into an aneurysm sac. In an example, a device user can remotely change the density of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the durometer of a distal loop (and/or segment) relative to that of a proximal loop (and/or segment) in a longitudinal embolic ribbon during deployment of the ribbon into an aneurysm sac. In an example, a device user can remotely change the durometer of a loop (and/or segment) of a longitudinal embolic ribbon during deployment of the ribbon into an aneurysm sac. In an example, a device user can remotely change the durometer of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the elasticity of a distal loop (and/or segment) relative to that of a proximal loop (and/or segment) in a longitudinal embolic ribbon during deployment of the ribbon into an aneurysm sac. In an example, a device user can remotely change the elasticity of a loop (and/or segment) of a longitudinal embolic ribbon during deployment of the ribbon into an aneurysm sac. In an example, a device user can remotely change the elasticity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the flexibility of a distal loop (and/or segment) relative to that of a proximal loop (and/or segment) in a longitudinal embolic ribbon during deployment of the ribbon into an aneurysm sac. In an example, a device user can remotely change the flexibility of a loop (and/or segment) of a longitudinal embolic ribbon during deployment of the ribbon into an aneurysm sac. In an example, a device user can remotely change the flexibility of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac. In an example, a device user can remotely change the inter-loop (inter-segment) connection angle or curvature of a loop (and/or segment) of a longitudinal embolic ribbon during deployment of the ribbon into an aneurysm sac. In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the length of a distal loop (and/or segment) relative to that of a proximal loop (and/or segment) in a longitudinal embolic ribbon during deployment of the ribbon into an aneurysm sac. In an example, a device user can remotely change the length of a loop (and/or segment) of a longitudinal embolic ribbon during deployment of the ribbon into an aneurysm sac. In an example, a device user can remotely change the length of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the porosity of a distal loop (and/or segment) relative to that of a proximal loop (and/or segment) in a longitudinal embolic ribbon during deployment of the ribbon into an aneurysm sac. In an example, a device user can remotely change the porosity of a loop (and/or segment) of a longitudinal embolic ribbon during deployment of the ribbon into an aneurysm sac. In an example, a device user can remotely change the porosity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the stiffness of a distal loop (and/or segment) relative to that of a proximal loop (and/or segment) in a longitudinal embolic ribbon during deployment of the ribbon into an aneurysm sac. In an example, a device user can remotely change the stiffness of a loop (and/or segment) of a longitudinal embolic ribbon during deployment of the ribbon into an aneurysm sac. In an example, a device user can remotely change the stiffness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the thickness of a distal loop (and/or segment) relative to that of a proximal loop (and/or segment) in a longitudinal embolic ribbon during deployment of the ribbon into an aneurysm sac. In an example, a device user can remotely change the thickness of a loop (and/or segment) of a longitudinal embolic ribbon during deployment of the ribbon into an aneurysm sac. In an example, a device user can remotely change the thickness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the width of a distal loop (and/or segment) relative to that of a proximal loop (and/or segment) in a longitudinal embolic ribbon during deployment of the ribbon into an aneurysm sac. In an example, a device user can remotely change the width of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon. In an example, a device user can remotely change the width of a loop (and/or segment) of a longitudinal embolic ribbon during deployment of the ribbon into an aneurysm sac.

In an example, a user can adjust the cross-sectional asymmetry of an embolic ribbon by adjusting its elasticity, flexibility, shape, length, and/or width as it is deployed within an aneurysm sac. In an example, the cross-sectional symmetry of an embolic ribbon can be adjusted by a user in real-time (as an embolic ribbon is being inserted into an aneurysm sac) so as to guide and/or steer the bending movement of the ribbon as it is deployed. In an example, the direction in which one loop (and/or segment) of this device moves relative to another loop (and/or segment) as the sections are inserted into an aneurysm can be steered, changed, and/or adjusted by a user in real time. In an example, the orientation of one loop (and/or segment) relative to another loop (and/or segment) can be steered and/or adjusted in real time as the sections are inserted into an aneurysm.

In an example, a progression of sizes and/or widths of a series of multiple loops (and/or segments) can be adjusted, controlled, and/or varied in real time by a person deploying them in order to best match the contours of a specific aneurysm sac. In an example, a progression of sizes and/or widths of a series of multiple loops (and/or segments) can be adjusted, controlled, and/or varied in real time by a person deploying them in order to best fill a specific aneurysm sac. This enables a user to guide the formation of an arcuate three-dimensional occlusive mass which confirms to the walls of an irregularly-shaped aneurysm sac.

In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first loop (and/or segment) and/or to a second loop (and/or segment) can change the cross-sectional asymmetry of an embolic ribbon, thereby biasing the embolic ribbon to bend to the right or to the left. In an example, selective application of electromagnetic energy can change the elasticity, flexibility, and/or shape of a left-side portion or a right-side portion of the ribbon.

In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, this device can further comprise an electromagnetic energy source which enables a user to selectively apply electromagnetic energy to a portion of an embolic ribbon as the ribbon is deployed within an aneurysm sac. In an example, application of electromagnetic energy to a portion of an embolic ribbon can change the size, shape, and/or orientation of one or more loops in the ribbon by expanding or contracting one or more wires in the ribbon. In an example, application of electromagnetic energy to a portion of an embolic ribbon can change the size, shape, and/or orientation of one or more loops in the ribbon by detaching one or more wires in the ribbon.

In an example, differential pulling on left-side vs. right-side pull-cords can bias the longitudinal axis of connected loops (and/or segments) into curvature as these segments are inserted into an aneurysm. In an example, pulling or pushing a wire connected to the first loop (and/or segment) or connected to the second loop (and/or segment) can bias the embolic ribbon to bend to the right or to the left. In an example, this curvature can cause connected segments to accumulate into a spherical, elliptical, or other arcuate mass which occludes the aneurysm. In an example, the orientation of one loop (and/or segment) relative to another loop (and/or segment) can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections.

In an example, the progression of sizes and/or widths of a series of multiple shape-changing embolic members can be adjusted, controlled, and/or varied in real time by a person deploying them in order to best match the contours of a specific aneurysm sac. In an example, the progression of sizes and/or widths of a series of multiple shape-changing embolic members can be adjusted, controlled, and/or varied in real time by a person deploying them in order to best fill a specific aneurysm sac. In an example, the direction in which one longitudinal section of this device moves relative to another longitudinal section as the sections are inserted into an aneurysm can be steered, changed, and/or adjusted by a user in real time. In an example, the orientation of one longitudinal section relative to another longitudinal section can be steered and/or adjusted in real time as the sections are inserted into an aneurysm. In an example, the cross-sectional symmetry of an undulating embolic ribbon can be adjusted by a user in real-time (as an embolic ribbon is being inserted into an aneurysm sac) so as to guide and/or steer the bending movement of the ribbon as it is deployed. This enables a user to guide the formation of an arcuate three-dimensional occlusive mass which confirms to the walls of an irregularly-shaped aneurysm sac. In an example, a user can adjust the cross-sectional asymmetry of an undulating embolic ribbon by adjusting its elasticity, flexibility, shape, length, and/or width as it is deployed within an aneurysm sac.

In an example, this device can further comprise an electromagnetic energy source which enables a user to selectively apply electromagnetic energy to a portion of an embolic ribbon as the ribbon is deployed within an aneurysm sac. In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first undulating strip and/or to a second undulating strip can change the cross-sectional asymmetry of the undulating embolic ribbon, thereby biasing the embolic ribbon to bend to the right or to the left. In an example, selective application of electromagnetic energy can change the elasticity, flexibility, and/or shape of a left-side portion or a right-side portion of the ribbon. In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, differential pulling on left-side vs. right-side pull-cords can bias the longitudinal axis of connected segments into curvature as these segments are inserted into an aneurysm. In an example, this curvature can cause connected segments to accumulate into a spherical, elliptical, or other arcuate mass which occludes the aneurysm. In an example, pulling or pushing a wire connected to the first undulating strip or connected to the second undulating strip can bias the undulating embolic ribbon to bend to the right or to the left. In an example, the orientation of one longitudinal section relative to another longitudinal section can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections. Relevant variations discussed elsewhere in this or prior-linked disclosures can also be applied to this example.

Figure 68:
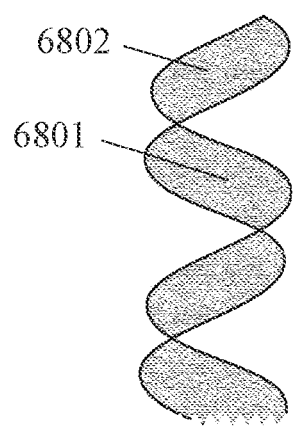
FIGS. 68 through 70 show three views of an intrasacular aneurysm occlusion device comprising a ribbon with loops whose inter-loop connection angles or curvatures can be selectively changed by a user during deployment.
Figure 69:
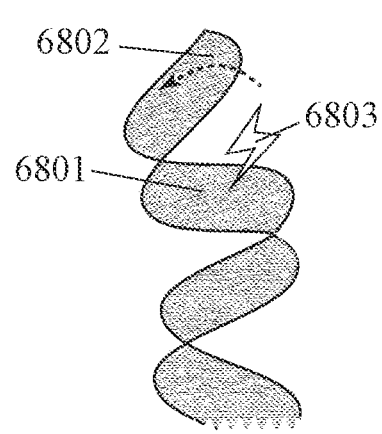
Figure 70:
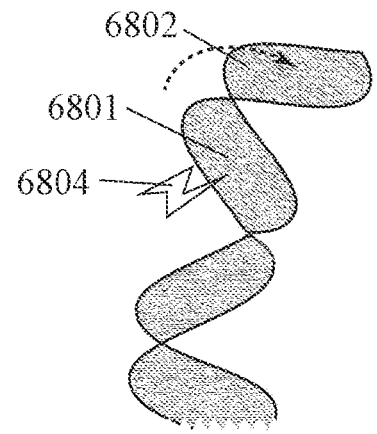

FIGS. 68 through 70 show three views at different times of another example of an intrasacular aneurysm occlusion device comprising a longitudinal mesh ribbon with a proximal-to-distal series of loops (and/or segments). The longitudinal mesh ribbon has a longitudinal series of loops (and/or segments), including first loop 6801 and second loop 6802, wherein the second loop is more distal than the first loop and, correspondingly, the first loop is more proximal than the second loop. The ribbon is inserted into an aneurysm, where it accumulates and overlaps onto itself into an arcuate three-dimensional occlusive mass which fills the aneurysm sac. In an example, the ribbon can progressively fill the aneurysm sac in an outer-layer to inner-core progression. In this example, the inter-loop connection angles and/or curvatures of one or more loops (and/or segments) of the ribbon are changed by the user of the device by the application of electromagnetic energy (6803 or 6804) to one or more portions of the ribbon during deployment of the device into an aneurysm sac.

FIG. 68 shows this ribbon at a one point in time before electromagnetic energy has been applied to the ribbon. FIG. 69 shows this device at a different point in time wherein electromagnetic energy 6803 has been applied to a first portion of the ribbon, thereby changing the inter-loop connection angle and/or curvature of one or more loops (and/or segments) in the ribbon, causing the loops to curve and/or bend in a first direction. FIG. 70 shows this device at a different point in time wherein electromagnetic energy 6804 has been applied to a second portion of the ribbon, thereby changing the inter-loop connection angle and/or curvature of one or more loops (and/or segments) in the ribbon, causing the loops to curve and/or bend in a second direction. Giving a user the ability to selectively curve and/or bend one or more loops (and/or segments) of the ribbon during deployment can help the user to steer and shape the ribbon to form a better three-dimensional occlusive mass in the aneurysm sac.

In an example, a device user can remotely change the density of a distal loop (and/or segment) relative to that of a proximal loop (and/or segment) in a longitudinal embolic ribbon during deployment of the ribbon into an aneurysm sac. In an example, a device user can remotely change the density of a loop (and/or segment) of a longitudinal embolic ribbon during deployment of the ribbon into an aneurysm sac. In an example, a device user can remotely change the density of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the durometer of a distal loop (and/or segment) relative to that of a proximal loop (and/or segment) in a longitudinal embolic ribbon during deployment of the ribbon into an aneurysm sac. In an example, a device user can remotely change the durometer of a loop (and/or segment) of a longitudinal embolic ribbon during deployment of the ribbon into an aneurysm sac. In an example, a device user can remotely change the durometer of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the elasticity of a distal loop (and/or segment) relative to that of a proximal loop (and/or segment) in a longitudinal embolic ribbon during deployment of the ribbon into an aneurysm sac. In an example, a device user can remotely change the elasticity of a loop (and/or segment) of a longitudinal embolic ribbon during deployment of the ribbon into an aneurysm sac. In an example, a device user can remotely change the elasticity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the flexibility of a distal loop (and/or segment) relative to that of a proximal loop (and/or segment) in a longitudinal embolic ribbon during deployment of the ribbon into an aneurysm sac. In an example, a device user can remotely change the flexibility of a loop (and/or segment) of a longitudinal embolic ribbon during deployment of the ribbon into an aneurysm sac. In an example, a device user can remotely change the flexibility of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac. In an example, a device user can remotely change the inter-loop (inter-segment) connection angle or curvature of a loop (and/or segment) of a longitudinal embolic ribbon during deployment of the ribbon into an aneurysm sac. In an example, a device user can remotely change the inter-loop (inter-segment) connection angle or curvature of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the length of a distal loop (and/or segment) relative to that of a proximal loop (and/or segment) in a longitudinal embolic ribbon during deployment of the ribbon into an aneurysm sac. In an example, a device user can remotely change the length of a loop (and/or segment) of a longitudinal embolic ribbon during deployment of the ribbon into an aneurysm sac. In an example, a device user can remotely change the length of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the porosity of a distal loop (and/or segment) relative to that of a proximal loop (and/or segment) in a longitudinal embolic ribbon during deployment of the ribbon into an aneurysm sac. In an example, a device user can remotely change the porosity of a loop (and/or segment) of a longitudinal embolic ribbon during deployment of the ribbon into an aneurysm sac. In an example, a device user can remotely change the porosity of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the stiffness of a distal loop (and/or segment) relative to that of a proximal loop (and/or segment) in a longitudinal embolic ribbon during deployment of the ribbon into an aneurysm sac. In an example, a device user can remotely change the stiffness of a loop (and/or segment) of a longitudinal embolic ribbon during deployment of the ribbon into an aneurysm sac. In an example, a device user can remotely change the stiffness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the thickness of a distal loop (and/or segment) relative to that of a proximal loop (and/or segment) in a longitudinal embolic ribbon during deployment of the ribbon into an aneurysm sac. In an example, a device user can remotely change the thickness of a loop (and/or segment) of a longitudinal embolic ribbon during deployment of the ribbon into an aneurysm sac. In an example, a device user can remotely change the thickness of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon.

In an example, a device user can remotely change the width of a distal loop (and/or segment) relative to that of a proximal loop (and/or segment) in a longitudinal embolic ribbon during deployment of the ribbon into an aneurysm sac. In an example, a device user can remotely change the width of a distal loop (and/or segment) relative to that of a proximal loop (and/or segment) in a longitudinal embolic ribbon during deployment of the ribbon into an aneurysm sac by: applying electromagnetic energy to a portion of the ribbon; or by moving (e.g. pulling, pushing, or rotating) a wire or cord connected to the ribbon. In an example, a device user can remotely change the width of a loop (and/or segment) of a longitudinal embolic ribbon during deployment of the ribbon into an aneurysm sac.

In an example, a user can adjust the cross-sectional asymmetry of an embolic ribbon by adjusting its elasticity, flexibility, shape, length, and/or width as it is deployed within an aneurysm sac. In an example, the cross-sectional symmetry of an embolic ribbon can be adjusted by a user in real-time (as an embolic ribbon is being inserted into an aneurysm sac) so as to guide and/or steer the bending movement of the ribbon as it is deployed. In an example, the direction in which one loop (and/or segment) of this device moves relative to another loop (and/or segment) as the sections are inserted into an aneurysm can be steered, changed, and/or adjusted by a user in real time. In an example, the orientation of one loop (and/or segment) relative to another loop (and/or segment) can be steered and/or adjusted in real time as the sections are inserted into an aneurysm.

In an example, a progression of sizes and/or widths of a series of multiple loops (and/or segments) can be adjusted, controlled, and/or varied in real time by a person deploying them in order to best match the contours of a specific aneurysm sac. In an example, a progression of sizes and/or widths of a series of multiple loops (and/or segments) can be adjusted, controlled, and/or varied in real time by a person deploying them in order to best fill a specific aneurysm sac. This enables a user to guide the formation of an arcuate three-dimensional occlusive mass which confirms to the walls of an irregularly-shaped aneurysm sac.

In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first loop (and/or segment) and/or to a second loop (and/or segment) can change the cross-sectional asymmetry of an embolic ribbon, thereby biasing the embolic ribbon to bend to the right or to the left. In an example, selective application of electromagnetic energy can change the elasticity, flexibility, and/or shape of a left-side portion or a right-side portion of the ribbon.

In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, this device can further comprise an electromagnetic energy source which enables a user to selectively apply electromagnetic energy to a portion of an embolic ribbon as the ribbon is deployed within an aneurysm sac. In an example, application of electromagnetic energy to a portion of an embolic ribbon can change the size, shape, and/or orientation of one or more loops in the ribbon by expanding or contracting one or more wires in the ribbon. In an example, application of electromagnetic energy to a portion of an embolic ribbon can change the size, shape, and/or orientation of one or more loops in the ribbon by detaching one or more wires in the ribbon.

In an example, differential pulling on left-side vs. right-side pull-cords can bias the longitudinal axis of connected loops (and/or segments) into curvature as these segments are inserted into an aneurysm. In an example, pulling or pushing a wire connected to the first loop (and/or segment) or connected to the second loop (and/or segment) can bias the embolic ribbon to bend to the right or to the left. In an example, this curvature can cause connected segments to accumulate into a spherical, elliptical, or other arcuate mass which occludes the aneurysm. In an example, the orientation of one loop (and/or segment) relative to another loop (and/or segment) can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections.

In an example, the progression of sizes and/or widths of a series of multiple shape-changing embolic members can be adjusted, controlled, and/or varied in real time by a person deploying them in order to best match the contours of a specific aneurysm sac. In an example, the progression of sizes and/or widths of a series of multiple shape-changing embolic members can be adjusted, controlled, and/or varied in real time by a person deploying them in order to best fill a specific aneurysm sac. In an example, the direction in which one longitudinal section of this device moves relative to another longitudinal section as the sections are inserted into an aneurysm can be steered, changed, and/or adjusted by a user in real time. In an example, the orientation of one longitudinal section relative to another longitudinal section can be steered and/or adjusted in real time as the sections are inserted into an aneurysm. In an example, the cross-sectional symmetry of an undulating embolic ribbon can be adjusted by a user in real-time (as an embolic ribbon is being inserted into an aneurysm sac) so as to guide and/or steer the bending movement of the ribbon as it is deployed. This enables a user to guide the formation of an arcuate three-dimensional occlusive mass which confirms to the walls of an irregularly-shaped aneurysm sac. In an example, a user can adjust the cross-sectional asymmetry of an undulating embolic ribbon by adjusting its elasticity, flexibility, shape, length, and/or width as it is deployed within an aneurysm sac.

In an example, this device can further comprise an electromagnetic energy source which enables a user to selectively apply electromagnetic energy to a portion of an embolic ribbon as the ribbon is deployed within an aneurysm sac. In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first undulating strip and/or to a second undulating strip can change the cross-sectional asymmetry of the undulating embolic ribbon, thereby biasing the embolic ribbon to bend to the right or to the left. In an example, selective application of electromagnetic energy can change the elasticity, flexibility, and/or shape of a left-side portion or a right-side portion of the ribbon. In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, differential pulling on left-side vs. right-side pull-cords can bias the longitudinal axis of connected segments into curvature as these segments are inserted into an aneurysm. In an example, this curvature can cause connected segments to accumulate into a spherical, elliptical, or other arcuate mass which occludes the aneurysm. In an example, pulling or pushing a wire connected to the first undulating strip or connected to the second undulating strip can bias the undulating embolic ribbon to bend to the right or to the left. In an example, the orientation of one longitudinal section relative to another longitudinal section can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections. Relevant variations discussed elsewhere in this or prior-linked disclosures can also be applied to this example.

In an example, successive loops and/or wide longitudinal segments can become smaller to better fill the central space of an aneurysm sac. In an example, the most distal connections can be spaced to form loops which span the entire circumference of the aneurysm sac but successive loops can become smaller and smaller to better fill the central space of the aneurysm sac. In an example, wide longitudinal segments can be arranged in distal-to-proximal sequence of decreasing size, especially if they are configured to form a sphere by accumulation of mass in an outside-to-inside manner within a sphere. In an example, a distal (outer-placed) segment in distal-to-proximal sequence of wide longitudinal segments can be larger than a proximal (inner-placed) segment in that sequence.

In an example, a distal-to-proximal sequence of longitudinal sections can be connected to each other at a progressive sequence of angles. In an example, a distal-to-proximal sequence of longitudinal sections can be connected to each other with distal-to-proximally-decreasing angle degrees so that the longitudinal sections are biased to form a sphere, ellipsoid, or other three-dimensional mass upon insertion into an aneurysm sac. In an example, a distal-to-proximal sequence of longitudinal sections can be connected to each other with a distal-to-proximal sequence of alternating (greater, then lower) angle degrees so that the longitudinal sections are biased to form a spherical, elliptical, or other arcuate mass upon insertion into an aneurysm sac. In an example, pairs of longitudinal sections can be connected to each other at different angles (relative to a longitudinal axis of a device).

In an example, the progression of sizes and/or widths of a series of multiple shape-changing embolic members can be adjusted, controlled, and/or varied in real time by a person deploying them in order to best match the contours of a specific aneurysm sac. In an example, the progression of sizes and/or widths of a series of multiple shape-changing embolic members can be adjusted, controlled, and/or varied in real time by a person deploying them in order to best fill a specific aneurysm sac. In an example, the direction in which one longitudinal section of this device moves relative to another longitudinal section as the sections are inserted into an aneurysm can be steered, changed, and/or adjusted by a user in real time. In an example, the orientation of one longitudinal section relative to another longitudinal section can be steered and/or adjusted in real time as the sections are inserted into an aneurysm. In an example, the cross-sectional symmetry of an undulating embolic ribbon can be adjusted by a user in real-time (as an embolic ribbon is being inserted into an aneurysm sac) so as to guide and/or steer the bending movement of the ribbon as it is deployed. This enables a user to guide the formation of an arcuate three-dimensional occlusive mass which confirms to the walls of an irregularly-shaped aneurysm sac. In an example, a user can adjust the cross-sectional asymmetry of an undulating embolic ribbon by adjusting its elasticity, flexibility, shape, length, and/or width as it is deployed within an aneurysm sac.

In an example, this device can further comprise an electromagnetic energy source which enables a user to selectively apply electromagnetic energy to a portion of an embolic ribbon as the ribbon is deployed within an aneurysm sac. In an example, an aneurysm occlusion device can further comprise an electromagnetic energy source which enables a user to selectively apply electromagnetic energy to a left-side portion or to a right-side portion of an embolic ribbon as it is deployed within an aneurysm sac. In an example, application of electromagnetic energy to a first undulating strip and/or to a second undulating strip can change the cross-sectional asymmetry of the undulating embolic ribbon, thereby biasing the embolic ribbon to bend to the right or to the left. In an example, selective application of electromagnetic energy can change the elasticity, flexibility, and/or shape of a left-side portion or a right-side portion of the ribbon. In an example, selective application of electromagnetic energy to a first side of an embolic ribbon can cause the ribbon to bend in a first direction and selective application of electromagnetic energy to a second side of the embolic ribbon can cause the ribbon to bend in a second direction. In an example, selective application of electromagnetic energy to a portion of an embolic ribbon can change the elasticity, flexibility, and/or shape of that portion. In an example, this can enable a user to guide and/or steer an embolic ribbon during deployment so as to create an arcuate three-dimensional occlusive mass which optimally fills an aneurysm sac.

In an example, differential pulling on left-side vs. right-side pull-cords can bias the longitudinal axis of connected segments into curvature as these segments are inserted into an aneurysm. In an example, this curvature can cause connected segments to accumulate into a spherical, elliptical, or other arcuate mass which occludes the aneurysm. In an example, pulling or pushing a wire connected to the first undulating strip or connected to the second undulating strip can bias the undulating embolic ribbon to bend to the right or to the left. In an example, the orientation of one longitudinal section relative to another longitudinal section can be steered, changed, and/or adjusted by a user during insertion of the sections into an aneurysm by one or more mechanisms selected from the group consisting of: selectively pulling on a string or cord which connects sections together; selectively connecting sections together (e.g. by fusing or crimping); selectively disconnecting sections (e.g. by cutting or melting connectors); selectively adjusting the tension and/or elasticity of connectors between sections; and selectively inflating balloons or other compartments between sections.

I claim:

1. An intrasacular aneurysm occlusion device comprising:
   a longitudinal mesh ribbon with a distal-to-proximal series of loops or segments which is inserted into an aneurysm sac;
   wherein the mesh ribbon accumulates and overlaps onto itself to form an arcuate three-dimensional occlusive mass in the aneurysm sac; wherein the mesh ribbon has a longitudinal axis; wherein a first side of the mesh ribbon on a first side of the longitudinal axis has a first elasticity level, wherein a second side of the mesh ribbon on a second side of the longitudinal axis has a second elasticity level, wherein the second side is opposite the first side, and wherein the second elasticity level is different than the first elasticity level, wherein the distal-to-proximal series of loops or segments comprises a plurality of loops or segments.

2. The device in claim 1 wherein the plurality of loops or segments includes at least three loops or segments which are progressively smaller in size as one views them in a distal-to-proximal direction, wherein distal means closer to the end of the device which is first inserted into the person's body and proximal means farther from this end.

3. The device in claim 1 wherein the plurality of loops or segments includes at least five loops or segments which are progressively smaller in size as one views them in a distal-to-proximal direction, wherein distal means closer to the end of the device which is first inserted into the person's body and proximal means farther from this end.

4. The device in claim 1 wherein the plurality of loops or segments are progressively smaller in length as one views them in a distal-to-proximal direction, wherein distal means closer to the end of the device which is first inserted into the person's body and proximal means farther from this end.

5. The device in claim 1 wherein the plurality of loops or segments are progressively smaller in width as one views them in a distal-to-proximal direction, wherein distal means closer to the end of the device which is first inserted into the person's body and proximal means farther from this end.

6. An intrasacular aneurysm occlusion device comprising:
   a longitudinal mesh ribbon with a distal-to-proximal series of loops or segments which is inserted into an aneurysm sac;
   wherein the mesh ribbon accumulates and overlaps onto itself to form an arcuate three-dimensional occlusive mass in the aneurysm sac; wherein the mesh ribbon has a longitudinal axis; wherein a first side of the mesh ribbon on a first side of the longitudinal axis has a first elasticity level, wherein a second side of the mesh ribbon on a second side of the longitudinal axis has a second elasticity level, wherein the second side is opposite the first side, and wherein the second elasticity level is different than the first elasticity level; wherein a plurality of loops or segments in the distal-to-proximal series of loops or segments are connected by progressively smaller inter-loop connection angles and/or are progressively more curved as one views them in a distal-to-proximal direction, and wherein distal means closer to the end of the device which is first inserted into the person's body and proximal means farther from this end.

7. The device in claim 6 wherein the plurality of loops or segments includes at least three loops or segments which are connected by progressively smaller inter-loop connection angles and/or are progressively more curved as one views them in a distal-to-proximal direction.

8. The device in claim 6 wherein the plurality of loops or segments includes at least five loops or segments which are connected by progressively smaller inter-loop connection angles and/or are progressively more curved as one views them in a distal-to-proximal direction.

9. The device in claim 6 wherein the plurality of loops or segments are connected by progressively smaller inter-loop connection angles as one views them in a distal-to-proximal direction.

10. The device in claim 6 wherein the plurality of loops or segments are progressively more curved as one views them in a distal-to-proximal direction, wherein more curved means more concave or more convex.

* * * * *